(12) United States Patent
Rodrigueza et al.

(10) Patent No.: US 6,773,719 B2
(45) Date of Patent: Aug. 10, 2004

(54) LIPOSOMAL COMPOSITIONS, AND METHODS OF USING LIPOSOMAL COMPOSITIONS TO TREAT DISLIPIDEMIAS

(75) Inventors: Wendi V. Rodrigueza, Ann Arbor, MI (US); Kevin Jon Williams, Wynnewood, PA (US); Michael J. Hope, Vancouver (CA)

(73) Assignees: Esperion LUV Development, Inc., Ann Arbor, MI (US); The University of British Columbia, Vancouver (CA)

(*) Notice: Subject to any disclaimer, the term of this patent is extended or adjusted under 35 U.S.C. 154(b) by 0 days.

(21) Appl. No.: 09/924,222

(22) Filed: Aug. 7, 2001

(65) Prior Publication Data

US 2002/0110587 A1 Aug. 15, 2002

(Under 37 CFR 1.47)

Related U.S. Application Data

(60) Continuation-in-part of application No. 09/322,336, filed on May 28, 1999, now Pat. No. 6,312,719, which is a continuation of application No. 09/175,553, filed on Oct. 20, 1998, now Pat. No. 6,139,871, which is a continuation of application No. 08/507,170, filed on Jul. 26, 1995, now abandoned, which is a continuation of application No. 08/206,415, filed on Mar. 4, 1994, now abandoned, said application No. 09/924,222, and a continuation-in-part of application No. 09/071,974, filed on May 4, 1998, now abandoned, which is a division of application No. 08/728,766, filed on Oct. 11, 1996, now Pat. No. 5,746,223.
(60) Provisional application No. 60/005,090, filed on Oct. 11, 1995.

(51) Int. Cl.[7] .......................... A61K 9/127; A61K 9/133

(52) U.S. Cl. ...................... 424/450; 428/402.2; 514/824

(58) Field of Search ...................... 424/450; 428/402.2; 514/824

(56) References Cited

U.S. PATENT DOCUMENTS

| 4,186,183 A | 1/1980 | Steck et al. |
| 4,187,180 A | 2/1980 | Joh |
| 4,217,344 A | 8/1980 | Vanlerberghe et al. |

(List continued on next page.)

FOREIGN PATENT DOCUMENTS

| DE | 40 18 767 A1 | 12/1991 |
| EP | 0 234 919 B1 | 9/1987 |
| EP | 0 461 559 B1 | 12/1991 |

(List continued on next page.)

OTHER PUBLICATIONS

The molecular basis of cancer, Ed. by P> B> Farmer & J> M. Walker, 1985, pp. 262–283.*

Adams et al. Effect of oral polyunsaturated lecithin on the development of atheroma and fatty liver in the cholesterol–fed rabbit. *J. Pathol. Bacteriol.* 1969, 97:35–41.

(List continued on next page.)

*Primary Examiner*—Gollamudi S. Kishore
(74) *Attorney, Agent, or Firm*—Jones Day

(57) ABSTRACT

The present invention provides a liposomal composition for treating dislipidemias in human subjects, a method of using a liposomal composition, and devices and modes of operation of the devices and of the compositions, and kits related thereto. The invention provides for the reverse transport of cholesterol from peripheral tissues to the liver in a warm blood mammal while controlling plasma atherogenic lipoprotein concentrations, including LDL concentrations. A method described above and mode of operation of the devices includes the stop of administering an effective amount of a multiplicity of acceptors comprised of phospholipids substantially free of sterol. A method described above optionally includes the stop of periodically assaying atherogenic lipoprotein concentrations with an assay during the treatment period to assess atherogenic lipoprotein concentrations and obtain an atherogenic lipoprotein profile.

12 Claims, 40 Drawing Sheets

U.S. PATENT DOCUMENTS

| | | | |
|---|---|---|---|
| 4,247,393 | A | 1/1981 | Wallace |
| 4,261,975 | A | 4/1981 | Fullerton et al. |
| 4,485,054 | A | 11/1984 | Mezei et al. |
| 4,532,089 | A | 7/1985 | MacDonald |
| 4,663,167 | A | 5/1987 | Lopez-Berestein et al. |
| 4,774,085 | A | 9/1988 | Fidler |
| 4,804,539 | A | 2/1989 | Guo et al. |
| 4,812,314 | A | 3/1989 | Barenholz et al. |
| 4,895,719 | A | 1/1990 | Radhakrishnan et al. |
| 4,923,439 | A | 5/1990 | Seidel |
| 4,946,787 | A | 8/1990 | Eppstein et al. |
| 4,978,654 | A | 12/1990 | Lopez-Berestein et al. |
| 5,013,556 | A | 5/1991 | Woodle et al. |
| 5,015,483 | A | 5/1991 | Haynes et al. |
| 5,077,056 | A | 12/1991 | Bally et al. |
| 5,180,366 | A | 1/1993 | Woods |
| 5,204,112 | A | 4/1993 | Hope et al. |
| 5,219,888 | A | 6/1993 | Katocs, Jr. et al. |
| 5,225,212 | A | 7/1993 | Martin et al. |
| 5,231,090 | A | 7/1993 | Hsia et al. |
| 5,250,060 | A | 10/1993 | Carbo et al. |
| 5,252,263 | A | 10/1993 | Hope et al. |
| 5,376,452 | A | 12/1994 | Hope et al. |
| 5,405,832 | A | 4/1995 | Potempa |
| 5,427,926 | A | 6/1995 | Buonassisi et al. |
| 5,489,611 | A | 2/1996 | Lee et al. |
| 5,527,538 | A | 6/1996 | Baldeschweela |
| 5,556,637 | A | 9/1996 | Hager et al. |
| 5,595,756 | A | 1/1997 | Bally et al. |
| 5,599,306 | A | 2/1997 | Klein et al. |
| 5,622,715 | A | 4/1997 | Barenholz et al. |
| 5,637,315 | A | 6/1997 | Zern et al. |
| 5,674,488 | A | 10/1997 | Reich |
| 5,705,385 | A | 1/1998 | Bally et al. |
| 5,741,514 | A | 4/1998 | Barenholz et al. |
| 5,741,517 | A | 4/1998 | Hager et al. |
| 5,753,613 | A | 5/1998 | Ansell et al. |
| 6,139,871 | A | 10/2000 | Hope et al. |
| 6,312,719 | B1 | 11/2001 | Hope et al. |

FOREIGN PATENT DOCUMENTS

| | | |
|---|---|---|
| EP | 0 470 437 | 2/1992 |
| WO | WO 86/01404 | 3/1986 |
| WO | WO 88/09345 | 12/1988 |
| WO | WO 91/17424 | 11/1991 |
| WO | WO 95/23592 | 9/1995 |

OTHER PUBLICATIONS

Adams et al. Modification of aortic atheroma and fatty liver in cholesterol–fed rabbits by intravenous injection of saturated and polyunsaturated lecithins. J. Pathol. Bacteriol 1967, 94:777–87.

Allen et al. A new strategy for attachment of antibodies to sterically stabilized liposomes resulting in efficient targeting to cancer cells. Biochim Biophys Acta. 1995 Jul 26;1237(2):99–108.

Allen, J. of Liposome Res. 1992, 2(3):289–305.

Altman et al. Phospholipids in experimental atherosclerosis. Arzneimittelforschung. 1974 Jan;24(1):11–6.

Aviram et al. Intralipid infusion abolishes ability of human serum to cholesterol–load cultured macrophages. Arteriosclerosis. 1989 Jan–Feb;9(1):67–75.

Aviram et al. Macrophage cholesterol removal by triglyceride–phospholipid emulsions. Biochem Biophys Res Commun. 1988 Sep 15;155(2):709–13.

Bally et al. Novel procedures for generating and loading liposomal systems. In *Liposomes as drug carriers: Recent Trends and Progress* (Gregoriadis G., ed.) Pp841–853, John Wiley & Sons Ltd., Chichester, England, 1988.

Bangham et al. Diffusion of univalent ions across the lamellae of swollen phospholipids. J Mol Biol. 1965 Aug;13(1):238–52.

Barclay et al. Partitioning and antioxidant action of the water–soluble antioxidant, Trolox, between the aqueous and lipid phases of phosphatidylcholine membranes: 14C tracer and product studies. Biochim Biophys Acta. 1995 Jul 6;1237(1):77–85.

Bialecki et al. Cholesterol enrichment increases basal and agonist–stimulated calcium influx in rat vascular smooth muscle cells. J Clin Invest. 1991 Dec;88(6):1894–900.

Bisgaier et al. Effects of apolipoproteins A–IV and A–I on the uptake of phospholipid liposomes by hepatocytes. J Biol Chem. 1989 Jan 15;265(2):862–6.

Bisgaier et al. Effect of lecithin: cholesterol acyltransferase on distribution of apolipoprotein A–IV among lipoproteins of human plasma. J Lipid Res. 1987 Jun;28(6):693–703.

Blaton et al. The human plasma lipids and liproteins under influence of EPL–therapy. In *Phosphatidylcholine* (Peters, H., ed.) pp 125–132, Springer–Verlag: Berlin, 1976.

Bligh et al. A rapid method of total lipid extraction and purification. Can. J. Biochem. Physiol. 1959; 37:911–917.

Bloomfield VA. Quasi–elastic light scattering applications in biochemistry and biology. Annu Rev Biophys Bioeng. 1981;10:421–50. Review.

Bottger G, Strik W. [Fat embolism] Munch Med Wochenschr. 1970 Jan 9;112(2):51–8. German.

Byers et al. Effect of infusions of phosphatides upon the atherrosclerosis aorta in situ and as an ocular aortic implant. J. Lipid Res. 1960; 1:343–349.

Campanacci et al. Response of plasma lipid fractions to the administration of exogenous phospholipids. Arzneimittelforschung. 1975 Aug;25; (8):1306–8.

Chakrabarti et al. Influence of charge, charge distribution, and hydrophobicity on the transport of short model peptides into liposomes in response to transmembrane pH gradients. Biochemistry. 1994 Jul 19;33(28):8479–85.

Chisolm et al. Antioxidants and Atherosclerosis: A Current Assessment. Clin. Cardiol. 1991; 14:25–30.

Ciammaichella et al. Polyunsaturated phosphatidyl choline (EPL) in the treatment of cerebral arteriosclerosis and arteriosclerosis of the lower extremities. Clin Ter. 1975 Jul 15; 74(1):55–62. Italian.

Constantinides et al. Production of advanced cholesterol atherosclerosis in the rabbit. Arch. Pathol. 1961; 70:81–102.

Daida et al. Prevention of restenosis after percutaneous transluminal coronary angioplasty by reducing lipoprotein (a) levels with low–density lipoprotein apheresis. Low–Density Lipoprotein Apheresis Angioplasty Restenosis Trial (L–ART) Group. Am J Cardiol. 1994 Jun 1;73(15):1037–40.

Davidson et al. The effect of high density lipoprotein phospholipid acyl chain composition on the efflux of cellular free cholesterol. J Biol Chem. 1995 Mar 17;270(11):5882–90.

Davidson et al. Association and release of prostaglandin E1 from liposomes. Biochim Biophys Acta. 1997 Jul 5;1327(1):97–106.

De Caterina R & Lenzi S. Prevention and therapy of vascular damage and endothelial dysfunction with hypocholesteremic agents. G Ital Cardiol. 1998 Feb;28(2):168–77. Review. Italian.

Deamer et al. Large volume liposomes by an ether vaporization method. Biochim Biophys Acta. 1976 Sep 7;443(3):629–34.

Desmarais et al. Elevated serum lipoprotein(a) is a risk factor for clinical recurrence after coronary balloon angioplasty. Circulation. 1995 Mar 1; 91(5):1403–9.

Dewailly et al. Plasma removal of intravenous essential phospholipids in man. In *Phosphatidylcholine*. Peeters ed. Berlin: Springer, 1976.

Ellens et al. In vivo fate of large unilamellar sphingomyelin–cholesterol liposomes after intraperitoneal and intravenous injection into rats. Biochim Biophys Acta. 1981 Apr 17; 674(1):10–8.

Ely KR, Firca JR, Williams KJ, Abola EE, Fenton JM, Schiffer M, Panagiotopoulos NC, Edmundson AB.Crystal properties as indicators of conformational changes during ligand binding or interconversion of Mcg light chain isomers. Biochemistry. 1978 Jan 10; 17(1):158–67.

Farnier & Davignon, Current and future treatment of hyperlipidemia: the role of statins. Am J Cardiol. 1998 Aug 27;82(4B):3J–10J. Review.

Fiske et al. The colorimetric determination of phosphorus. J. Biol. Chem. 1925; 66:375–400.

Fraley et al. Entrapment of a bacterial plasmid in phospholipid vesicles: potential for gene transfer. Proc Natl Acad Sci U S A. 1979 Jul;76(7):3348–52.

Friedman et al. Resolution of aortic atherosclerosis infiltration in the rabbit by phosphatide infusion. Proc. Soc. Exp. Biol. Med., 1957, 95:586–588.

Gould KL. New concepts and paradigms in cardiovascular medicine: the noninvasive management of coronary artery disease. Am J Med. 1998 Jun 22;104(6A):2S–17S. Review.

Gregoriadis et al. Liposomes in vivo: A relationship between stability and clearance? In *Targeting of Drugs with Synthetic Systems* (Gregoriadis et al. Eds.), pp183–192, Plenum Press, New York, 1985.

Griffin et al. Appearance and characterization of lipoprotein X during continuous intralipid infusions in the neonate J Clin Invest. 1979 Dec;64(6):1703–12.

Groop et al. Lipoprotein(a) in type 1 diabetic patients with renal disease. Diabet Med. 1994 Dec;11(10):961.

Gwynne HDL and atherosclerosis: An update. Clin. Cardiol. 1991, 14:17–24.

Hernandez–Perera et al. Effects of the 3–hydroxy–3–methylglutaryl–CoA reductase inhibitors, atorvastatin and simvastatin, on the expression of endothelin–1 and endothelial nitric oxide synthase in vascular endothelial cells. J Clin Invest. 1998 Jun 15:101(12):2711–9.

Holman et al. Technics for studying atherosclerosis lesions. Lab. Invest. 1958, 7:42–47.

Hope et al. Generation of multilamellar and unilamellar phospholipid vesicles. Chem. Phys. Lipids; 1986, 40:89–107.

Hope et al. Production of large unilamellar vesicles by a rapid extrusion procedure. Characterization of size distribution, trapped volume and ability to maintain a membrane potential. Biochim. Biophys. Acta. 1985, 812:55–65.

Horan et al. Kinetic evaluation of lipophilic inhibitors of lipid peroxidation in DLPC liposomes. Free Radic Biol Med. 1994 Dec;17(6):587–96.

Hosoda et al. Antitumor activity of doxorubicin encapsulated in poly(ethylene glycol)–coated liposomes. Biol Pharm Bull. 1995 Sep;18(9):1234–7.

Howard et al. Atherosclerosis induced in hypercholesterolaemic baboons by immunological injury; and the effects of intravenous polyunsaturated phosphatidyl choline. Atherosclerosis. 1971 Jul–Aug;14(1):17–29.

Isele et al. Pharmacokinetics and body distribution of liposomal zinc phthalocyanine in tumor–bearing mice: influence of aggregation state, particle size, and composition. J Pharm Sci. 1995 Feb;84(2):166–73.

Kobashigawa et al. Effect of pravastatin on outcomes after cardiac transplantation. N Engl J Med. 1995 Sep 7;333(10):621–7.

Koga et al. Hepatic "intravenous fat pigment" in infants and children receiving lipid emulsion. J. Pediatr. Surg. 1975, 10:641–648.

Kokoglu et al. Elevated serum Lp(a) levels in the early and advanced stages of breast cancer. Cancer Biochem Biophys. 1994 Sep;14(2):133–6.

Krack et al. Intraperitoneal administration of phosphatidylcholine improves ultrafiltration in continuous ambulatory peritoneal dialysis patients. Perit Dial Int. 1992;12(4):359–64.

Krupp et al. The in vivo transformation of phospholipid vesicles to a particle resembling HDL in the rat. Biochem Biophys Res Commun. 1976 Oct 18;72(4):1251–8.

Kuriyama et al. Low levels of serum apolipoprotein A I and A II in senile dementia. Jpn J Psychiatry Neurol. 1994 Sep;48(3):589–93.

Law D.H., Total parenteral nutrition. N. Engl. J. Med. 1977, 297:1104–1107.

Lenzo et al. Effects of phospholipid composition on the metabolism of triacylglycerol, cholesteryl ester and phosphatidylcholine from lipid emulsions injected intravenously in rats. Biochim Biophys Acta. 1988 May 2;960(1):111–8.

Liebler DC, Burr JA. Antioxidant stoichiometry and the oxidative fate of vitamin E in peroxyl radical scavenging reactions. Lipids. 1995 Sep;30(9):789–93.

Liu et al. pH–sensitive, plasma–stable liposomes with relatively prolonged residence in circulation. Biochim Biophys Acta. 1990 Mar;1022(3):348–54.

Luscher et al. Lipids and endothelial function: effects of lipid–lowering and other therapeutic interventions. Curr Opin Lipidol. 1996 Aug;7(4):234–40. Review.

Massey et al. Fluoresence assay of the specificity of human plasma and bovine liver phospholipid transfer proteins. Biochim Biophys Acta. 1985 Jun 14;835(1):124–31.

Mauk et al. Stability of lipid vesicles in tissues of the mouse: a gamma–ray perturbed angular correlation study. Proc Natl Acad Sci U S A. 1979 Feb;76(2):765–9.

Maurukas et al. Treatment of experimental atherosclerosis in the rabbit with L, D. alpha (dimyristoyl) lecithin. J. Lab. Clin. Med., 1960, 56:30–37.

Mayer et al. Vesicles of variable sizes produced by a rapid extrusion procedure. Biochim Biophys Acta. 1986 Jun 13;858(1):161–8.

Mendez et al. Interaction of rabbit lipoproteins and red blood cells with liposomes of egg yolk phospholipids. Lipids. 1988 Oct;23(10):961–7.

Mercadal et al. N–palmitoylphosphatidylethanolamine stabilizes liposomes in the presence of human serum: effect of lipidic composition and system characterization. Biochim Biophys Acta. 1995 May 4;1235(2):281–8.

Mihail et al. The coronary syndrome in two cases of essential familial hypercholesterolemia (the therapeutic effect of polyene–phosphatidyl–choline). Rev. Roum. Med. Intern., 1973, 10:255–233.

Miyazaki et al. Acetylated low density lipoprotein reduces its ligand activity for the scavenger receptor after interaction with reconstituted high density lipoprotein. J Biol Chem. 1994 Feb 18;269(7):5264–9.

Moghimi & Patel Tissue specific opsonins for phagocytic cells and their different affinity for cholesterol–rich liposomes. FEBS Lett. 1988 Jun 6;233(1):143–7.

Nayar et al. Generation of large unilamellar vesicles from long–chain saturated phosphatidylcholines by extrusion technique. Biochim. Biophys. Acta, 1989, 986:200–206.

Oto et al. Poly(methacrylic acid)–induced liposome aggregation for measuring drug entrapment. Anal Biochem. 1995 Jul 20;229(1):106–11.

Patelski et al. Modification of enzyme activities in experimental atherosclerosis in the rabbit. Atherosclerosis 1970, 12:41–53.

Pearson TA, Dillman J, Williams KJ, Wolff JA, Adams R, Solez K, Heptinstall RH, Malmros H, Sternby N. Clonal characteristics of experimentally induced "atherosclerosis" lesions in the hybrid hare. Science. 1979 Dec 21;206(4425):1423–5.

Phillips et al. Mechanisms and consequences of cellular cholesterol exchange and transfer. Biochim Biophys Acta. 1987 Jun 24;906(2):223–76.

Plane e tal. Oxidative modification of low–density lipoproteins and the inhibition of relaxations mediated by endothelium–derived nitric oxide in rabbit aorta. Br J Pharmacol. 1992 Jan;105(1):216–22.

Prior et al. The hypercholesteremic rabbit. Arch. Path., 1961, 71:82–94.

Rajakumar et al. Antioxidant properties of phenyl styryl ketones. Free Radic Res. 1995 Apr;22(4):309–17.

Ravid et al. Main risk factors for nephropathy in type 2 diabetes mellitus are plasma cholesterol levels, mean blood pressure, and hyperglycemia. Arch Intern Med. 1998 May 11;158(9):998–1004.

Redgrave et al. Effects of sphingomyelin and phosphatidylcholine acyl chains on the clearance of triacylglycerol–rich lipoproteins from plasma. Studies with lipid emulsions in rats. Biochim Biophys Acta. 1992 Jun 5;1126(1):65–72.

Reynolds GA. Rational therapy of familial hypercholesterolemia. Circulation. 1989 May;79(5):1146–8.

Rodrigueza et al. The influence of size and composition on the cholesterol mobilizing properties of liposomes in vivo. Biochim Biophys Acta. 1993 Nov 21;1153(1):9–19.

Rodrigueza et al. Structural and metabolic consequences of liposomes–lipoprotein interactions. *Advanced Drug Delivery Reviews*. 32:31–43, 1998.

Rodrigueza et al. Large versus small unilamellar vesicles mediated reverse cholesterol transport in vivo into two distinct hepatic metabolic pools. Implications for the treatment of atherosclerosis. Arterioscler Thromb Vasc Biol. 1997 Oct;17(10):2132–9.

Rodrigueza et al. Cholesterol mobilization and regression of atheroma in cholesterol–fed rabbits induced by large unilamellar vesicles. Biochim Biophys Acta. 1998 Jan 19;1368(2):306–20.

Rose et al. Improved procedure for the extraction of lipids from human erythrocytes. J. Lipid Res. 1965, 6:428–431.

Rosenfeld et al. Lipid composition of aorta of Watanabe heritable hyperlipemic and comparably hypercholesterolemic fat–fed rabbits. Plasma lipid composition determines aortic lipid composition of hypercholesterolemic rabbits. Arteriosclerosis. 1988 Jul–Aug;8(4):338–47.

Rudell et al. Determination of cholesterol using o–phthaladehyde. J. Lipid Res. 1973, 14:364–366.

Sachs et al. In vivo effects of inositol phosphatide (Lipositol) in serum lipids and atherosclerosis of hyperlipemic rabbits. J. Appl. Physiol. 1960, 15:983–986.

Sahni et al. Prevention of restenosis by lovastatin after successful coronary angioplasty. Am Heart J. 1991 Jun;121(6 Pt 1):1600–8.

Schenk et al. Studies on sucrose–palmitate–stearate–containing vesicles encapsulating the cytostatic drug methylgloxal–bis–guanyl–hydrazone. Pharmazie. 1990 Oct;45(10):747–9.

Scherphof et al. Disintegration of phosphatidylcholine liposomes in plasma as a result of interaction with high–density lipoproteins. Biochim Biophys Acta. 1978 Aug 17;542(2):296–307.

Schmeeda et al. Cholesterol distribution in rat heart myosytes. Am. J. Physiol. 1995, 268:H759–H766.

Schmidt et al. High–density lipoprotein antagonizes the inhibitory effects of oxidized low–density lipoprotein and lysolecithin on soluble guanylyl cyclase. Biochem Biophys Res Commun. 1992 Jan 15;182(1):302–8.

Schroeder et al. Membrane cholesterol dynamics: cholesterol domains and kinetic pools. Proc Soc Exp Biol Med. 1991 Mar;196(3):235–52. Review.

Schuber et al. Polyamines as modulators of membrane fusion: aggregation and fusion of liposomes. Biochemistry. 1983 Dec 20;22(26):6134–40.

Schumaker et al. Sequential flotation ultracentrifugation. Methods Enzymol. 1986;128:155–70.

Senior et al. Tissue distribution of liposomes exhibiting long half–lives in the circulation after intravenous injection. Biochim Biophys Acta. 1985 Mar 29;839(1):1–8.

Slotte JP. Lateral domain formation in mixed monolayers containing cholesterol and dipalmitoylphosphatidylcholine or N–palmitoylsphingomyelin. Biochim Biophys Acta. 1995 May 4;1235(2):419–27.

Small DM. George Lyman Duff memorial lecture. Progression and regression of atherosclerotic lesions. Insights from lipid physical biochemistry. Arteriosclerosis. 1988 Mar–Apr;8(2):103–29.

Soloviev et al. Phospholipid vesicles (liposomes) restore endothelium–dependent cholinergic relaxation in thoracic aorta from spontaneously hypertensive rats. J Hypertens. 1993 Jun;11(6):623–7.

Sparks et al. The charge and structural stability of apolipoprotein A–I in discoidal and spherical recombinant high density lipoprotein particles. J Biol Chem. 1992 Dec 25;267(36):25839–47.

Sparks et al. Effect of cholesterol on the charge and structure of apolipoprotein A–I in recombinant high density lipoprotein particles. J Biol Chem. 1993 Nov 5;268(31):23250–7.

St Clair RW. Atherosclerosis regression in animal models: current concepts of cellular and biochemical mechanisms. Prog Cardiovasc Dis. 1983 Sep–Oct;26(2):109–32. Review.

Stafford et al. Regression of atherosclerosis effected by intravenous phospholipid. Artery, 1975, 1:106–114.

Stroes et al. Vascular function in the forearm of hypercholesterolaemic patients off and on lipid–lowering medication. Lancet. 1995 Aug 19:346(8973);467–71.

Stuart et al. Effect of cholesterol on production of thromboxane 62 by platelets in vitro. N Engl J Med. 1980 Jan 3;302(1):6–1.

Sugiyama et al. Lipoproteins regulate C–type natriuretic peptide secretion from cultured vascular endothelial cells. Arterioscler Thromb Vasc Biol. 1995 Nov;15(11):1968–74.

Sugiyama et al. Approaches that mitigate doxorubicin–induced delayed adverse effects on mitochondrial function in rat hearts; liposome–encapsulated doxorubicin or combination therapy with antioxidant. Biochem Mol Biol Int. 1995 Aug;36(5):1001–7.

Suzuki et al. Preparation of long–circulating immunoliposomes containing adriamycin by a novel method to coat immunoliposomes with poly(ethylene glycol). Biochim Biophys Acta. 1995 Aug 17;1245(1):9–16.

Tabas I, Li Y, Brocia RW, Xu SW, Swenson TL, Williams KJ. Lipoprotein lipase and sphingomyelinase synergistically enhance the association of atherogenic lipoproteins with smooth muscle cells and extracellular matrix. A possible mechanism for low density lipoprotein and lipoprotein(a) retention and macrophage foam cell formation. J Biol Chem. 1993 Sep 25;268(27):20419–32.

Takahashi et al. Increased concentrations of serum Lp(a) lipoprotein in patients with primary gout. Ann Rheum Dis. 1995 Feb;54(2):90–3.

Tall et al. Accelerated transfer of cholesteryl esters in dyslipidemic plasma. Role of cholesteryl ester transfer protein. J Clin Invest. 1987 Apr;79(4):1217–25.

Tall et al. Lipoprotein–liposome interactions. Methods Enzymol. 1986;128:647–57.

Tenda et al. The relationship between serum lipoprotein(a) and restenosis after initial elective percutaneous transluminal coronary angioplasty. Jpn Circ J. 1993 Aug;57(8):789–95.

Thompson et al. Effects of intravenous phospholipid on low density lipoprotein turnover in man. Eur J Clin Invest. 1976 Jun 21;6(3):241–8.

Thompson et al. Contrasting effects on plasma lipoproteins of intravenous versus oral administration of a triglyceride–phospholipid emulsion. Eur. J. Clin. Invest. 1975, 5:373–384.

Torchilin et al. New synthetic amphilphilic polymers for steric protection of liposomes in vivo. J Pharm Sci. 1995 Sep;84(9):1049–53.

Tricerri et al. Conformation of apolipoprotein AI in reconstituted lipoprotein particles and particle–membrane interaction: effect of cholesterol. Biochim Biophys Acta. 1998 Mar 6;1391(1):67–78.

Untracht SH. Intravascular metabolism of an artificial transporter of triacylglycerols. Alterations of serum lipoproteins resulting from total parenteral nutrition with Intralipid. Biochim Biophys Acta. 1982 Apr 15;711(1):176–92.

van den Boom et al. In vivo turnover of phospholipids in rabbit erythrocytes. Biochim Biophys Acta. 1994 Dec 8;1215(3):314–20.

Waligora et al. Effect of a hypercholesterolaemic diet and single injection of polyunsaturated phosphatidyl choline solution on the activities of lipolytic enzymes, acyl–CoA synthetase and acyl–CoA cholesterol acyl–transferase in rabbit tissues. Biochem Pharmacol. 1975 Dec 15;24(24):2263–7.

Williams, Q. and Williams, K.J. , Leakage from vitrified radioactive waste. *Lancet* 337:791, 1991.

Williams et al. Mechanisms by which lipoprotein lipase alters cellular metabolism of lipoprotein(a), low density lipoprotein, and nascent lipoproteins. Roles for low density lipoprotein receptors and heparan sulfate proteoglycans. J Biol Chem. 1992 Jul 5;267(19):13284–92.

Williams, K.J. Fast–lane learning. *Science News* 138:339, 1990.

Williams et al. Intravenously administered lecithin liposomes: a synthetic antiatherogenic lipid particle. Perspect Biol Med. 1984 Spring;27(3):417–31. Review.

Williams et al. The unstirred water layer as a site of control of apolipoprotein B secretion. J Biol Chem. 1990 Oct 5;265(28):16741–4.

Williams, K.J. Dust wars. *Bull. Atomic. Sci.* 42:56, 1986.

Williams, K.J. Riled over reading. *Science News*. 141:227&238, 1992.

Williams et al. Low density lipoprotein receptor–independent hepatic uptake of a synthetic, cholesterol–scavenging lipoprotein: implications for the treatment of receptor–deficient atherosclerosis. Proc Natl Acad Sci U S A. 1988 Jan;85(1):242–6.

Williams et al. Uptake of endogenous cholesterol by a synthetic lipoprotein. Biochim Biophys Acta. 1986 Feb 12;875(2):183–94.

Williams KJ, Tabas I. The response–to–retention hypothesis of early atherogenesis. Arterioscler Thromb Vasc Biol. 1995 May;15(5):551–61. Review.

Williams, K. J. The reader' NIH. *Science* 258:532, 1992.

Williams et al. An analysis of the resident match. N Engl J Med. 1981 May 7;304(19):1165–6.

Williams, K. J. et al. National Resident Matching Program. *N. Engl. J. Med.* 305:526, 1981.

Williams KJ. A reexamination of the NRMP matching algorithm. National Resident Matching Program. Acad Med. 1995 Jun;70(6):470–6; discussion 490–4. Review.

Williams, KJ., Comments on Peranson and Randlett's. The NRMP matching algorithm revisted: theory versus practice. Acad. Med. 70:485–489, 1995.

Williams et al. Phospholipid liposomes acquire apolipoprotein E in atherogenic plasma and block cholesterol loading of cultured macrophages. J Clin Invest. 1987 May;79(5):1466–72.

Williams et al. Recognition of vesicular lipoproteins by the apolipoprotein B,E receptor of cultured fibroblasts. J Lipid Res. 1986 Aug;27(8):892–900.

* cited by examiner

LUV-SUV #2

Hepatic mRNA content (pg/ug)

| Rabbit # | Treatment | CETP | HMG-CoA R | LDLR | 7α-hydroxylase | LDL ChE, day 1 | LDL ChE, day 3 | LDL ChE, day 5 | LDL ChE, day 6 |
|---|---|---|---|---|---|---|---|---|---|
| 1 | (A) PBS | 2.87 | 0.54 | 4.27 | 0.56 | 7.4 | 7.1 | 5.2 | 6.5 |
| 2 | (A) PBS | 5.63 | 0.55 | 5.38 | 0.39 | 18.1 | 11.8 | 6.2 | 9.7 |
| 3 | (A) PBS | 5.34 | 0.39 | 8.93 | 0.74 | 8.5 | 8.9 | 4.4 | 8.7 |
| 4 | (A) PBS | 5.04 | 0.55 | 5.49 | 0.82 | 14.1 | 14.1 | 6.8 | 8.6 |
|  | Mean | 4.72 | 0.51 | 6.02 | 0.63 | 11.53 | 10.48 | 6.15 | 8.38 |
|  | SEM | 0.63 | 0.04 | 1.01 | 0.10 | 2.12 | 1.55 | 0.98 | 0.67 |
| 5 | (B) LUV | 3.15 | 0.58 | 7.23 | 0.63 | 25.3 | 14.9 | 13.6 | 10.5 |
| 6 | (B) LUV | 3.02 | 0.47 | 8.15 | 0.58 | 14.0 | 15.9 | 10.8 | 8.2 |
| 7 | (B) LUV | 2.52 | 0.58 | 4.81 | 0.83 | 28.3 | 22.5 | 21.3 | 22.4 |
| 8 | (B) LUV | 2.68 | 0.58 | 7.37 | 0.94 | 17.5 | 21.8 | 13.4 | 9.5 |
|  | Mean | 2.84 | 0.55 | 6.89 | 0.75 | 21.28 | 16.78 | 14.78 | 12.85 |
|  | SEM | 0.15 | 0.03 | 0.72 | 0.08 | 3.33 | 1.96 | 2.27 | 3.28 |
|  | t vs. PBS | 2.910 | 0.939 | 0.703 | 0.919 | 2.473 | 3.318 | 3.506 | 1.275 |
| 13 | SUV + LUV | 3.18 | 0.50 | 5.28 | 0.51 | 11.9 | 34.0 | 20.1 | 22.2 |
| 10 | (C) SUV | 5.64 | 0.38 | 3.98 | 0.30 | 21.1 | 45.3 | 15.3 | 46.3 |
| 11 | (C) SUV | 3.39 | 0.29 | 3.67 | 0.42 | 10.0 | 36.3 | 59.6 | 42.7 |
| 12 | (C) SUV | 3.00 | 0.13 | 3.34 | 0.63 | 17.8 | 31.8 | 45.5 | 22.3 |
|  | Mean w/o #13 | 4.01 | 0.27 | 3.66 | 0.45 | 16.30 | 37.80 | 40.13 | 37.10 |
|  | SEM w/o #13 | 0.02 | 0.07 | 0.18 | 0.10 | 3.28 | 3.97 | 13.07 | 7.47 |
|  | t vs. PBS | 0.686 | 2.903 | 2.295 | 1.304 | 1.220 | 6.414 | 2.594 | 3.628 |
|  | t vs. LUV | 1.397 | 3.660 | 4.328 | 2.301 | 1.963 | 4.296 | 1.912 | 2.98 |
|  | Mean w/ #13 | 3.80 | 0.33 | 4.07 | 0.47 | 15.20 | 38.86 | 35.13 | 33.38 |
|  | SEM w/ #13 | 0.62 | 0.06 | 0.42 | 0.07 | 2.57 | 2.96 | 10.51 | 8.48 |
|  | t vs. PBS | 1.041 | 2.091 | 1.781 | 1.369 | 1.103 | 7.890 | 2.748 | 3.848 |
|  | t vs. LUV | 1.512 | 2.763 | 3.369 | 2.554 | 1.445 | 8.085 | 1.893 | 2.856 |

FIG. 2

*Indicates column of interest

Key points about LUV and atherosclerosis

1) Practical: Straight forward to manufacture

Non-toxic at very high doses

2) Mechanistic: Liposomes promote reverse cholesterol transport *in vivo*

LUV are the optimal preparation

FIG. 9

- Effectiveness in humans

- Therapeutic targets

Lipid-rich, rupture-prone plaques
    Critical Stenosis
    Post-angioplasty re-stenosis
    Atherosclerosis in general

FIG. 18

LIPOSOMAL COMPOSITIONS, AND METHODS OF USING LIPOSOMAL COMPOSITIONS TO TREAT DISLIPIDEMIAS

CONTINUING DATA AND PRIORITY CLAIM

This application is a continuation-in-part of U.S. patent application Ser. No. 09/322,336, filed May 28, 1999, now U.S. Pat. No. 6,312,719, which is a continuation of U.S. patent application Ser. No. 09/175,553 filed Oct. 20, 1998, now U.S. Pat. No. 6,139,871, which is a continuation of U.S. patent application Ser. No. 08/507,170 filed Jul. 26, 1995, abandoned, which is a continuation of U.S. patent application Ser. No. 08/206,415 filed Mar. 4, 1994, abandoned, each of which is incorporated herein by reference in their entirety. This application is also a continuation-in-part of U.S. patent application Ser. No. 09/071,974, filed May 4, 1998 now abandoned, which is a divisional of U.S. patent application Ser. No. 08/728,766, filed Oct. 11, 1996, now U.S. Pat. No. 5,746,223, which claims the benefit of priority to U.S. Provisional Patent Application No. 60/005,090 filed Oct. 11, 1995, each of which is incorporated herein by reference in their entirety.

BACKGROUND OF THE INVENTION

Several human conditions are characterized by distinctive lipid compositions of tissues, cells, membranes, and extracellular regions or structures. For example, in atherosclerosis, cholesterol (unesterified, esterified, and oxidized forms) and other lipids accumulate in cells and in extracellular areas of the arterial wall and elsewhere. These lipids have potentially harmful biologic effects, for example, by changing cellular functions, including gene expression, and by narrowing the vessel lumen, obstructing the flow of blood. Removal of these lipids would provide numerous substantial benefits. Moreover, cells, membranes, tissues, and extracellular structures will benefit in general from compositional alterations that include increasing resistance to oxidation and oxidative damage, such as by increasing the content and types of anti-oxidants, removing oxidized material, and increasing the content of material that is resistant to oxidation. In aging, cells have been shown to accumulate sphingomyelin and cholesterol, which alter cellular functions. These functions can be restored in vitro by removal of these lipids and replacement with phospholipid from liposomes. A major obstacle to performing similar lipid alterations in vivo has been disposition of the lipids mobilized from tissues, cells, extracellular areas, and membranes. Natural (e.g., high-density lipoproteins) and synthetic (e.g., small liposomes) particles that could mobilize peripheral tissue lipids have a substantial disadvantage: they deliver their lipids to the liver in a manner that disturbs hepatic cholesterol homeostasis, resulting in elevations in plasma concentrations of harmful lipoproteins, such as low-density lipoprotein (LDL), a major atherogenic lipoprotein. There exist a need for a better method to manipulate the lipid content and composition of peripheral tissues, cells, membranes, and extracellular regions in vivo.

The intravenous administration of cholesterol-poor phospholipid vesicles (liposomes) or other particles that transport cholesterol and other exchangeable material from lipoproteins and peripheral tissues, including atherosclerotic arterial lesions, to the liver produces substantial derangements of hepatic cholesterol homeostasis, such as enhanced hepatic secretion of apolipoprotein-B, and suppression of hepatic LDL receptors. The hepatic derangements lead to increase plasma concentrations of LDL and other atherogenic lipoproteins. Increased concentrations of LDL or other atherogenic lipoproteins will accelerate, not retard, the development of vascular complications. Deranged hepatic cholesterol homeostasis can also be manifested by abnormal regulation of genes, such as a gene for the LDL receptor, a gene for HMG-CoA reductase, a gene for cholesterol 7-alpha hydroxylase, and a gene regulating a function involved in cholesterol homeostasis. There exists a need for methods and compounds that can produce a removal of cholesterol and other exchangeable material, from peripheral cells, tissues, organs, and extracellular regions, and that can produce a delivery of material, such as phospholipids, to cells, tissues, or organs, extracellular regions without harmfully disrupting hepatic cholesterol homeostasis and plasma concentrations of atherogenic lipoproteins.

By way of example, atherosclerosis, a major killer in Western countries, is characterized by the accumulation of cholesterol and cholesteryl ester in cells and in extracellular areas of the arterial wall and elsewhere. There exists a need for a better method to manipulate the lipid content and composition of peripheral tissues, cells, membranes, and extracellular regions in vivo. There further exists a need for methods or compounds that can produce removal of cholesterol from cellular and extracellular regions of arteries, but without provoking a rise in the plasma concentration of LDL.

The invention described herein provides methods and compositions related to the removal of cholesterol from arteries, whole controlling plasma concentrations of LDL. The present invention addresses these needs so that diseases and detrimental medical conditions can be treated, controlled or eliminated.

This invention provides methods and compositions that relate to the "reverse" transport of lipids and other exchangeable material from peripheral tissues to the liver in vivo while controlling plasma LDL concentrations. There exists a need for a method of, treatment, and a pharmaceutical composition for forcing the reverse transport of lipids from peripheral tissues to the liver in vivo while controlling plasma LDL concentrations; of regulating hepatic parenchymal cell cholesterol content and metabolism in a cell having at least one gene selected from the group consisting of a gene for an LDL receptor, a gene for HMG-CoA reductase, a gene for cholesterol 7-alpha-hydroxylase, and a gene regulating a function involved in cholesterol homeostasis; and, homeostasis thereof; suppressing hepatic expression of a cholesterol ester transfer protein gene in vivo, whereby plasma LDL and HDL are controlled as a result of the administration; suppressing the rise in plasma LDL concentrations after administration of an agent having small acceptors of cholesterol or other lipids; of diagnosing a side-effect of reverse transport of cholesterol from peripheral tissues to the liver in vivo accompanying parenteral administration of a multiplicity of large liposomes and small liposomes during a treatment period, whereby a side effect of administration of the liposomes is diagnosed and effectively regulated; and, diagnosing and treating a side-effect of reverse transport of lipids from peripheral tissues to the liver in vivo accompanying parenteral administration of a multiplicity of large liposomes and small liposomes during a treatment period. There further exists a need for a system in which patients will have a decreased risk of developing atherosclerosis and/or cellular changes from aging; an improved method of reducing the lipid content of lesions.

The invention described herein provides methods and compositions related to the removal of cholesterol and other exchangeable material from peripheral tissues, and otherwise altering peripheral tissue lipids, while controlling plasma concentrations of LDL and other atherogenic lipoproteins and avoiding harmful disruptions of hepatic cholesterol homeostasis. Specific genes in both the peripheral tissues and in the liver are controlled by these methods and compositions. There exists a need for better methods to manipulate the lipid content and composition of peripheral tissues, cells, membranes, and extracellular regions in vivo, particularly in regard to diseases and processes involving oxidation and oxidative damage. Moreover, currently available artificial particles for intravenous administration contain significant amounts of oxidized material (Helbock et al. Pediatrics 91:83–87, 1993), which contributes to their unsuitability for these purposes.

There further exists a need for methods or compounds that can produce a removal of cholesterol and other exchangeable material, including oxidized materials, from peripheral cells, tissues, organs, and extracellular regions, and that can produce a delivery of anti-oxidants to cells, tissues, organs, and extracellular regions, but without harmfully disrupting hepatic cholesterol homeostasis, including hepatic gene expression and regulation.

The invention described herein provides methods and compositions related to the removal of cholesterol and other exchangeable material from peripheral tissues, and otherwise altering peripheral tissue composition, to reduce or avoid oxidation and its effects and products, while controlling plasma concentrations of LDL and other atherogenic lipoproteins and avoiding harmful disruption of hepatic cholesterol homeostasis. It is an object of the invention of the present invention to solve the problems articulated above and other problems in the art.

Renal failure, both acute and chronic, is a major health problem. Current treatments for these conditions include hemodialysis, peritoneal dialysis, rectal dialysis, renal transplantation, and treatment of the underlying renal disease when possible. A major, widely recognized drawback to all methods of treatment of renal failure is accelerated atherosclerosis, which leads to heart attacks, strokes, claudication, and many other complications. Renal patients also undergo accelerated aging. There exists a need to reduce or eliminate atherosclerosis in patients with renal failure and reduce the rate of aging. These specific complications are treated with lipid-lowering drugs, LDL apheresis, angioplasty, coronary bypass surgery, carotid endarterectomy, other vascular reconstructive surgery, heart transplantation, and restoration of renal function when possible. Nevertheless, these methods are at best only partially effective and are often extremely invasive. There exists a need for a simple, effective, non-invasive or minimally invasive approach to reduce atherosclerosis or slow its development in patients with renal disease.

The intravenous administration of cholesterol-poor phospholipid vesicles (liposomes) or other particles to transport cholesterol from peripheral tissues, including atherosclerotic arterial lesions, to the liver produces substantial derangements in hepatic cholesterol homeostasis, such as enhanced hepatic secretion of apolipoprotein-B, the major protein of atherogenic lipoproteins, and suppression of hepatic LDL receptors (see, for example, Spady et al. J. Lipid Res. 26:465–472, 1985; Williams et al. Proc. Natl. Acad. Sci. USA 85:242–246, 1988; Williams et al. J. Biol. Chem. 265:16741–16744, 1990; Dixon & Ginsberg J. Lipid Res. 34:167–179, 1993; Tanka et al. Atherosclerosis 114:73–82, 1995; and citations therein). The hepatic derangements lead to increased plasma concentrations of LDL and other atherogenic lipoproteins. Increased concentrations of LDL or other atherogenic lipoprotein will accelerate, not retard, the development of vascular complications. Deranged hepatic cholesterol homeostasis can also be manifested by abnormal regulation of other genes, such as a gene for the LDL receptor, a gent for HMG-CoA reductase, a gender for cholesterol 7-alpha hydroxylade, and a gene regulating a function involved in cholesterol homeostasis. There exists a need for methods or compounds that can produce a removal of cholesterol and other exchangable material from peripheral cells, tissues, organs, and extracellular regions, but without harmfully disrupting hepatic cholesterol homeostasis.

The invention described herein provides methods a compositions related to the removal of cholesterol and other lipids from peripheral tissues, and otherwise altering peripheral tissue lipids, in patients with renal disease, while controlling plasma concentrations of LDL and other atherogenic lipoproteins and avoiding harmful disruptions of hepatic cholesterol homeostasis.

The present invention provides pharmaceutical compositions and methods useful for the treatment of atherosclerosis. More particularly, the compositions generally comprise liposomes having an average diameter of about 100–150 nanometers and a pharmaceutically acceptable carrier. The methods generally comprise administering such compositions.

Atherosclerosis is the leading cause of death in the United States. Atherosclerosis is the formation of plaques in arterial walls that can occlude the vessel lumen and obstruct blood flow through the vessel. Morbidity and mortality generally occur through end organ damage and organ dysfunction resulting from ischemia. The most common forms of ischemia that end in organ damage are myocardial infarction and cerebrovascular accidents. Disability or death often result from these vascular events. There exists a need in the art to treat these types of ischemia, and it is an object of the invention to treat different types of ischemia.

Even atherosclerosis-related ischemia that does not permanently injure myocardium is responsible for significant morbidity in the form of angina pectoris and congestive heart failure. Other organs, such as the kidneys, the intestines, and the spinal cord, may also be injured by atherosclerotic occlusions. Further, in diseases such as aortic aneurysms, atherosclerotic arteries may cause clinical symptoms independent of end organ dysfunction.

Arteriosclerotic lesions are plaques that form by accumulation of cholesterol, cholesterol esters, and phosphplipids and proliferation of smooth muscle cells in the intima of major arteries. Lipid contributes a major portion of the plaque volume (generally 30–65% dry weight). Small, Arteriosclerosis, 8:103–129 (1988). In fact, the risk of developing arteriosclerosis is directly related to the concentration of certain forms of plasma cholesterol. Lipids, including cholesterol, are generally insoluble in aqueous plasma. Plasma lipids are carried by soluble lipoprotein complexes. These lipoprotein complexes consist of an inner core of non-polar lipids (cholesteryl esters and triglycerides) and an surface layer of hydrophilic proteins and polar lipids (phospholipids and non-esterified cholesterol). Different proteins are present in the surface coat of different lipoprotein complexes (lipoproteins). The different lipoproteins perform different functions in lipid metabolism.

Five classes of lipoproteins are known. Some lipoproteins carry triglycerides and cholesterol from the liver to peripheral tissues while others transport lipids to the liver. Cholesterol may be metabolized in the liver to bile salts that are excreted, thus lowering total body cholesterol. Two lipoproteins, low density lipoproteins (LDL) and high density lipoproteins (HDL), have a high degree of association with the development of atherosclerosis. LDL has a high cholesterol concentration, delivers lipids to cells of peripheral tissues, and is associated with a high risk of atherosclerosis. HDL also has a relatively high cholesterol concentration, but carries lipids to the liver for metabolism into bile salts and is associated with decreasing the risk of developing atherosclerosis.

Cholesterol metabolism and homeostasis is the result of a complex equilibrium between free sterol in the cell and in plasma. Phillips et. al., Biochim. Biophys. Acta, 906:223 276 (1987). Delivery of cholesterol to cells occurs via the receptor-mediated LDL pathway and by passive exchange of sterol between plasma membranes and lipoproteins. Only tissues that produce steroid hormones and bile acids can metabolize cholesterol. In order to prevent accumulation of excess free sterol in remaining peripheral tissues there is a reverse transport of cholesterol from plasma membranes into HDL and lipoprotein-like particles. HDL transports excess cholesterol to the liver where it can either be processed into bile salts for excretion or incorporated into very low density lipoproteins (VLDL) to re-enter the lipoprotein pool.

The passive exchange of cholesterol between cells and lipoproteins occurs via the diffusion of sterol molecules across the aqueous space. Phillips et al., jupra, and Schroeder et al., Exp. Biol. Med., 196:235–252 (1991). Net cellular efflux: occurs if the chemical potential of free cholesterol is lower in the plasma than in the cells so that sterol leaves the membrane following its activity gradient.

Under these conditions, it has been shown that cholesterol ester-loaded cells, which are morphologically characteristic of early atherosclerotic lesions, not only lose cholesterol, but promote ester hydrolysis, resulting in the reduction of intracellular deposits of this lipid. Small, Arteriosclerosis, 8:103–129 (1988). Moreover as mentioned above, there is epidemiological evidence that conditions which might be expected to enhance reverse cholesterol transport (low plasma cholesterol concentrations, or increased HDL concentrations) are correlated with reduced risk of premature atherosclerosis and may give rise to plaque regression.

Characteristically, plaques are associated with ulceration of the vessel intima. The lipid-containing plaques grow in the ulcerations projecting friable masses into the arterial lumen. The plaques may also injure and weaken the smooth muscle media of the vessel. As plaque formation progresses, more central regions of the plaques are shielded from the circulation. Extensive plaque formation also cause concentric constriction of the vessel at the plaque site.

Presently, the most effective treatment of atherosclerosis is prevention. There is evidence that the progression and accumulation of lipids in lesions can be halted when plasma LDL concentrations are kept to near normal levels. Reynolds, Circulation, 79:1146–1148 (1989). Current preventive management of atherosclerotic disease has focused on the use of drugs in conjunction with dietary restrictions to regulate plasma cholesterol levels. Moreover, antioxidant therapies which suppress the formation and uptake of modified LDL particles by the cells of the arterial wall are also proving beneficial. Chisolm, Clin. Cardiol, 14:25–30 (1991).

However, while hypocholesterolemic drugs induce favorable plasma cholesterol changes which appear to slow the progression of atherosclerosis, they do hot generally induce conditions that promote the efflux and removal of atheroma cholesterol. Clearly, in order to achieve significant regression of atheroma and lessen lumen obstruction, these space occupying lipids must be mobilized. Present evidence suggests that processes which stimulate the efflux of extrahepatic cell cholesterol and transport it to the liver for excretion, reverse cholesterol transport (RCT), are important events in the prevention of atherosclerosis. Gwynne, Clin. Cardiol., 14:17–24 (1991).

Current therapeutic modalities of arteriosclerosis are generally divided into surgical and medical management. Surgical therapy may entail vascular graft procedures to bypass regions of occlusion (e.g., coronary artery bypass grafting), removal of occluding plaques from the arterial wall (e.g., carotid endarterectomy), or percutaneously cracking the plaques (e.g., balloon angioplasty). Surgical therapies carry significant risk and only treat isolated lesions.

Atherosclerotic plaques downstream from the treated lesion may continue to obstruct blood flow. Surgical therapies also do not limit the progression of atherosclerosis and are associated with the late complication of restenosis. Medical therapy is directed to reducing other risk factors related to vascular disease (e.g., smoking, diabetes, and hypertension) and lowering forms of serum cholesterol that are associated with the development of atherosclerosis as described above. While medical therapies may slow the progression of plaqye formation, plaque regression is relatively rare. Therefore, symptomatic atherosclerosis often requires both surgical and medical treatment.

Paradoxically, intravenous infusion of phospholipids and liposomes has been shown to produce regression of atherosclerotic plaques although serum lipid levels are transiently elevated. Williams et al., Perspect. Biol. Med., 27:417–431 (1984). In some instances, however, cholesterol associated with development and progression of atherosclerosis may increase following liposome administration.

Previous studies investigating phospholipid-induced mobilization of cholesterol in vivo have employed multilamellar or sonicated liposome vesicles. Liposome size is a key characteristic in clearance kinetics and is one of several reasons why sonicated vesicles have been expected to represent the bilayer structure best suited to enhance reverse cholesterol transport. Sonication reduces multilamellar vesicles (MLV) to 'limit size' vesicles. These systems exhibit the minimum radius of curvature that can be adopted by the bilayer configuration without disruption. For example, the minimum size egg phosphatidyl choline liposome that can be generated is typically about 30-nm diameter, often classified as a small unilamellar vesicle (SUV). For a given liposome composition, it is generally assumed that the smaller the particle diameter the greater the circulation half-life (Gregoriadis and Senior, Life SO, 113:183–192 (1986)). Consequently, it was expected that SUV composed of phosphatidyl choline would circulate longer than larger liposomes, and therefore mobilize more cholesterol.

Furthermore, packing constraints experienced by phospholipids in SUV, (due to the acute radius of curvature) gives rise to an instability that can result in fusion, Hope et al., Chem. Phys. Livids, 40:89–107 (1986), as well as an increased tendency to assimilate with lipoproteins. See, e.g., Scherphof et al., Biochem. Biophys. Acta, 542:296–307 (1978) and Krupp et al., Biochem. Biophys. Acta, 72:1251–1258 (1976). Therefore, it was expected that SUV would produce a greater number of HDL-like particles, thus promoting efflux of sterol from peripheral tissues supporting this expectation, liposomes having diameters of 50–80 nm have been reported to optimize sterol mobilization and plaque regression. European Patent Publication No. 0461559A2.

What is needed in the art is a medical treatment for atherosclerosis that not only will slow progression of lesions, but also predictably cause regression and shrinkage of established plaques. Such a treatment should provide the optimal rate of cholesterol removal (and, hence shrinkage) from plaques.

The present invention fulfills these and other related needs.

SUMMARY OF THE INVENTION

The present invention provides a pharmaceutical composition, devices, modes of operation of devices, kit, and method of forcing the reverse transport of cholesterol from peripheral tissues to the liver in vivo while controlling plasma LDL concentrations. A method described above includes the step of administering a therapeutically effective amount of a multiplicity of large liposomes comprised of phospholipids substantially free of sterol for a treatment period. A method described above optionally includes the step of periodically assaying plasma LDL concentrations with an assay during the treatment period to assess plasma atherogenic lipoprotein concentrations and obtain an atherogenic lipoprotein profile, and adjusting the administration in response to the profile. The large liposomes are dimensioned larger than fenestrations of an endothelial layer lining hepatic sinusoids in the liver so that the liposomes are too large to readily penetrate the fenestrations. The therapeutically effective amounts are in the range of about 10 mg to about 1600 mg phospholipid per kg body weight per dose. A pharmaceutical composition and related kit for mobilizing peripheral cholesterol and sphingomyelin that enters the liver of a subject consisting essentially of liposomes of a size and shape larger than fenestrations of an endothelial layer lining hepatic sinusoids in the liver is also provided.

The present invention provides a pharmaceutical composition consisting essentially of large liposomes comprised of phospholipids substantially free of sterol. The composition forces the reverse transport of cholesterol from peripheral tissues to the liver in vivo. The invention further provides a method of treating atherosclerosis in a subject comprising the step of administering a liposome composition to the subject. The liposome composition is selected from the group consisting of unilamellar liposomes and multilamellar liposomes and the liposomes have an average diameter of about 50–150 nanometers. LDL levels in the subject do not increase with utilization of a method described above.

The invention also provides a method of controlling cholesterol metabolism in hepatic parenchymal cells in a subject in vivo through cell—cell communication from Kupffer cells to the parenchymal cells. A method described above includes the step of administering a liposome composition to a subject. The liposome composition is selected from the group consisting of large unilamellar liposomes and large multilamellar liposomes, and the liposomes having an average diameter of about 50–150 nanometers. Similarly, LDL levels in the subject do not increase. In variants, the liposome composition is given periodically, given more than once, or given in repeated doses.

The liposomes have diameters larger than about 50 nm, diameters larger than about 80 nm, and diameters larger than about 100 nm in different variants. Administration is selected from the group of parenteral administration, intravenous administration, intra-arterial administration, intra-muscular administration, subcutaneous administration, transdermal administration, intraperitoneal administration, intrathecal administration, via lymphatics, intravascular administration, including administration into capillaries and arteriovenous shunts, rectal administration, administration via a chronically indwelling catheter, and administration via an acutely placed catheter, and given in about 10 to about 1600 mg/kg/dose of the liposome composition. The liposomes are phospholipids selected from the group consisting of phosphatidyl choline, phosphatidyl glycerol, palmitoyloleoyl phosphatidyl choline, combinations thereof, and derivatives thereof.

The present invention provides an improved mode of operation of an apparatus for angioplasty or cardiac catheterization, apparatus for angioplasty and cardiac catheterization, and method of angioplasty or cardiac catheterization. The improved mode of operation includes a mode of operation involving the administration of a therapeutically effective amount of a lipid acceptor during angioplasty or cardiac catheterization of a subject with the apparatus or component thereof. The lipid acceptor is selected from the group consisting of a large liposome comprised of phospholipids substantially free of sterol and small acceptors. The effective period of time is in the range of about less than 1 minute to about two years from the time of the angioplasty or cardiac catheterization. The improved angioplasty or cardiac catheterization apparatus includes means for administering a therapeutically effective amount of a lipid acceptor, and optional co-administration means for administering the lipid acceptor and a diagnostic agent. The improved mode of operating an angioplasty or cardiac catheterization apparatus includes administering a therapeutically effective amount of a lipid acceptor from the apparatus or component thereof into a vessel of a subject by administration means disposed on the apparatus. The invention further provides a method of diagnosing a side-effect of reverse transport of cholesterol from peripheral tissues to the liver in vivo accompanying parenteral administration of a multiplicity of large liposomes and small liposomes during a treatment period. A method described above includes the step of periodically assaying plasma atherogenic lipoprotein concentrations with an assay to obtain an assayed atherogenic lipoprotein concentration. The objects and features of the present invention other than those specifically set forth above, will become apparent in the detailed description of the invention.

A method of regulating cholesterol related genes, enzymes and other compounds, pharmaceutical compositions and a kit related thereto are provided. Exemplary genes that are regulated include a gene for an LDL receptor, a gene for HMG-CoA reductase, a gene for cholesterol 7-alpha-hydroxylase, and a gene regulating a function involved in cholesterol homeostasis. A method described above comprises the step of parenterally administering a therapeutically effective amount of a lipid acceptor. The lipid acceptor in one variant includes a multiplicity of large liposomes comprised of phospholipids substantially free of sterol during a treatment period. A method described above includes the steps of periodically assaying plasma LDL concentrations with an assay during a period of time to assess the plasma LDL and to obtain an LDL profile, and adjusting the parenteral administration in response to the LDL profile. A method described above further includes the step of enhancing tissue penetration of a cholesterol acceptor and enhancing extraction of tissue cholesterol and other exchangeable material with co-administration of an effective amount of a compound selected from the group consisting of a small acceptor of cholesterol, an amphipathic compound, and a drug that increases endogenous small acceptors of cholesterol.

Generally the compositions described herein include large liposomes of a size and shape larger than fenestrations of an endothelial layer lining hepatic sinusoids in the liver, whereby the liposomes are too large to readily penetrate the fenestrations. Therapeutically effective amounts of the compositions include in the range of 10 mg to 1600 mg phospholipid per kg body weight per dose. The large liposomes are selected from the group consisting of uni-lamellar liposomes and multi-lamellar liposomes. In variants, the liposomes have diameters larger than about 50 NM, diameters larger than about 80 NM, and diameters larger than about 100 NM.

The present invention provides compositions for, a method of suppressing the rise in plasma concentrations of atherogenic lipoproteins after administration of an agent having small acceptors of cholesterol, other lipids or compounds. A method described above includes the step of co-administering an effective amount of a multiplicity of an agent having large liposomes that include phospholipids substantially free of sterol with the administration of the agent having the small acceptors. The atherogenic lipoproteins include LDL, VLDL, IDL, β-VLDL, Lp(a), a lipoprotein containing apolipoprotein-B, oxidized lipoproteins, and modified lipoproteins. The agent having small acceptors consists essentially of small acceptors and in which the agent having large liposomes consists essentially of large liposomes. In a variant, co-administration of the agent having large liposomes is simultaneous with the administration of the agent having small acceptors. Optionally, co-administration of the agent having large liposomes is separated in time from the administration of the agent having small acceptors by an effective time period. An improved pharmaceutical composition for reducing the size of arterial lesions that enters the liver of a subject is also provided the improvement comprises an anti-oxidant and derivatives thereof. The invention also provides an improved mode of operation of liposomes utilizing the improvements described herein.

The present invention further provides various methods, systems and compositions for forcing the reverse transport of cholesterol from peripheral tissues to the liver in vivo while controlling plasma LDL concentrations, and other significant components of living biological systems. A method described above comprises the step of parenterally administering a therapeutically effective amount of a multiplicity of large liposomes comprised of phospholipids substantially free of sterol for a treatment period whereby the liposomes pick-up the cholesterol during the treatment period. A method described above optionally includes the step of periodically assaying plasma LDL concentrations with an assay during the treatment period to assess the plasma LDL concentrations and obtain an LDL profile, and adjusting the parenteral administration in response to the LDL profile.

Exemplary assays are selected from the group consisting of an assay of plasma esterified cholesterol, an assay of plasma apolipoprotein-B, a gel filtration assay of plasma, an ultracentrifugal assay of plasma, a precipitation assay of plasma, and an immuno turbidometric assay of plasma.

A method described aboves optionally include the step of enhancing tissue penetration of a cholesterol acceptor by co-administration of an effective amount of a compound, the compound selected from the group consisting of a small acceptor of cholesterol and a drug that increases endogenous small acceptors of cholesterol. The small acceptor is selected from the group consisting of a high-density lipoprotein, a phospholipid protein complex having a group selected from the group consisting of apoA-I, apoA-II, apoA-IV, apoE, synthetic fragments thereof, natural fragments thereof, an amphipathic protein, and an amphipathic peptide, the protein substantially free of phospholipid, small phospholipid liposomes, and a small cholesterol acceptor. This includes an agent that raises physiologic HDL concentrations, the agent selected from the group consisting of nicotinic acid, ethanol, a fibric acid, a cholesterol synthesis inhibitor, a drug that increases HDL concentrations, and derivatives thereof. The invention further provides a method of, and composition for regulating hepatic parenchymal cell cholesterol content and gene expression by the steps described herein.

The present invention provides an improved dialysis apparatus for the treatment of a subject, improved mode of operation of a dialysis apparatus and improved method of dialysis. The improvement includes means for and a mode of operation for administering a therapeutically effective amount of a lipid acceptor during the treatment of a subject, and actuation of the means during operation of the dialysis apparatus. The lipid acceptor is selected from the group consisting of a multiplicity of large liposomes comprised of phospholipids substantially free of sterol and small acceptors. The means for administering the agent is selected from the group consisting of means for extracorporeal administration and means for intracorporal administration. The dialysis includes hemodialysis, peritoneal dialysis, and rectal dialysis, and the agent is added directly to blood or blood plasma of a subject in one variant.

Liposome compositions utilized herein also pick up and are useful in removing undesirable components in addition to cholesterol which improves the dialysis. Accordingly, an assay of the undesirable components, which may include lipids and other exchangeable material, is used to determine the effectiveness of the treatment. A method described above, mode of operation and apparatus provide for the control of plasma LDL concentrations, plasma concentrations of atherogenic lipoproteins and hepatic cholesterol homeostasis.

It is an object of the present invention to provide for better methods to manipulate the lipid content and composition of peripheral tissues, cells, membranes, and extracellular regions in vivo, particularly in regard to diseases and processes involving oxidation and oxidative damage. It is a further object of the present invention to provide for methods or compounds that can produce a removal of cholesterol and other exchangeable material, including oxidized materials, from peripheral cells, tissues, organs, and extracellular regions, and that can produce a delivery of anti-oxidants to cells, tissues, organs, and extracellular regions, but without harmfully disrupting hepatic cholesterol homeostasis, including hepatic gene expression and regulation.

It is an object of the invention to provide better methods to manipulate the lipid content and composition of peripheral tissues, cells, membranes, and extracellular regions in vivo.

It is a further object of the invention to regulate and control deranged hepatic cholesterol homeostasis as manifested by abnormal regulation of genes, such as a gene for the LDL receptor, ax gene for HMG-CoA reductase, a gene for cholesterol 7-alpha hydroxylase, and a gene regulating a function involved in removal of cholesterol and other exchangeable material from peripheral cells, tissues, organs, and extracellular regions, but without harmfully disrupting hepatic cholesterol homeostasis, including hepatic gene expression and regulation.

It is an object of the invention to provide a simple, effective, non-invasive or minimally invasive approach, method, device, and mode of operation of the device to reduce re-stenosis or slow its development in patients who undergo mechanical or surgical revascularization procedures.

It is a further object of the invention to provide a method, device, and mode of operation of a device to manipulate the lipid content and composition of the arterial wall before, during, and after revascularization procedures, to reduce re-stenosis. It is a further object of the invention to provide for a method to change LDL composition and size.

It is yet another object of the invention to provide a method, compound, device and mode of operation of a device that can produce a removal of cholesterol and other exchangeable material from peripheral cells, tissues, organs, and extracellular regions without harmfully disrupting hepatic cholesterol homeostasis.

It is an object of the invention to provide for better methods to manipulate the lipid content and composition of peripheral tissues, cells, membranes, and extracellular regions in vivo.

It is a further object of the invention to provide for methods and compounds that can produce removal of cholesterol from cellular and extracellular regions of arteries, but without provoking a rise in the plasma concentration of LDL.

It is an object of the present invention to provide a better method to manipulate the lipid content and composition of peripheral tissues, cells, membranes, and extracellular regions in vivo.

It is a further object of the invention to provide methods or compounds that can produce a removal of cholesterol and other exchangeable material, from peripheral cells, tissues, organs, and extracellular regions, and that can produce a delivery of material, such as phospholipids, to cells, tissues, or organs, extracellular regions, but without harmfully disrupting hepatic cholesterol homeostasis and plasma concentrations of atherogenic lipoproteins.

In one variant, the present invention provides pharmaceutical compositions consisting essentially of unilamellar liposomes having an average diameter of about 100–150 nanometers, which liposomes are not bound to a drug; and a pharmaceutically acceptable carrier. These liposomes optimize cholesterol efflux from atherosclerotic plaques. The liposomes may be bound to an apoprotein, typically apoprotein A1 or A2. The liposomes often contain at least one phospholipid, such as phosphatidyl choline or phosphatidylglycerol. Liposomes having diameters of about 125 nm are preferred.

Also provided are methods for treating atherosclerosis employing the pharmaceutical compositions of the present invention. The compositions are administered to animals having atherosclerosis often, the compositions will be serially administered over a period of time. Generally, the compositions will be administered parenterally, usually intravenously. The methods may be employed therapeutically or prophylactically. The methods of the present invention are also useful for treatment of hypoalphalipoproteinemia and hyperlipidemias.

The objects and features of the present invention, other than those specifically set forth above, will become apparent in the detailed description of the invention set forth below.

BRIEF DESCRIPTION OF THE DRAWINGS

FIG. 2 illustrates a table of hepatic mRNA content (pg/$\mu$g) for CETP, HMG-CoAR, LDL receptors, and 7a-hydroxylase; and LDL ChE;

FIG. 9 illustrates key points about LUVs and atherosclerosis;

FIG. 18 illustrates that the compositions and methods of the present invention are effective in humans;

DETAILED DESCRIPTION OF THE INVENTION

Figure 1:
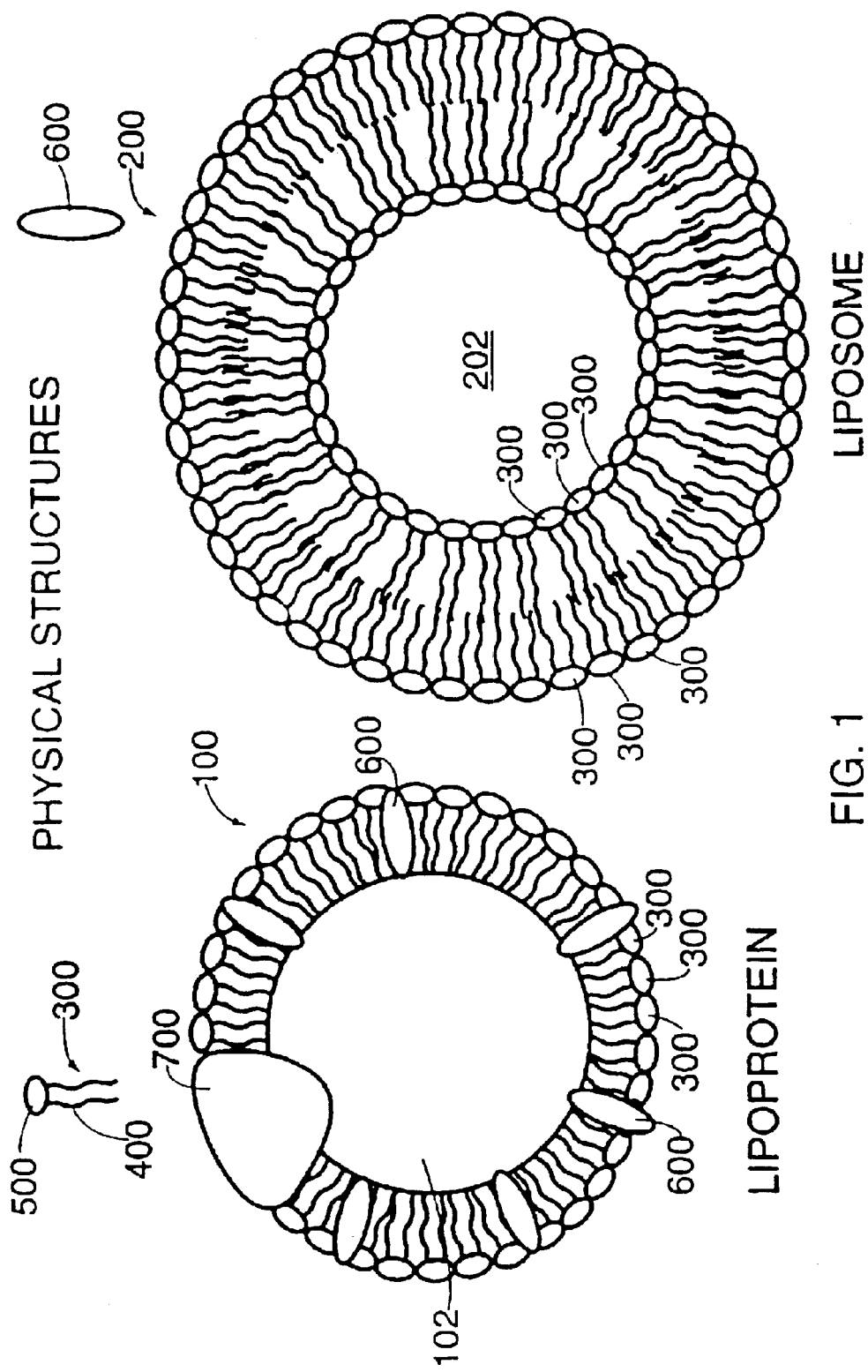
FIG. 1 is a side cross-sectional view of a lipoprotein and a liposome.

FIG. 1 illustrates a schematic illustration of the structure of a normal lipoprotein 100 and a unilamellar liposome 200. Lipoprotein 100 and liposome 200 are comprised of a phospholipid molecule 300. Phospholipid molecules generally have polar head 500 and a fatty acyl chains 400. Molecule 600 represents a molecule of unesterifed cholesterol. Lipoprotein 100 is comprised of a hydrophobic core 102 composed mainly of triglycerides and cholesteryl esters surrounded by a monolayer of phospholipid molecules 300 with their fatty acyl side chains 400 facing the hydrophobic core 102 and their polar heads 500 facing the surrounding aqueous environment (not shown). Unesterified cholesterol 600 is found largely within the phospholipid monolayer. Apolipoprotein 700 is disposed within phospholipid molecules 300. Artificial triglyceride emulsion particles have essentially identical structures, either with or without protein.

Liposome 200 is comprised of phospholipid molecules 300 forming a phospholipid bilayer, e.g. one lamella, either with or without protein, in which fatty acyl side chains 400 face each other, the polar head groups 500 of the outer leaflet face outward to the surrounding aqueous environment (not shown), and the polar head groups 500 of the inner leaflet face inward to the aqueous core 202 of the particle 200. Depending on the composition of particle 200, phospholipid bilayers can have a large capacity for unesterified cholesterol and other exchangeable material and components thereof. As illustrated in FIG. 1 there is no sterol. Typically, such liposomes can pick up unesterified cholesterol from other lipid bilayers, such as cell membranes, and from lipoproteins. Liposomes also pick up proteins and donate phospholipids and other exchangeable material and components thereof. Liposomes can also have multilamellar structures, in which the bilayers are contained within the environment encapsulated by an outer bilayer to form multiple lamellae. The multiple lamellae can be arranged concentrically, like the layers of an onion, or in another variant non-concentrically.

Figure 3:
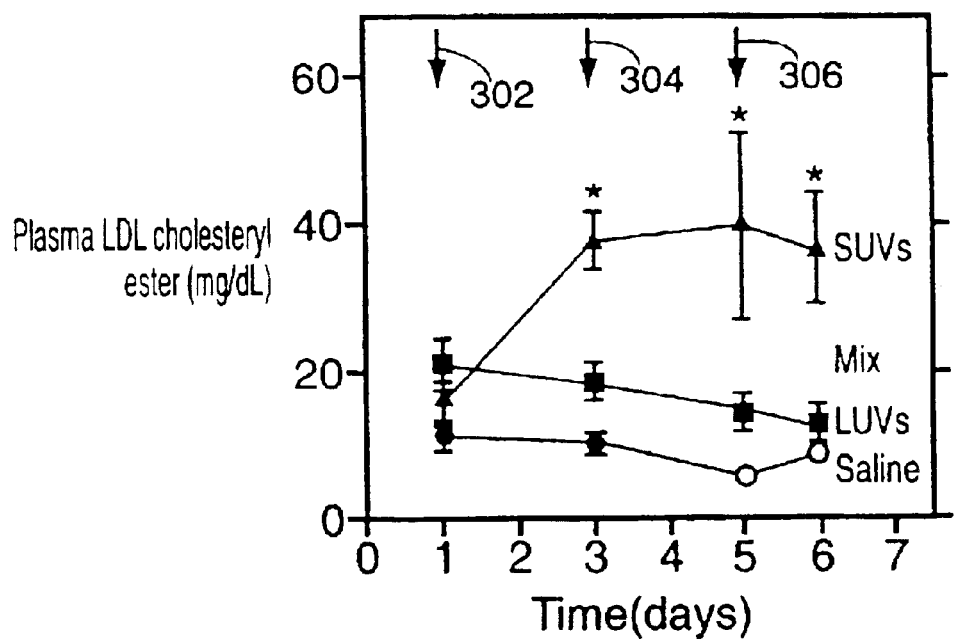
FIGS. 3 and 4 illustrate plasma LDL cholesteryl ester concentrations in response to injections of LUVs, SUVs or saline over time in one variant.
Figure 4:
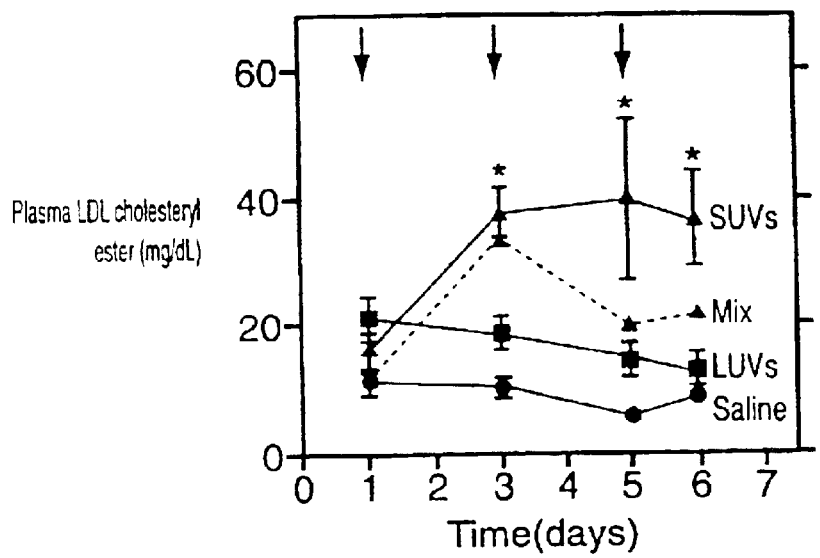

FIGS. 3 and 4 illustrate plasma LDL cholesteryl ester concentrations in response to injections of LUVs, SUVs or saline over time. Rabbits were intravenously injected on days 1, 3 and 5 as indicated by arrows 302, 304, and 306 respectively, with a bolus of 300 mg of phosphatidyl choline per kg of body weight or a matched volume of saline. The phosphatidyl choline was pharmaceutical grade egg PC, in the form of either large unilamellar vesicles (LUVS) having diameters of approximately 100 NM (preferably ~120 NM) prepared by extrusion (LUVs were measured at about 120 NM (123±35 NM and the extrusion membrane had pores of about 100 NM in diameter) or small unilamellar vesicles with diameters of approximately 30 NM (preferably 35 NM) prepared by sonication. (SUVs were measured in the range of 34±30 NM.) Blood was drawn just before each injection and on the sixth day at sacrifice. Plasma LDL cholesteryl ester concentrations were determined by a gel filtration assay of the plasma with an in-line enzymatic assay for cholesteryl ester. Means±SEMs are shown in FIG. 3. Animals infused with SUVs showed significantly higher plasma concentrations of LDL cholesteryl ester at days 3, 5, and 6 compared to either LUV-infused or saline infused animals. FIGS. 2–8, 10–15, 24 and 28 illustrate data from the same experiment in which injections were made on days 1, 3, and 5 and then livers were taken. Gel filtration was done of plasma to measure lipid contents of individual lipoprotein classes. FIG. 2 illustrates a table of hepatic mRNA content (pg/$\mu$g) for CETP, HMG-CoA R (hydroxy methylglutaryl coenzyme A reductase), LDL receptors, and cholesterol 7 alpha-hydroxylase; and LDL ChE (low density lipoprotein cholesteryl ester) for the rabbits given saline (HEPES buffered saline) (rabbits 1–4), LUVs (rabbits 5–8), and SUVs (rabbits 10–12) for the experiment described for FIGS. 3 and 4. Rabbit 13 is the "Mix" rabbit.

FIG. 4 shows an animal labeled as mix. "Mix" refers to a single animal that received SUVs on day 1, 3 and 5, but also one injection of LUVs on day 3. Before this injection of LUVs, the plasma concentration of LDL cholesteryl ester rose, but after the injection of LUVs, the LDL concentration fell, despite continued injections of SUVs.

Figure 5:
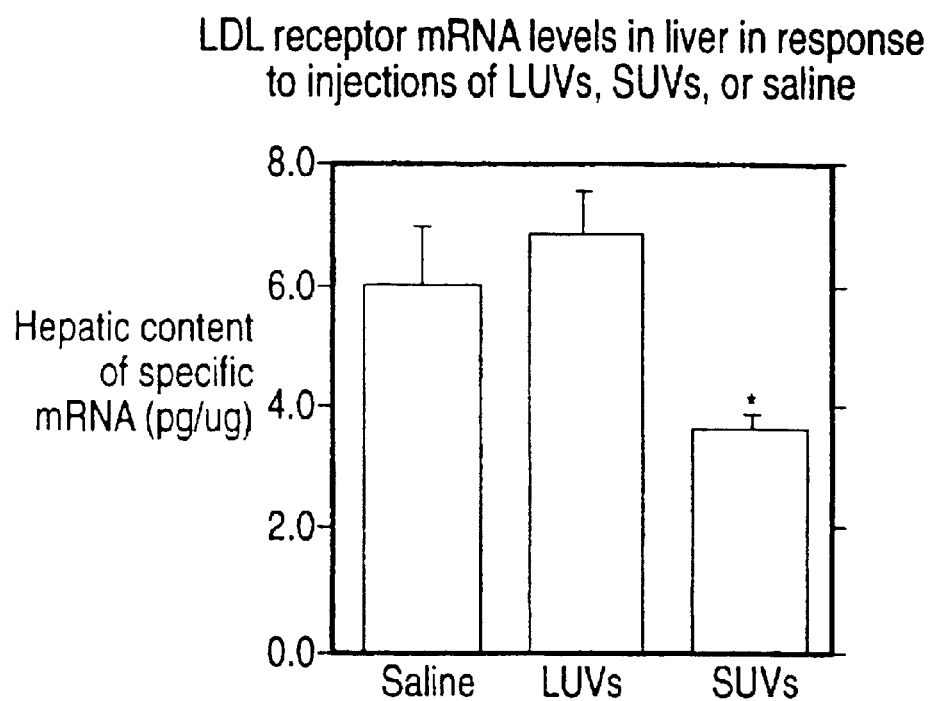
FIG. 5 illustrates LDL receptor mRNA levels in liver in response to injections of LUVs, SUVs or saline over time.

FIG. 5 illustrates LDL receptor mRNA levels in liver in response to injections of LUVs, SUVs or saline over time. The rabbits described above were sacrificed at day 6, and samples of liver were snap-frozen in liquid nitrogen. mRNA was extracted, and rabbit mRNA for the LDL receptor was quantified by an internal standard/RNase protection assay (Rea T. J. et al. J. Lipid Research 34:1901–1910, 1993 and Pape M. E., Genet. Anal. 8:206–312, 1991). Means±SEMs are shown in FIG. 5. Animals infused with SUVs showed significant suppression of hepatic LDL receptor mRNA compared to LUV-infused or saline-infused animals. Suppression of hepatic LDL receptor mRNA reflects parenchymal cell overload with sterol, and is a potentially harmful alteration from normal hepatic cholesterol homeostasis. In contrast, LUV-infused animals showed the highest levels of hepatic LDL receptor mRNA, though the increase above that seen in the saline-infused animals did not reach statistical significance. The liver from the "Mix" animal described above showed a value of 5.28 pg LDL receptor mRNA/ microgram which is closer to the average value in the saline group than in the SUV group. Thus, LDL receptor mRNA was stimulated by the single injection of LUVs despite repeated injections of SUVs.

Figure 6:
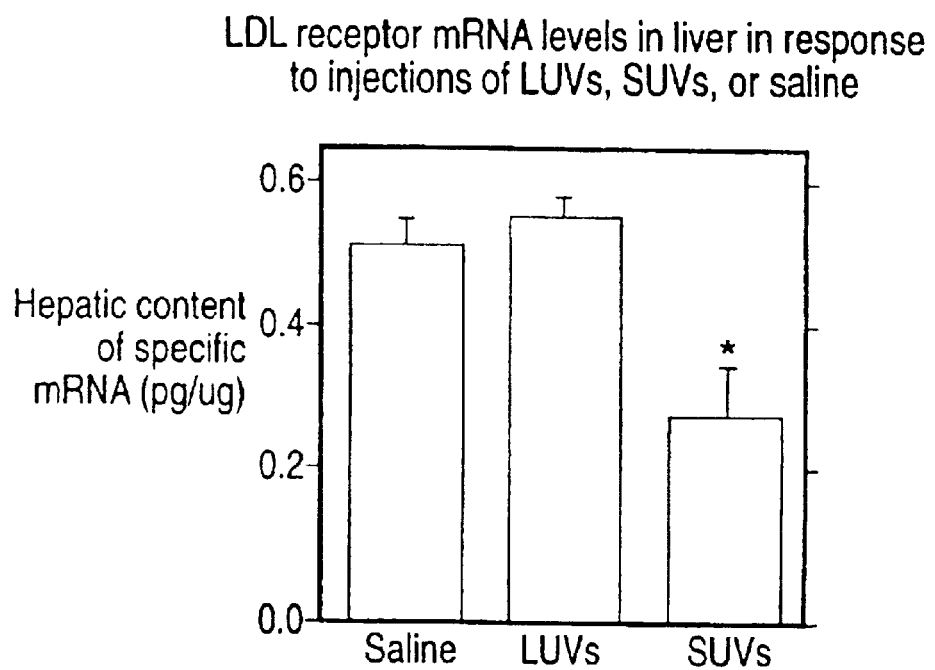
FIG. 6 illustrates HMG-CoA reductase mRNA levels in liver in response to injection of LUVs, SUVs, or saline.

FIG. 6 illustrates HMG-CoA reductase mRNA levels in liver in response to injections of LUVs, SUVs, or saline. The experimental details are those as referenced above. Animals infused with SUVs showed significant suppression of hepatic HMG-CoA reductase mRNA compared to LUV-infused or saline infused animals. Suppression of hepatic HMG-CoA reductase mRNA reflects parenchymal cell overload with sterol, which can be a potentially harmful alteration from normal hepatic cholesterol homeostasis. In contrast, LUV-infused animals showed the highest levels of hepatic HMG-CoA reductase mRNA, though the increase above that seen in the saline-infused animals did not reach statistical significance.

The "mix" animal showed a value of 0.50 pg HMG-CoA reductase mRNA/microgram, which is essentially identical to the average value in the saline group (0.51) and substantially higher than the value in the SUV group (0.27). Thus, HMG-CoA reductase mRNA was stimulated to its normal value by the single injection of LUVs, despite repeated injections of SUVs.

Figure 7:
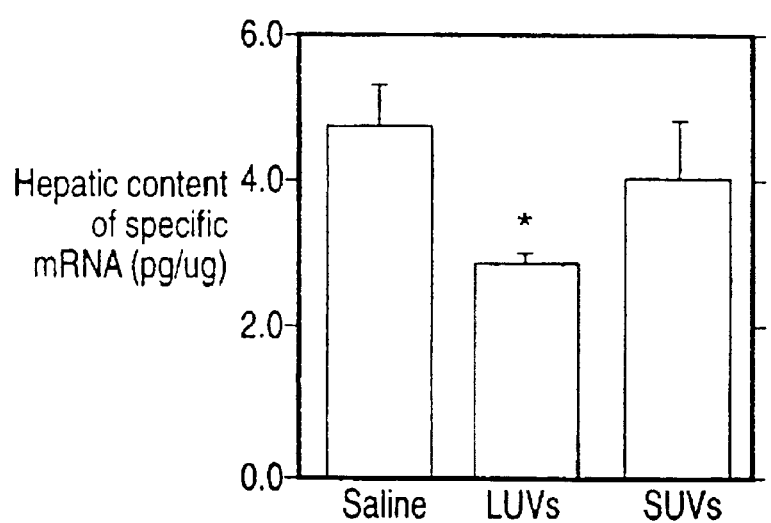
FIG. 7 illustrates cholesteryl ester transfer protein mRNA levels in liver in response to injection of LUVs, SUVs, or saline.

FIG. 7 illustrates cholesteryl ester transfer protein mRNA levels in liver in response to injection of LUVs, SUVs, or saline. The experimental details are those as referenced above. Animals infused with LUVs showed significant suppression of hepatic CETP mRNA compared to SUV infused or saline infused animals. Suppression of CETP mRNA produce changes in the plasma lipoprotein profile usually associated with reduced risk of atherosclerosis. The "mix" animal showed a value of 3.18 pg CETP mRNA/microgram, which is closer to the average value in the LUV group than in the SUV or saline groups. Thus, CETP mRNA was suppressed by the single injection of LUV's despite repeated injections of SUVs.

Figure 8:
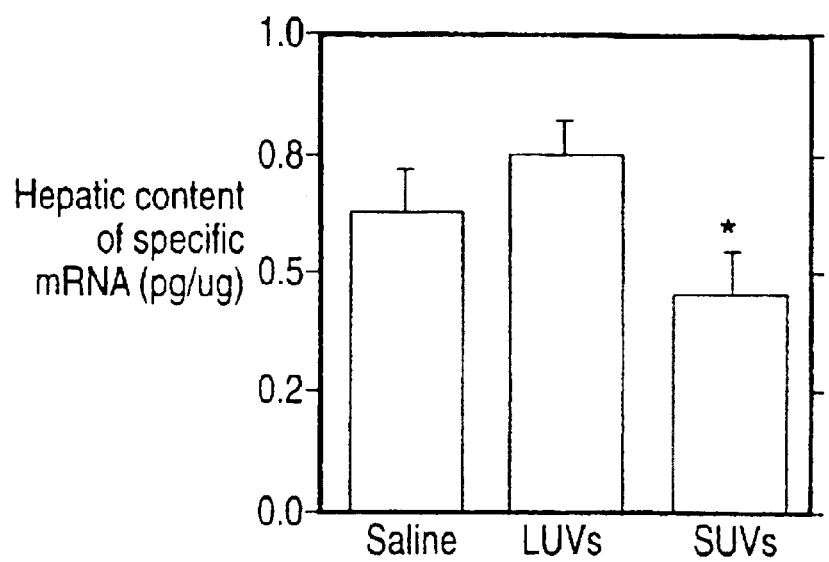
FIG. 8 illustrates 7-alpha hydroxylase mRNA levels in liver in response to injections of LUVs, SUVs, or saline.

FIG. 8 illustrates cholesterol 7-alpha hydroxylase mRNA levels in liver in response to injections of LUVs, SUVs, or saline. The experimental details are those as reference above. Animals infused with SUVs showed suppression of hepatic 7-alpha hydroxylase mRNA compared to LUV infused or saline infused animals. Suppression of 7-alpha hydroxylase can be a potentially harmful alteration from normal hepatic homeostasis. In contrast, LUV-infused animals showed the highest levels of hepatic 7-alpha hydroxylase mRNA, though the increase above that seen in the saline infused animals did not reach statistical significance. The "mix" animal showed a value of 0.51 pg 7-alpha hydroxylase mRNA/microgram, which is higher than the average value in the SUV group. Thus, 7-alpha-hydroxylase mRNA was stimulated by the single injection of LUVs, despite repeated injections of SUVs.

Figure 10:
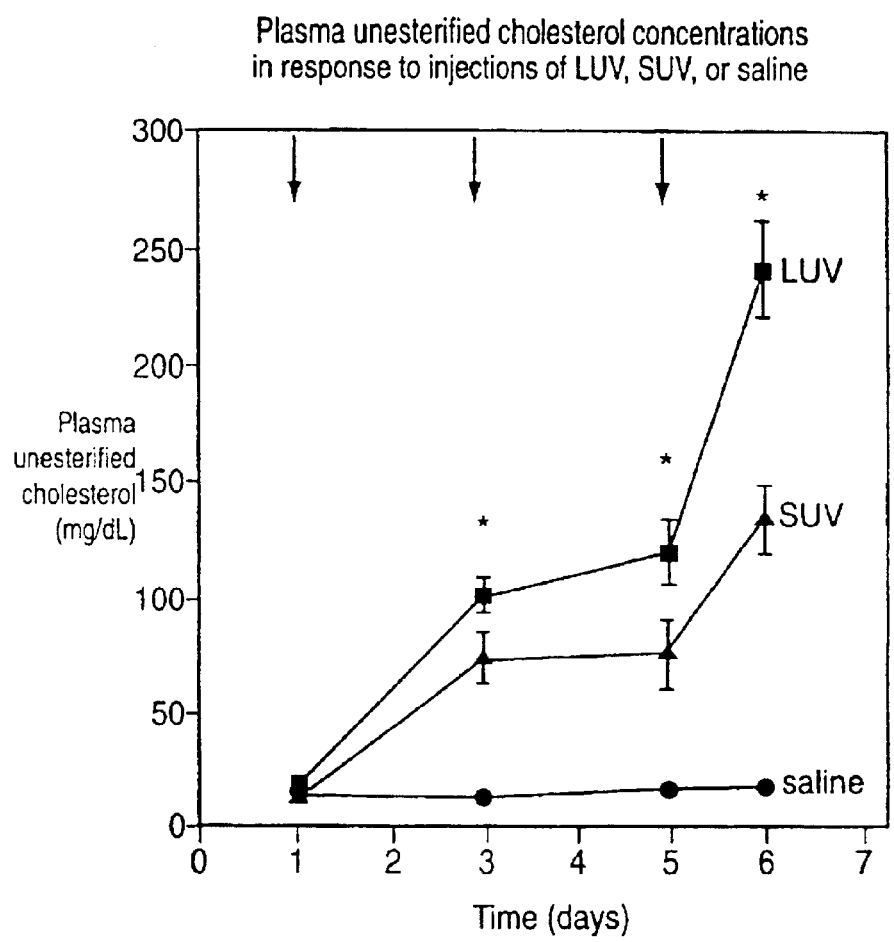
FIG. 10 illustrates plasma LDL unesterified cholesterol concentrations in response to injections of LUVs, SUVs or saline over time.

FIG. 10 illustrates unesterified cholesterol concentrations in whole plasma in response to injections of LUVs, SUVs, or saline over time. The experimental details are those as referenced above. As indicated by this figure, LUVs and SUVs significantly raised the plasma concentrations of unesterfied cholesterol indicating mobilization of tissue stores. The LUVs raised the concentration of unesterifed cholesterol more than did the SUVs.

Figure 11:
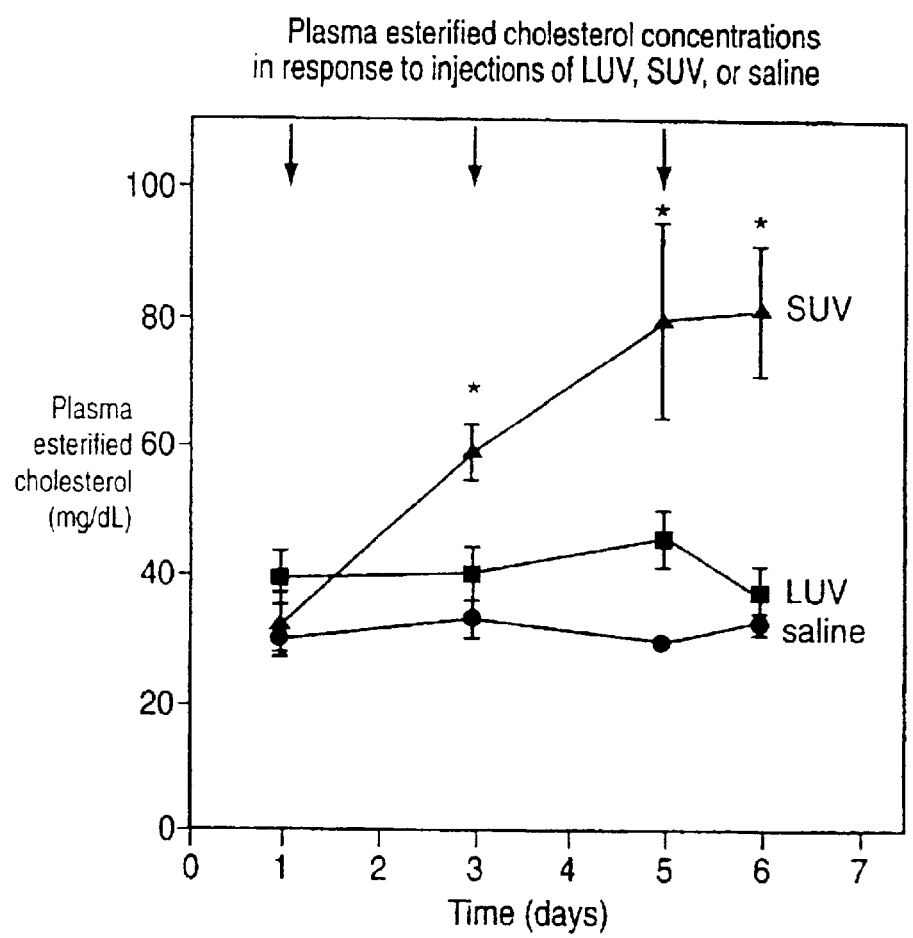
FIG. 11 illustrates plasma LDL esterified cholesterol concentrations in response to injections of LUVs, SUVs or saline over time.
Figure 12:
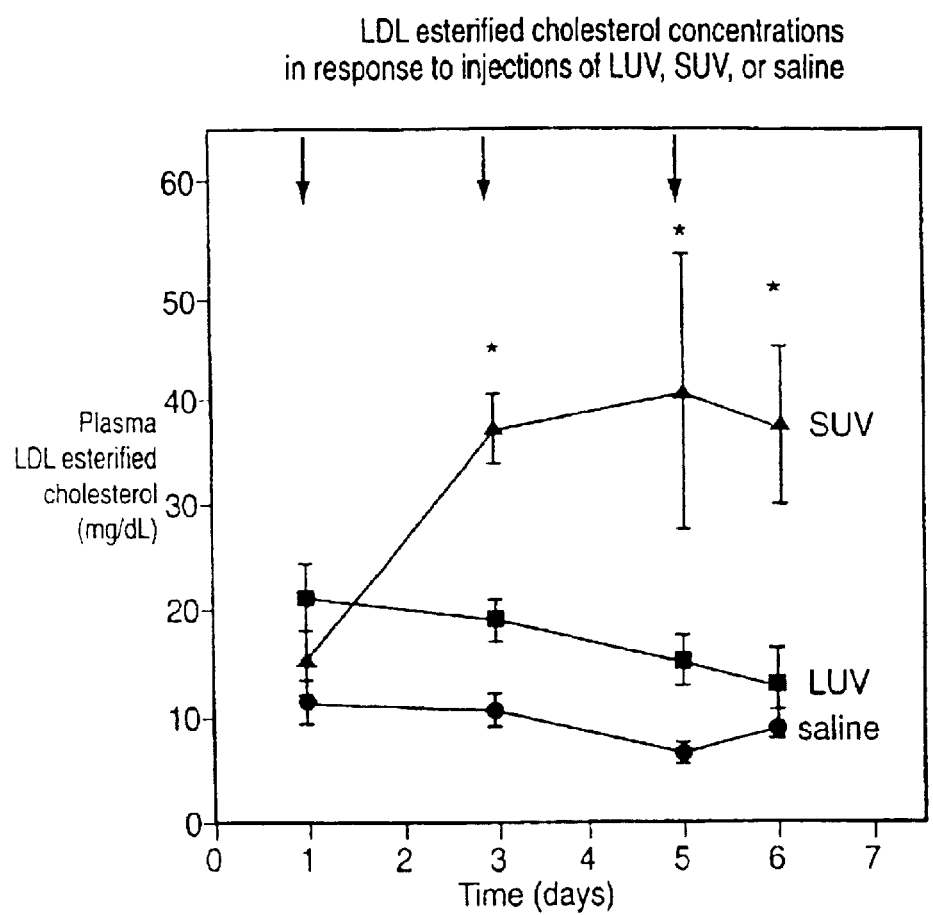
FIG. 12 illustrates LDL esterified cholesterol concentrations in response to injections of LUVs, SUVs or saline.

FIG. 11 illustrates esterified cholesterol concentrations in whole plasma in response to injections of LUVs, SUVs or saline over time. The experimental details are those as referenced above. SUVs raised the plasma concentrations of cholesteryl ester on days 3, 5, and 6. FIG. 12 duplicates the information contained in FIG. 3.

Figure 13:
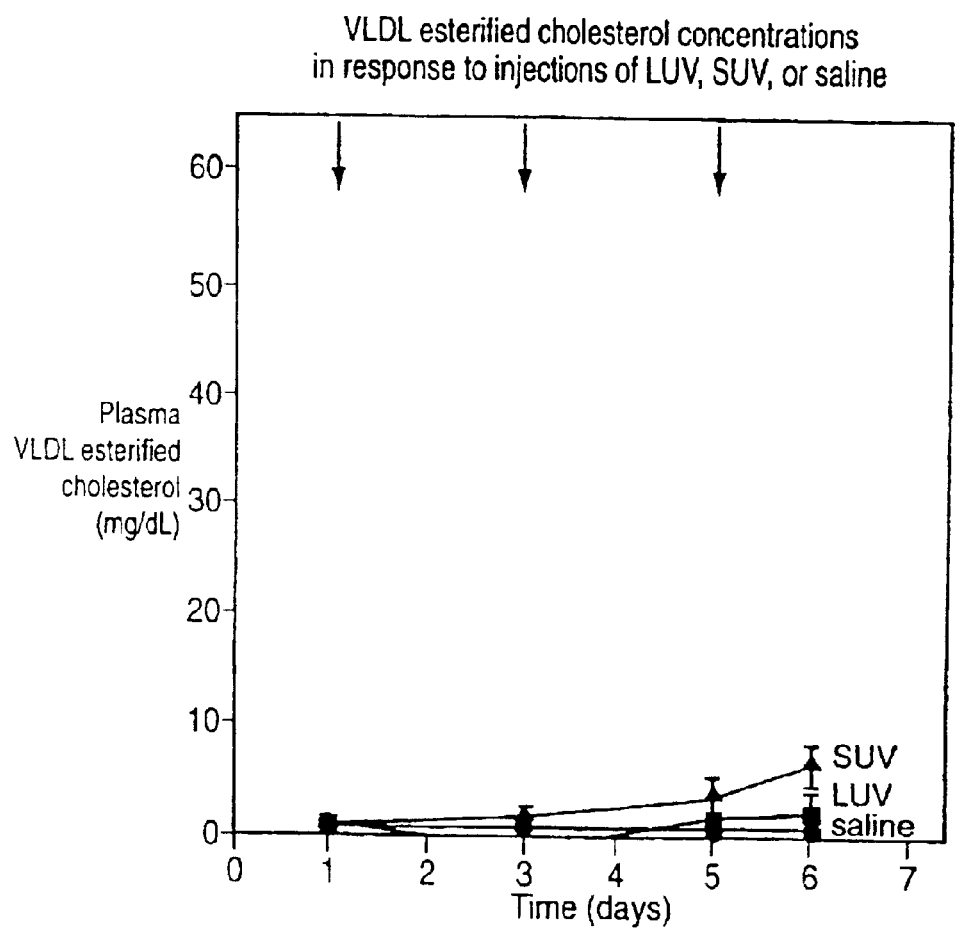
FIG. 13 illustrates plasma VLDL esterified cholesterol concentrations in response to injections of LUVs, SUVs or saline.

FIG. 13 illustrates plasma VLDL esterified cholesterol concentrations in response to injections of LUVs, SUVs, or saline. SUVs increased the plasma concentration of VLDL cholesteryl ester over that seen in the saline of LUV treated groups. The "mix" animal showed a plasma VLDL cholesteryl ester concentration at day 6 of 2.4 mg/dl, which is lower than the average value in the SUV group. The experimental details are those as referenced above.

Figure 14:
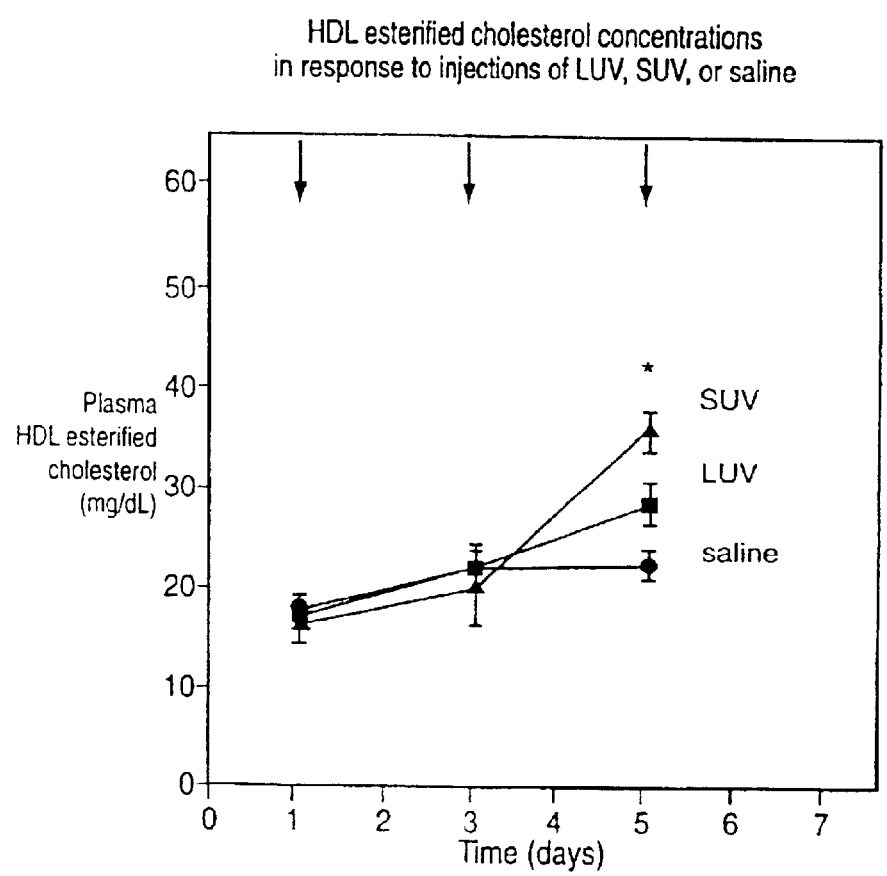
FIGS. 14 and 15 illustrate HDL esterified cholesterol concentrations in response to injections of LUVs, SUVs or saline.
Figure 15:
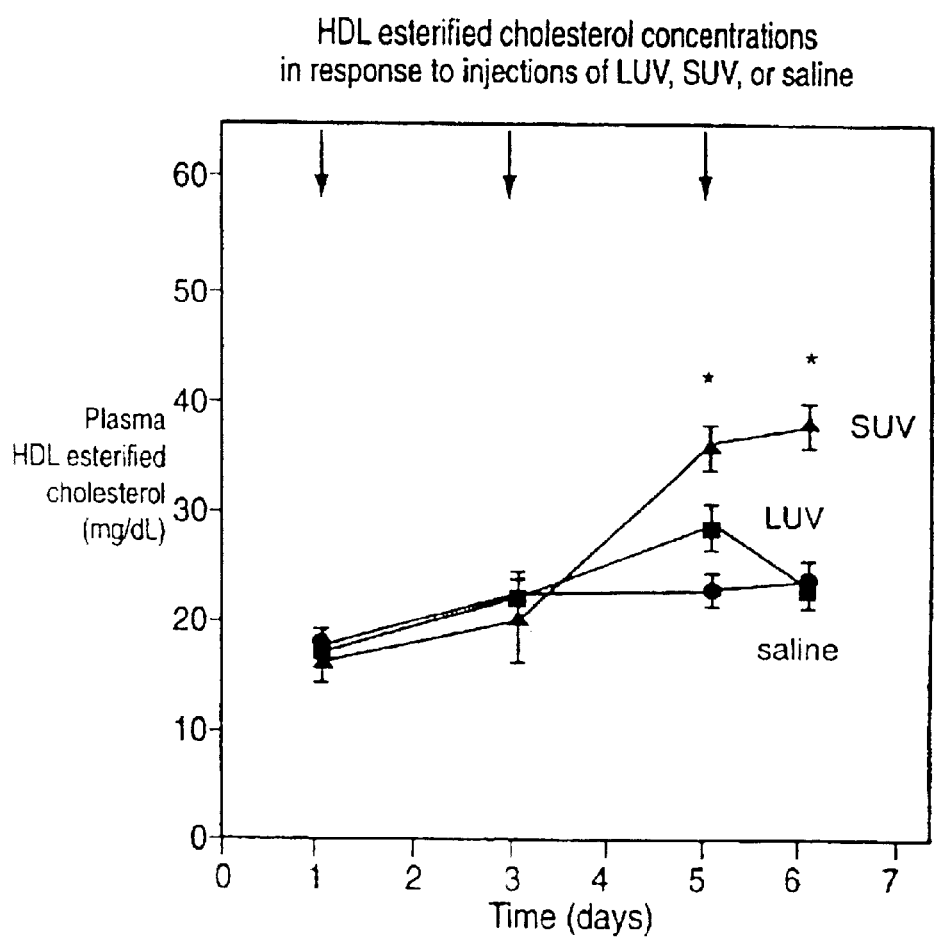

FIGS. 14 and 15 illustrate HDL esterified cholesterol concentrations in response to injections of LUVs, SUVs, or saline. The experimental details are those as referenced above as in FIG. 2. Suitable phospholipid can be obtained from Avanti Polar Lipids, Nippon Oil and Fat in Japan and Princeton Lipids, as well as other suppliers. LUVs are made through an extruder that is commercially available. SUVs caused a small but statistically significant rise in HDL cholesteryl ester concentrations on days five and six.

Figure 16:
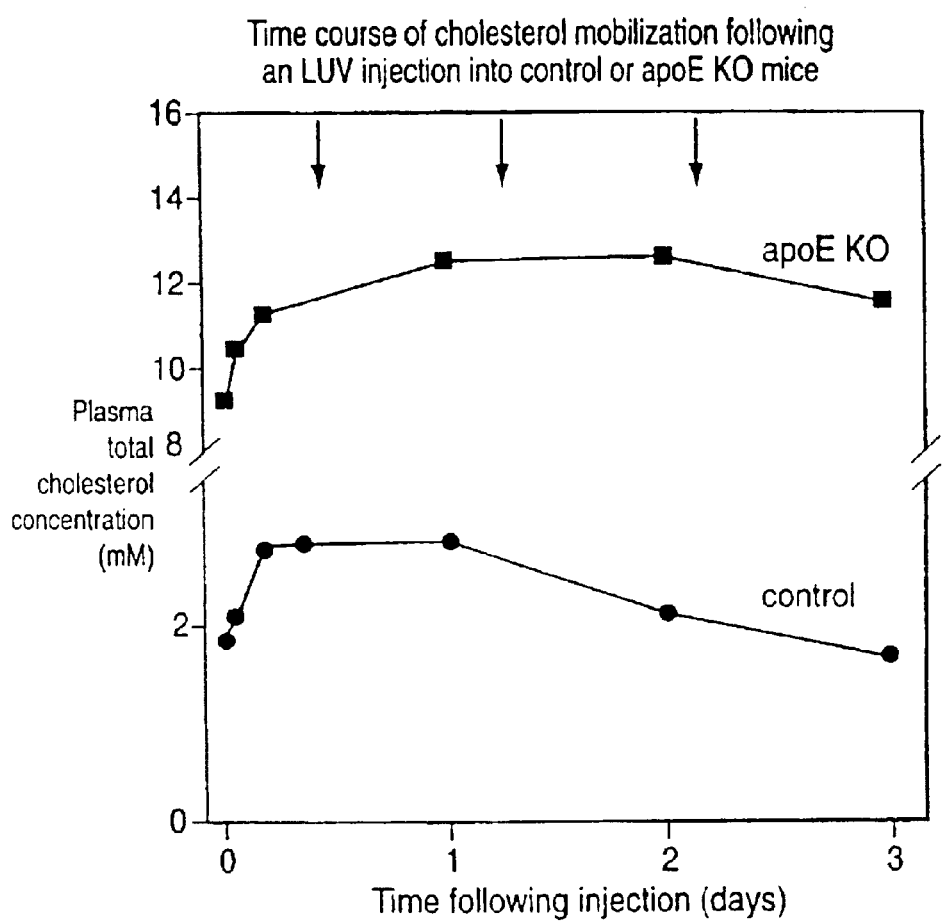
FIG. 16 illustrates the time course of cholesterol mobilization following an LUV injection into control or apoE KO mice.

FIG. 16 illustrates the time course of cholesterol mobilization following an LUV injection into control or apoE KO (knock-out) mice commercially available from Jackson Laboratories, in Bar Harbor, Me. Control (C57/BL6) and apolipoprotein E knock-out mice were injected at time zero with a single bolus of 300 mg LUV phospholipid/kg body weight. The LUVs contained a tracer amount of labeled cholesteryl hexadecylether, which remains on the liposomes after injection into a mouse. Displayed data are for concentrations of total cholesterol, i.e. esterified plus unesterifed, in whole plasma. The rise in both sets of animals indicated that LUVs mobilize cholesterol into the plasma, even in the presence of a severe genetic hyperlipidemia.

Figure 17:
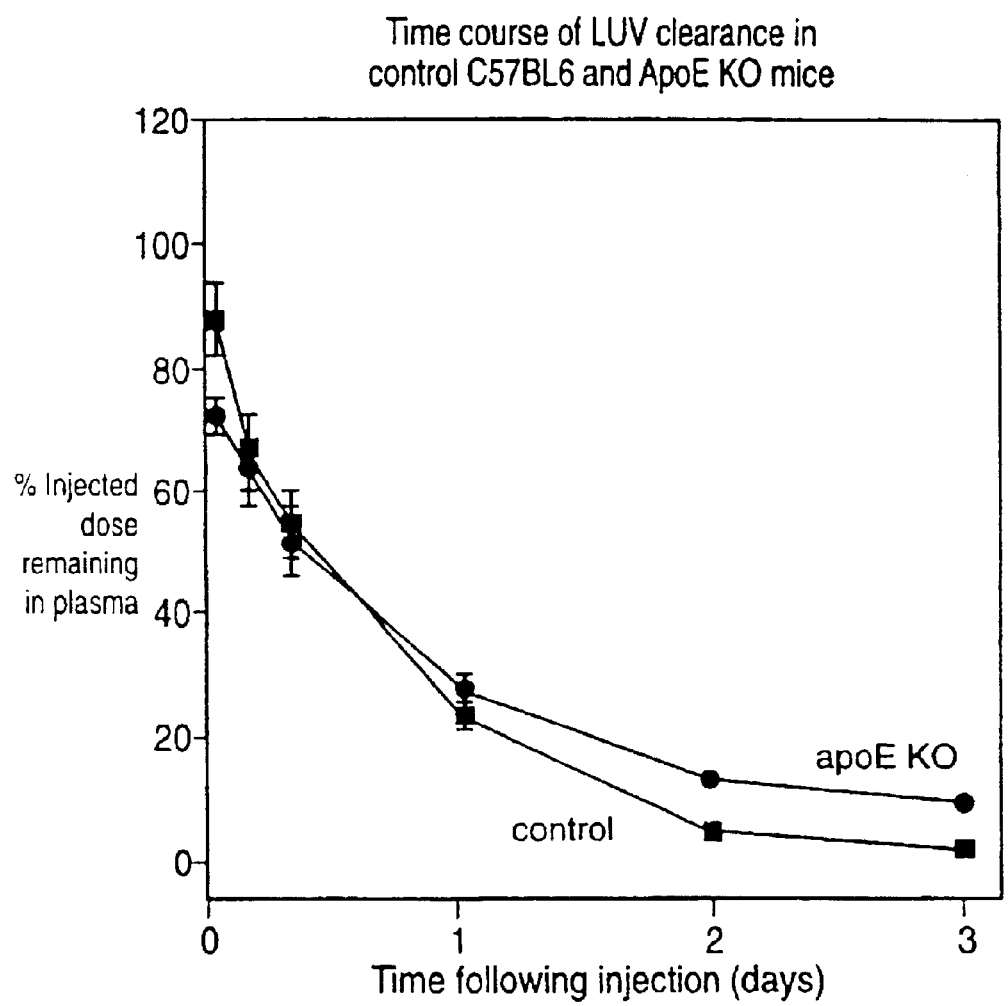
FIG. 17 illustrates the time course of LUV clearance in control mice and apoE mice.

FIG. 17 illustrates the time course of LUV clearance in control mice and apoE mice. The experimental details are as described in FIG. 16. The clearance of LUVs from the plasma is unimpaired in the apoE knock-out mice, indicating mobilization (FIG. 16) and disposal (FIG. 17) of cholesterol even in the presence of a severe genetic hyperlipidemia. This indicates the usefulness of this preparation in hyperlipidemias.

FIG. 18 illustrates exemplary applications for the compositions and methods of the present invention in humans. The therapeutic targets of the compositions and methods presented herein are lipid-rich, rupture prone plaques, critical stenosis, post-angioplasty re-stenosis, atherosclerosis in general, and any membrane, cell, tissue, organ, and extracellular region and/or structure, in which compositional and/or functional modifications would be advantageous.

Figure 19:
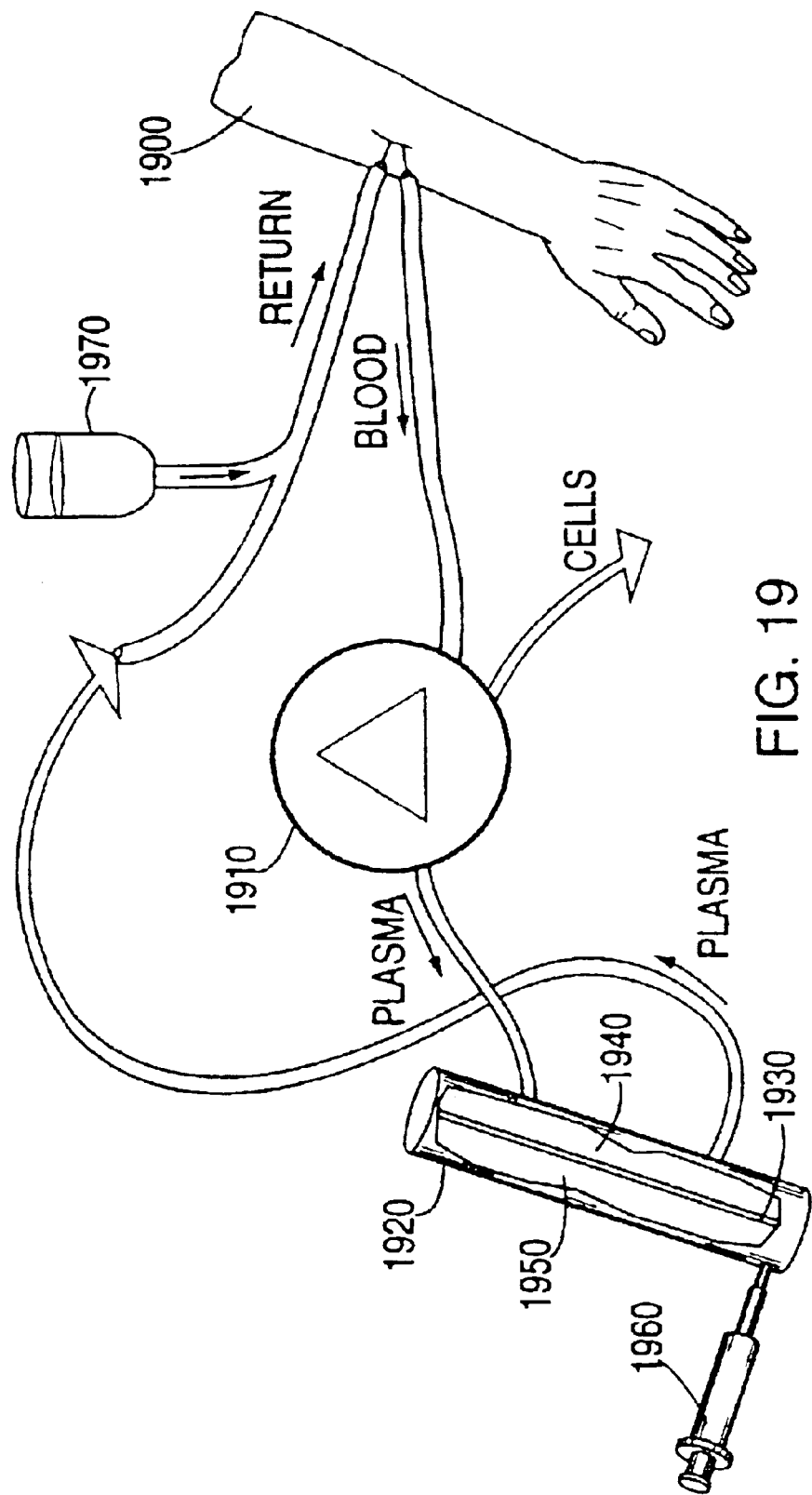
FIG. 19 illustrates a perspective view of an improved hemodialysis system of the present invention and improved method of hemodialysis.

FIG. 19 illustrates a perspective view of an improved hemodialysis system of the present invention and improved method of hemodialysis. Blood is taken from a site for circulatory access (shown here as arm 1900) and transported into a cell-plasma separator 1910. The plasma is then transported to a dialysis chamber 1920 and is divided into at least two compartments that are separated by a semipermeable membrane 1930. One side of the membrane 1930 is the patient's plasma 1940 and on the other side is the dialysate 1950. Selected molecules exchange across the membrane 1930 depending on the characteristics of the membrane (charge, pore size, etc.). The device 1960 comprises a device for adding lipid acceptors to the dialysate and for sampling the dialysate to allow assays of cholesterol, phospholipid, and other components, such as acceptors, specific lipoproteins, specific components, and to monitor treatment. Extraction of plasma cholesterol or other extractable material comprises several possibilities: 1) acceptors are disposed in the dialysate that do not cross membrane 1930 into plasma; 2) the acceptors do cross membrane 1930 and are either left in the plasma and returned to the patient or are separated from plasma before it is returned to the patient; and/or 3) immobilized acceptors on a sheet (such as membrane 1930 itself), on beads, and/or on the walls of the chamber 1920. Plasma thus treated is returned to the patient, usually after having being re-mixed with the blood cells. As noted, cholesterol acceptors can be added at any stage, as an example, a device 1970 comprises acceptors and for adding acceptors to plasma shortly before its return into the patient is also illustrated in FIG. 19. It is further understood that contaminating cellular material, such as platelets, in the plasma will also become cholesterol depleted in endogenous lipids and enriched in phospholipid. It is further understood that all acceptors mentioned throughout this application may accept molecules in addition to cholesterol and may donate material as well.

The cellular concentrate from the cell-plasma separator 1910 can then be treated in any of several ways before being returned to the patient: 1) returned to the patient with no further treatment (this includes being mixed with plasma that has been treated as above); 2) transferred to a second dialysis chamber (not shown) in which the dialysate contains cholesterol acceptors to lipid deplete the cells of endogenous lipids, such as cholesterol, before their return to the patient; 3) mixed with a suspension or solution of lipid acceptors to lipid deplete the cells of endogenous lipids, then either returned to the patient with the acceptors or option 1) and option 2) above can be performed with all cell types together, or after further separation into specific cell types (for example, purified platelets could be lipid depleted of endogenous lipids, such as cholesterol, and enriched in liposomal lipids). Options 2) and 3) can be performed with periodic assays of cellular cholesterol, phospholipid, fluidity, viscosity, fragility, cell composition and/or cell function. Devices 1960, 1970 include an apparatus that allows for the periodic sampling of cells during treatment. As with plasma, lipid acceptors can be added at any stage of the treatment. All fluids, e.g. plasma and concentrated cells, are moved by gravity, mechanically, by manual manipulation (a syringe), or with pumps as needed. Of course, it is understood that blood can be drawn for processing from any appropriate part of the body.

Figure 20:
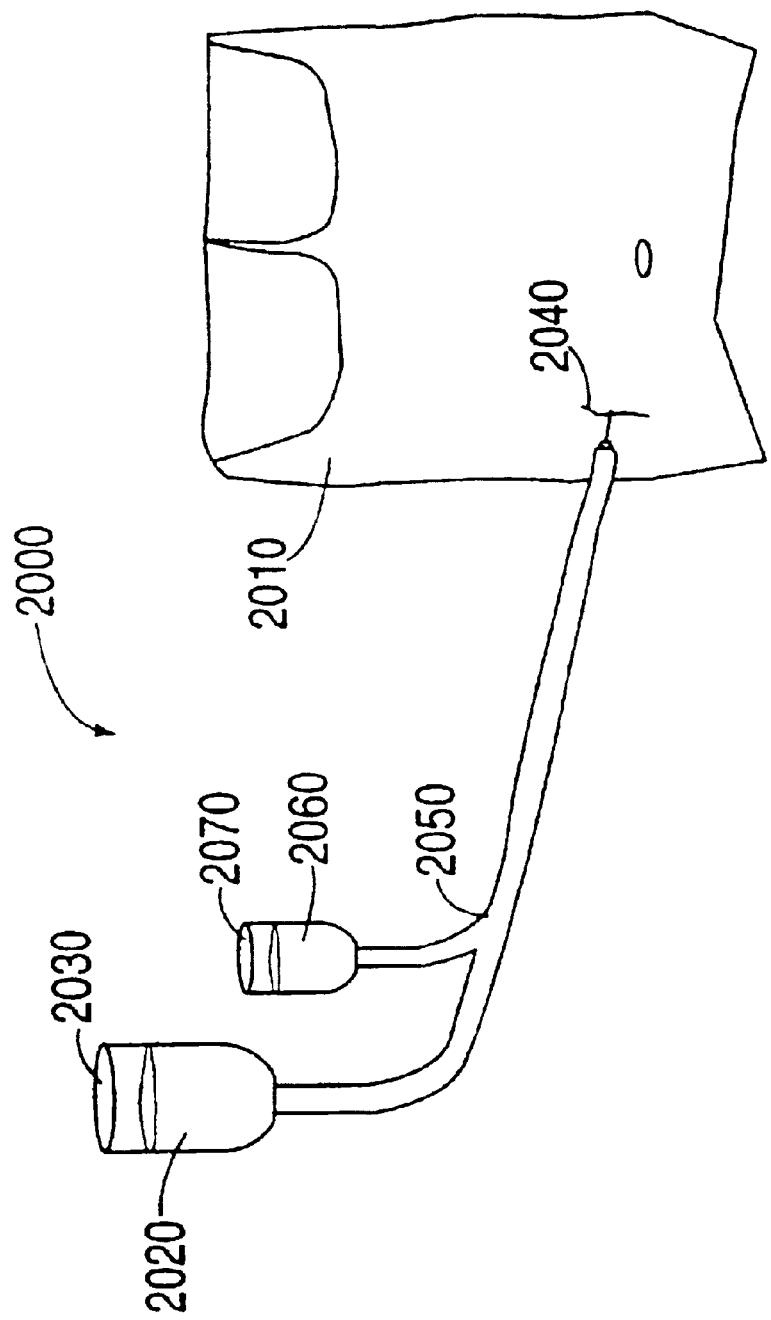
FIG. 20 illustrates a perspective view of an improved peritoneal dialysis system 2000 and method of peritoneal dialysis.

FIG. 20 illustrates a perspective view of an improved peritoneal dialysis system 2000 and method of peritoneal dialysis. Patient's abdomen 2010 (FIGS. 20–21) receives peritoneal dialysate 2020 stored in container 2030 into the peritoneal cavity through incision 2040 by way of channel 2050. Lipid acceptors and/or cholesterol acceptors 2060 are optionally disposed in container 2070. In another variant, lipid acceptors are added to dialysate 2020; added to container 2030 in concentrated form shortly before infusion; added as shown to the stream of fluid entering the peritoneal cavity; or infused by a separate portal of entry into the patient by any effective route. Throughout this application, it is understood that all acceptors may accept molecules in addition to cholesterol and may donate material such as phospholipids and anti-oxidants.

Figure 21:
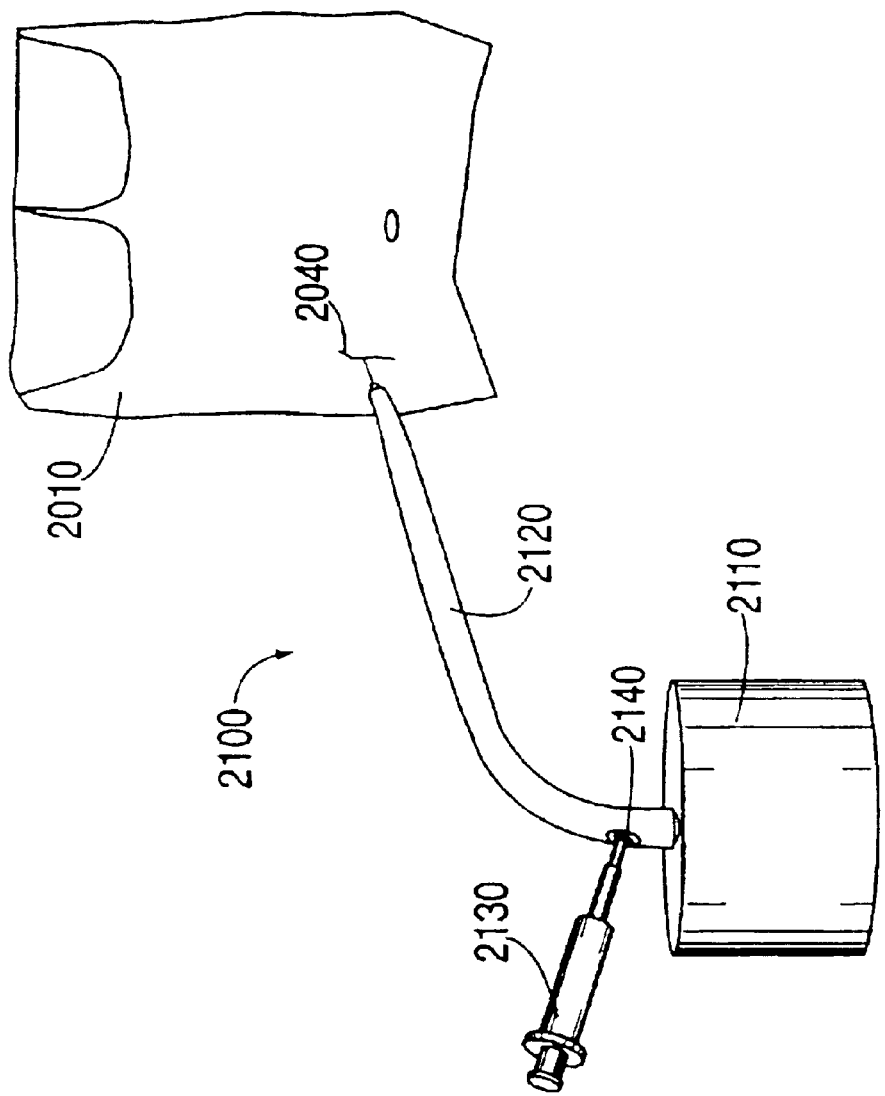
FIG. 21 illustrates a perspective view of a variant of an improved peritoneal dialysis system with assaying means 2100 and method of peritoneal dialysis and analysis of spent fluid.

FIG. 21 illustrates a perspective view of a variant of an improved peritoneal dialysis system with assaying means 2100 and method of peritoneal dialysis and analysis of spent fluid. Container 2110 accepts spent fluid from abdomen 2010 by way of channel 2120. The device 2110 provides access to diagnostic samples of spent dialysate to allow for assay of cholesterol, phospholipid, and other parameters as described herein showing the efficacy of the treatments described. Optionally, assay syringe 2130 is inserted by way of access portal 2140 into channel or tube 2120, or into container 2110, and optional pumps (not shown) are used to move the various fluids to appropriate locations for assay thereof.

Figure 22:
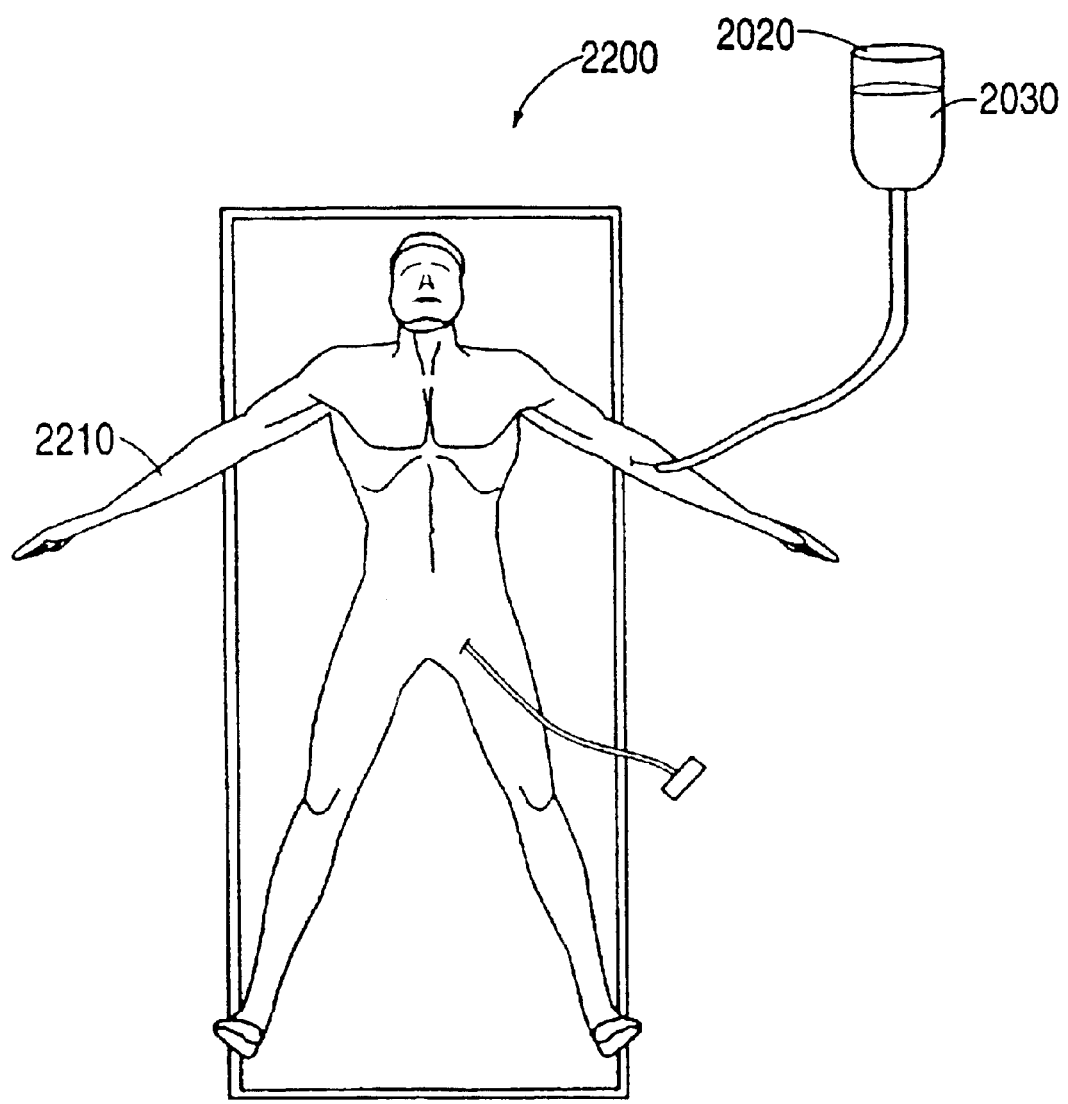
FIG. 22 illustrates a perspective view of an improved cardiac catheterization and/or angioplasty system 2200 and method of cardiac catheterization and/or angioplasty.

FIG. 22 illustrates a perspective view of an improved cardiac catheterization and/or angioplasty system 2200 and method of cardiac catheterization and/or angioplasty. Patient 2210 undergoes cardiac catherization and/or angioplasty. The patient intravenously receives effective doses of lipid acceptors or cholesterol acceptors 2230 co-administered with the treatment(s) from container 2220. Intraarterial access of a catheter for coronary angiography and/or angioplasty allows for ready co-administration of cholesterol acceptors and administration of diagnostic agents such as cholinergic agents, to assess vascular function.

Figure 23:
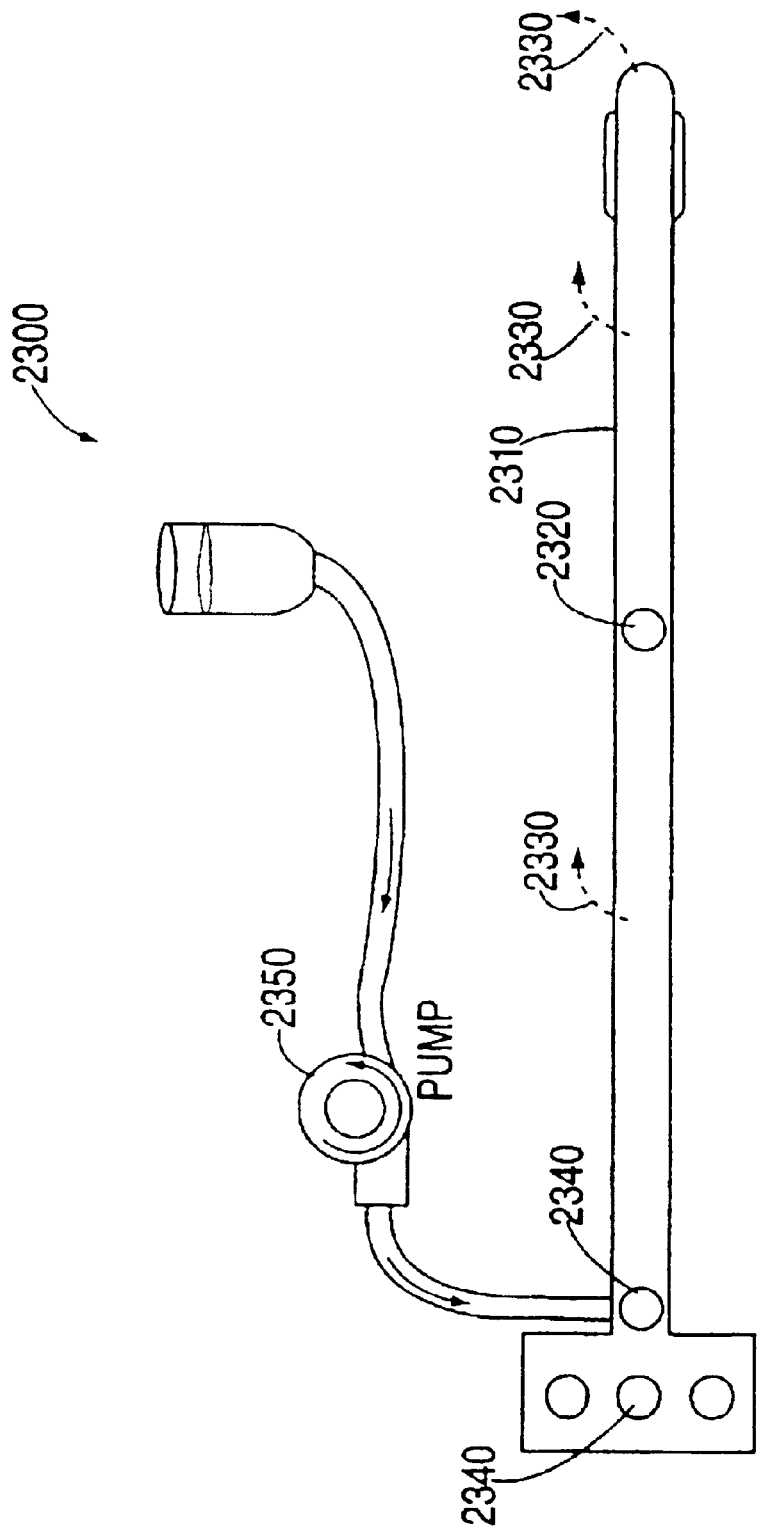
FIG. 23 illustrates a perspective view of a variant of an improved cardiac catheterization and/or angioplasty system 2300 and method of cardiac catheterization and/or angioplasty.

FIG. 23 illustrates a perspective view of a variant of an improved cardiac catheterization and/or angioplasty system 2300 and method of cardiac catheterization and/or angioplasty. Catherization and/or angioplasty catheter 2310 has apertures 2320 that allow for the egress of cholesterol acceptors therefrom. In a variant, catheter 2310 has a permeable membrane that allow for the egress for cholesterol acceptors therefrom. Phantom arrows 2330 indicate egress sites for cholesterol acceptors and/or diagnostic agents. Sites 2340 indicate entry sites for the acceptors or agents. The balloon on the device 2300 can be replaced or supplemented with other devices or can form an inner balloon layer disposed within an outer balloon layer. The acceptors are disposed between the inner and outer flexible balloon layers. Upon expansion of the inner balloon layer a force is exerted against the fluid or gel-like acceptors forcing the acceptors out of the sites 2320, and into direct contact (forcefully) against arterial lesions more locally directing the treatment. It will be appreciated that this variant of the invention provides for maximal penetration of the acceptors into the arterial lesions. The infusions can be accomplished by gravity, manual manipulation of a syringe, or by mechanical infusion pump 2350. The same method and system can be utilized with standard vascular imaging techniques or vessels that include the femorals, carotids, and mesenteric vessels by way of example.

Patient 2210 undergoes cardiac catherization and/or angioplasty. The patient intravenously receives effective doses of cholesterol or lipid acceptors 2230 co-administered with the treatments(s) from container 2220. Intraarterial access of a catheter for coronary angiography and/or angioplasty allows for ready co-administration of lipid or cholesterol acceptors and administration of diagnostic agents such as cholinergic agents, to assess vascular function.

Container 2110 accepts spent fluid from abdomen 2010 by way of channel 2120. The device 2110 provides access to diagnostic samples of spent dialysate to allow for assay of cholesterol, phospholipid, and other parameters as described herein showing the efficacy of the treatments described. Optionally, assay syringe 2130 is inserted by way of access portal 2140 into channel or tube 2120, and optional pumps (not shown) are used to move the various fluids to appropriate locations for assay thereof.

Figure 24:
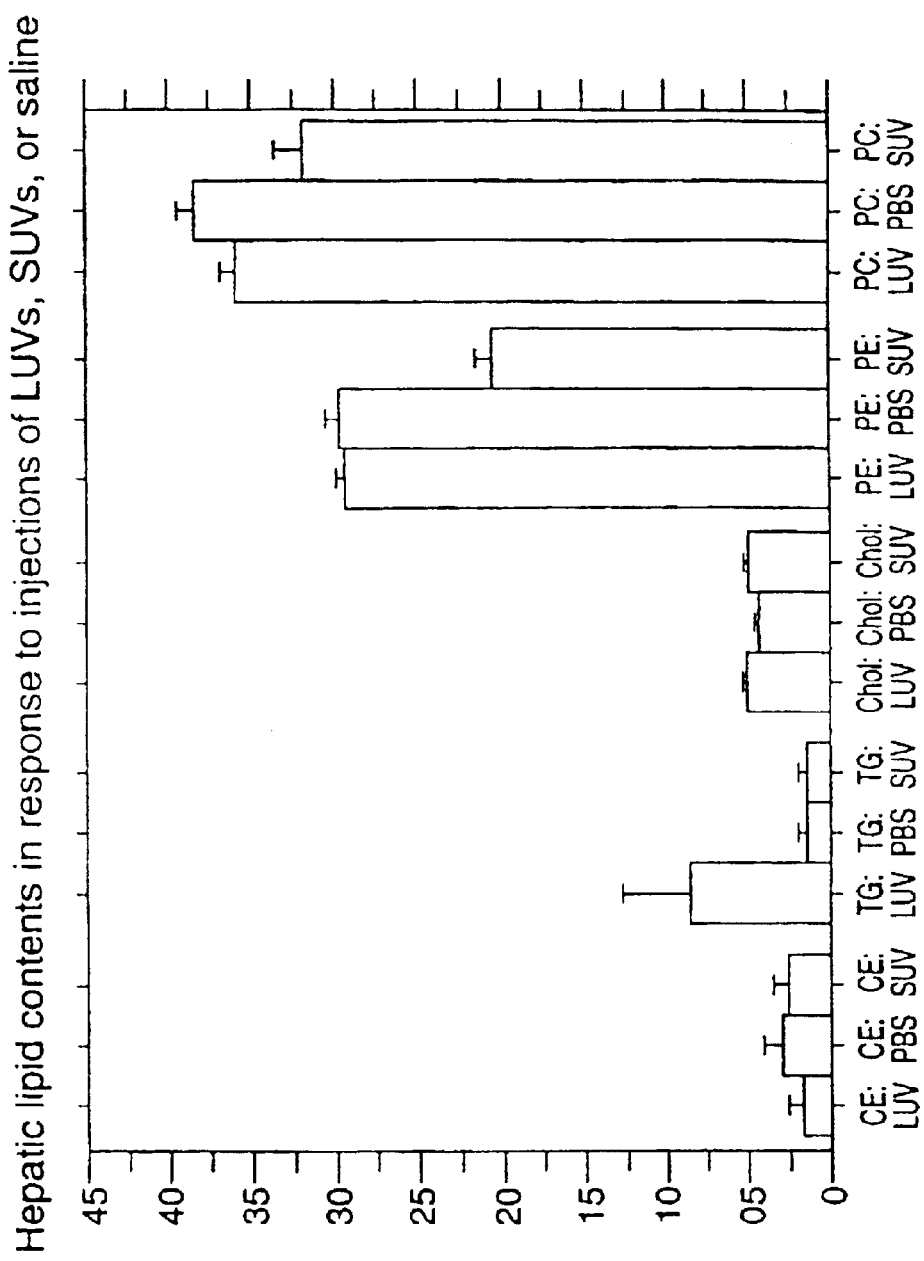
FIG. 24 illustrates a graph of hepatic lipid contents in response to injections of LUVs, SUVs, or saline.

FIG. 24 illustrates a graph of hepatic lipid contents in response to injections of LUVs, SUVs, or saline. The experimental details are as outlined above. Liver samples were assayed for contents of several lipids: cholesterol ester (CE); triglyceride (TG); unesterified cholesterol (Chol); phosphatidylethanolamine(PE); and phosphatidyl choline (PC), which are displayed in units of µg (micrograms) lipid/mg. Lower values of PE and PC in the SUV-treated animals were produced; thus, the Chol:phospholipid ratios in these animals was higher than in the other groups.

Figure 25:
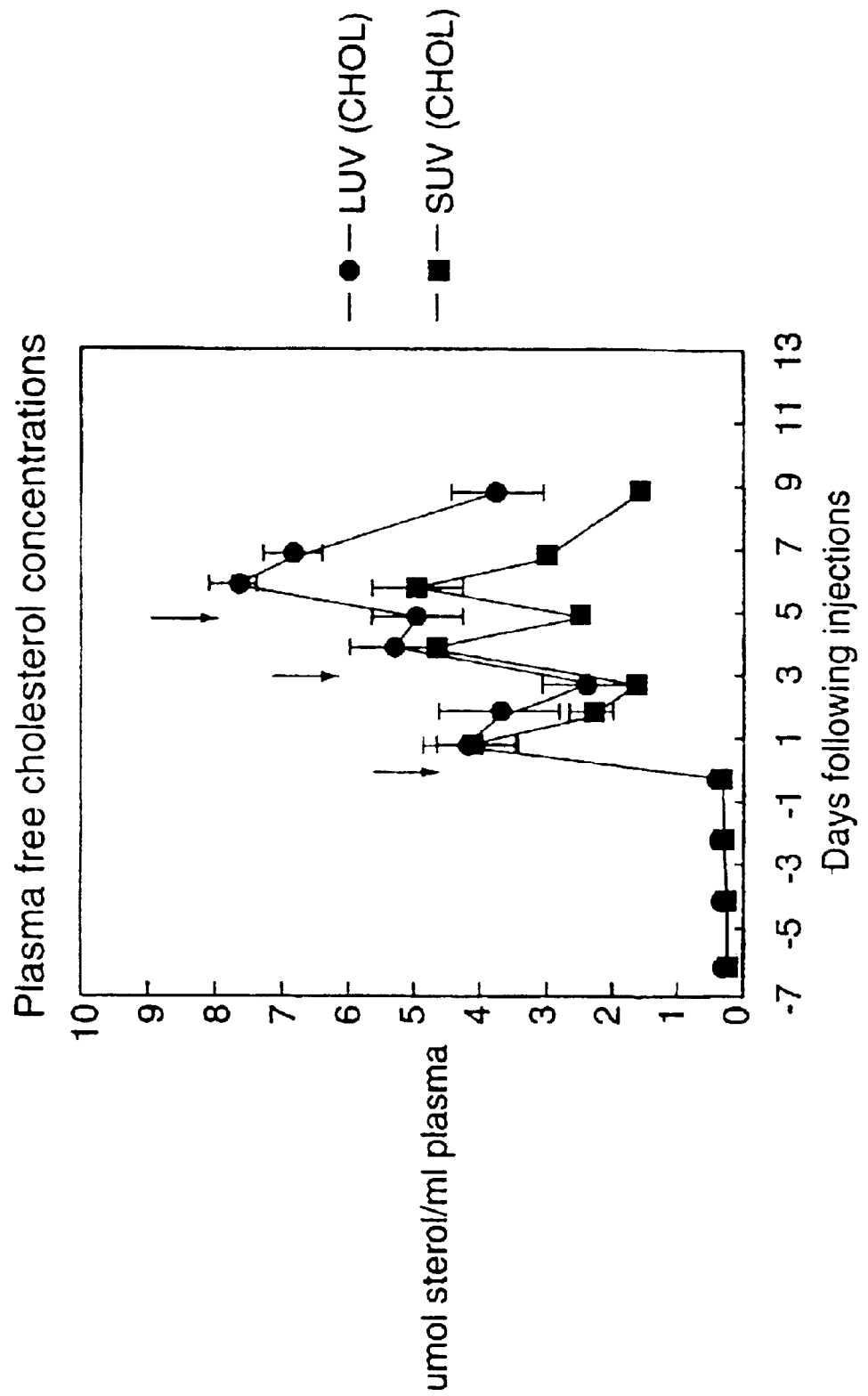
FIG. 25 illustrates plasma free cholesterol concentrations following repeated injections of SUVs or LUV (300 mg/kg) in NZW rabbits.

FIG. 25 illustrates cholesterol ester concentrations following repeated injections of SUVs or LUVs (30 mg/kg) in NZW rabbits (New Zealand White rabbits). The arrows indicate times of phospholipid injection here on days 0, 3 and 5. For a given phospholipid dose, LUVs promote a greater rise in plasma free cholesterol concentrations.

Figure 26:
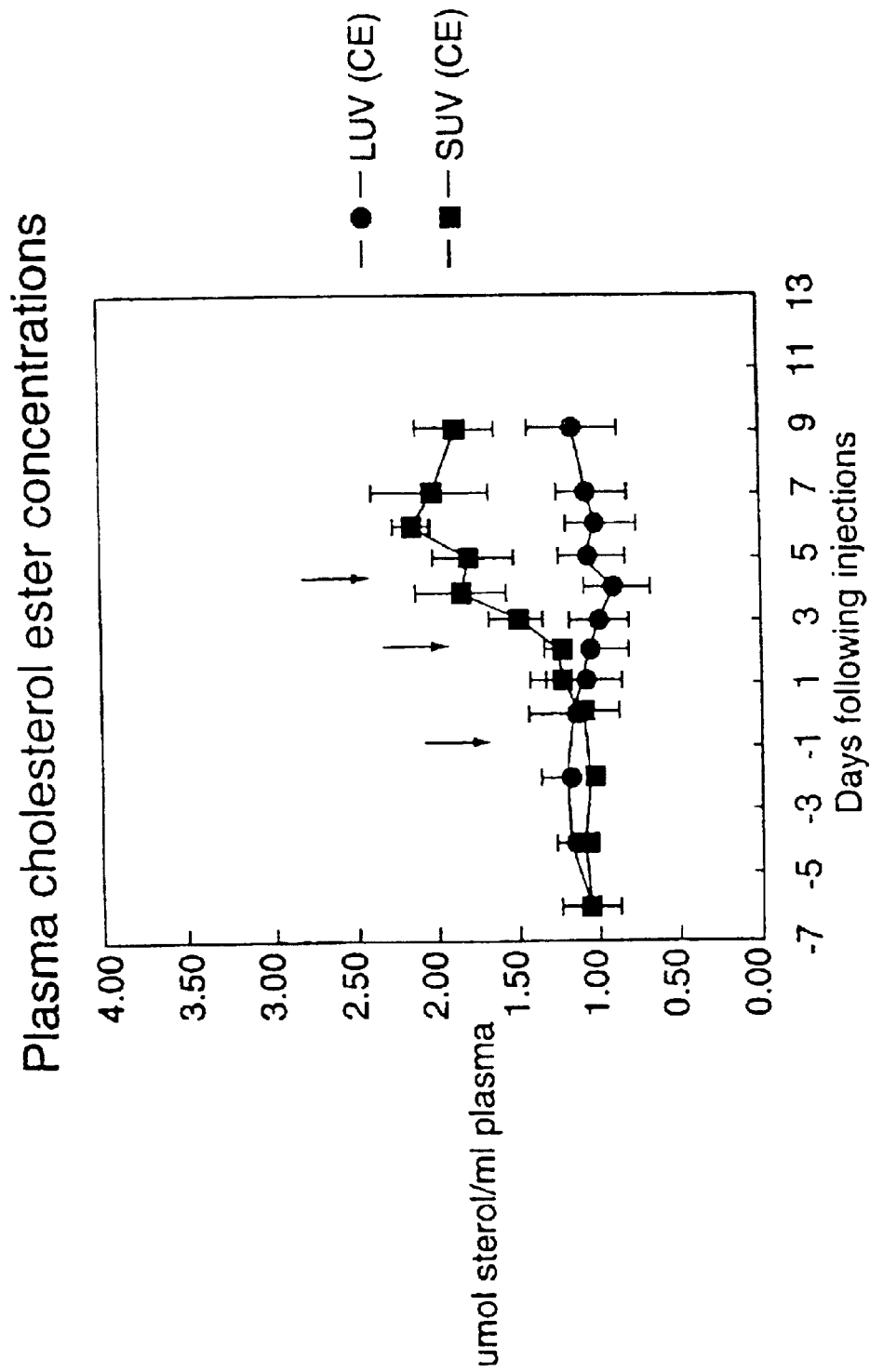
FIG. 26 illustrates plasma cholesterol ester concentrations following repeated injections of SUVs or LUV (300 mg/kg) in NZW rabbits.

FIG. 26 illustrates plasma free cholesterol concentrations following repeated injections of SUV or LUV (300 mg/kg) in NZW rabbits in the same experiment as in FIG. 25, arrows indicate times of phospholipid injection. Repeated injections of LUV, unlike SUV, do not provoke a dramatic rise in CE concentrations in plasma.

The rise in plasma CE concentrations that results from the delivery of excess cholesterol to the liver may be the consequence of two processes. It may involve an over production of CE-rich particles or an impaired clearance of CE-rich lipoproteins. Over production of CE-rich particles that occurs following SUV infusions may result in the plasma or in the liver. In plasma, LCAT acts on small unilamellar phospholipid vesicles or on phospholipid enriched HDL generating CE which may be subsequently transferred by CETP onto LDL. The results with gel filtration of plasma from animals treated with SUVs indicate that CE is carried mostly or substantially on LDL. Also, in plasma, removal of apoE from VLDL by SUVs will slow the clearance of VLDL, thereby favoring a more efficient conversion into LDL. In the liver, the increased delivery of cholesterol to hepatocytes during cholesterol mobilization stimulates an over secretion of apoB, CE-rich lipoproteins.

In a variant, the rise in plasma CE concentrations observed is the result of an impaired clearance of CE rich atherogenic lipoproteins. Intravenously administered liposomes that acquire apoE compete with LDL for LDL-receptor mediated uptake. The delivery of excess cholesterol to the liver down regulates LDL receptors. The processes responsible for an increase in plasma CE concentrations are different between the two liposome preparations. LUVs, unlike SUVs, do not provoke a rise in plasma CE concentrations. LUVs are superior preparations for mobilizing tissue cholesterol without harmful side effects.

A method described above and composition of the present invention also provides enrichment of HDL cholesterol esters by SUVs. One contributing process is the stimulation of lecithin cholesterol acyl transferase (LCAT) and other processes related thereto. The ability of SUVs to increase HDL cholesterol ester is the result of stimulation of LCAT and other processes related thereto. LCAT need phospholipid and cholesterol to generate cholesteryl ester and lysophosphatidylcholine;liposomes can supply extra phospholipid. The present invention also provides for alterations in lipoprotein (LDL, HDL, etc.) composition and function by LUVs and/or SUVs and/or other acceptors.

The liposome compositions described herein and methods utilizing same also include the liposomes picking up endogenous apoE and hence blocking cellular uptake of LDL. The liposomes pick up apolipoproteins, such as apoE and apoA-I, and that this alters or enhances their functions. For example, the uptake of endogenous apoA-I enhances the ability of liposomal derived phospholipid to pick up cholesterol, and the uptake of endogenous apoE would allow the liposomes to block certain pathways for arterial uptake of lipoproteins. All of this is in the context of controlling LDL levels and hepatic gene expression and cholesterol homeostasis.

LUVs and SUVs deliver cholesterol to different regulatory pools within the liver. This conclusion is supported by the differences in hepatic gene responses and CETP mRNA is suppressed: the LDL receptor mRNA is unaffected or increased by LUVs but suppressed by SUVs; and CETP is suppressed by LUVs, but unaffected by SUVs. Further, it is understood that the arterial lesions referenced herein include, by way of example, critical stenoses.

The key points about LUVs and atherosclerosis are illustrated in FIG. 9. The practical benefits of using LUVs as a treatment for atherosclerosis are that they are straight forward to manufacture, and non-toxic even at very high doses. Mechanistically, LUVs promote reverse cholesterol transport in vivo without provoking a rise in LDL concentration, and LUVs are an optimal preparation.

The compositions that are used herein can direct clearance away from hepatic parenchymal cells. And the various methods described herein are utilized with slow infusions of the compositions described, so that hepatic cells are not cholesterol overloaded even if clearance by parenchymal cells occurs. Further, HDL is also controlled by CETP gene suppression.

As described herein assays are performed by: assaying fasting plasma triglyceride to estimate VLDL concentrations; assaying plasma cholesterol (free and ester, or total minus free=ester); precipitating LDL (& VLDL) with polyanions-cations; assaying the supernatant which is HDL; and computing LDL's (whole plasma value minus VLDL-HDL) sterol (or sterol ester) in whole plasma. Liposomes will precipitate with polyanions-cations; or optionally assaying the ester which liposomes mostly lack. Other assays include electrophoresis, chromatography, immune assays, electron microscopic assays, functional assays, structural assays, and compositional assays.

In the dialysate of the present invention, any liposomes or emulsions could be used as long as it's a cholesterol acceptor and either it does not raise LDL or it is not returned to the patient's circulation. In either case, one would need to assay plasma LDL and the plasma concentration of the acceptors, and plasma concentrations of other atherogenic lipoproteins.

With respect to a method described aboves that require delivering the cholesterol to the liver at a slow rate, or in low doses administration might permit small acceptors, such as SUVs, to be used without LUVs provided LDL levels as levels of other atherogenic lipoproteins are monitored and regulated. To avoid disrupting hepatic cholesterol homeostasis, the entrapped drug as described herein need not be given at low doses, but rather the encapsulating liposome or emulsion is given in low doses; the drug could be present at high amounts within a small number of liposomes or a small mass of liposomal lipid.

Alterations in HDL size, composition and function can be accomplished by administering high or even truly low doses of large and/or small liposomes that have little or no sterol. Liposomes without sterol, when given in low doses are easily broken apart by HDL and HDL apolipoproteins and then pieces are incorporated into the HDL fraction of plasma enriching it in phospholipid. Such small doses, e.g. 10–100 mg/kg/dose, even of SUVs without LUVs or drugs to lower LDL levels, are unlikely to raise plasma LDL levels, although periodic monitoring would be prudent.

Also, a method described above as disclosed herein of altering LDL composition without increasing LDL concentration would be to enrich the composition with phospholipids, like POPC (palmitoyloleylphosphatidylcholine), that are resistant to oxidation, enrich the composition with anti-oxidants, deplete unesterified cholesterol, and reduce cellular or arterial uptake of oxidized LDL by phospholipid enrichment.

Liposomes up to about 1000 NM or so would work in the present invention. Larger liposomes would also work but extraction of tissue lipoprotein may be less efficient. It is further possible to concentrate or dry compositions of the present invention. These preparations are then diluted or reconstituted at the time of therapy or administration. In this variant, a two component kit comprising the active material and a dilutent is provided. Inclusion of phosphatidyl glycerol (PG) to make the liposomes negatively charged, or charge other components of the composition, to prevent aggregation during storage is also provided.

Figure 27:
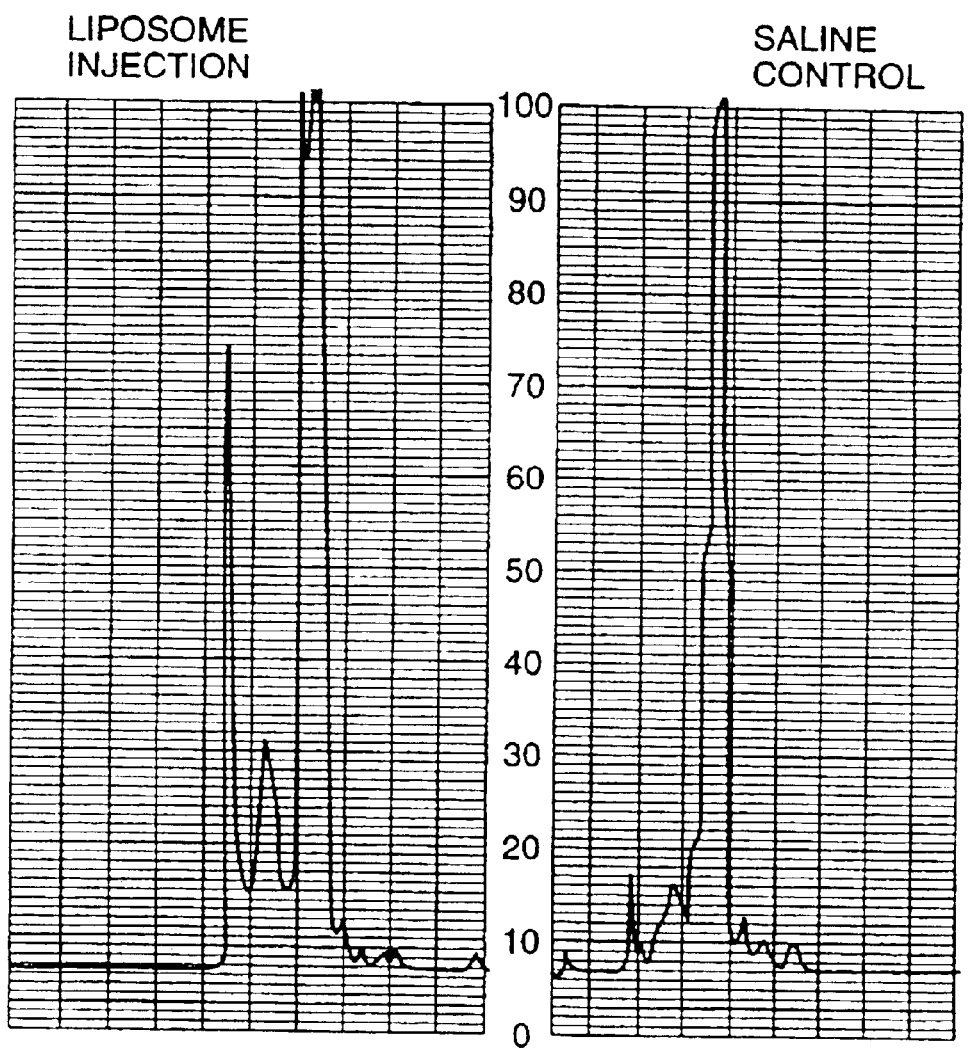
FIG. 27 illustrates alternations in plasma components after repeated injections of SUVs.

FIG. 27 illustrates alterations in plasma components after repeated injections of SUVs. Watanabe Heritable Hyperlipidemic (WHHL) rabbits were given intravenously 1000 mg of SUV phospholipid per kg of body weight, or the equivalent volume of saline, on Monday, Wednesday, & Friday of each week for three weeks (nine doses total). Three days after the final dose, blood samples were taken, and plasma components were fractionated by size by passage over a Superose-6 gel-filtration column. Eluents were read by an in-line spectrophotometer. The tracing on the right is from a saline-injected rabbit, and shows VLDL around fractions #17–18, and LDL around fraction #27. The tracing on the left is from an SUV-injected rabbit, and shows VLDL with persistent liposomes around fraction #16, and LDL-sized particles around fraction #25. The tracings indicate an increase in the amount of LDL-sized particles after repeated injections of SUVs, consistent with an increase in LDL, which is a harmful effect. Because WHHL rabbits have a genetic lack of LDL receptors, this result indicates that SUVs disrupt hepatic cholesterol homeostasis not just by suppressing LDL receptors (FIG. 5), but also by mechanisms independent of LDL receptors (FIG. 27). LUVs avoid both LDL receptor-dependentand —independent disruptions.

Figure 28:
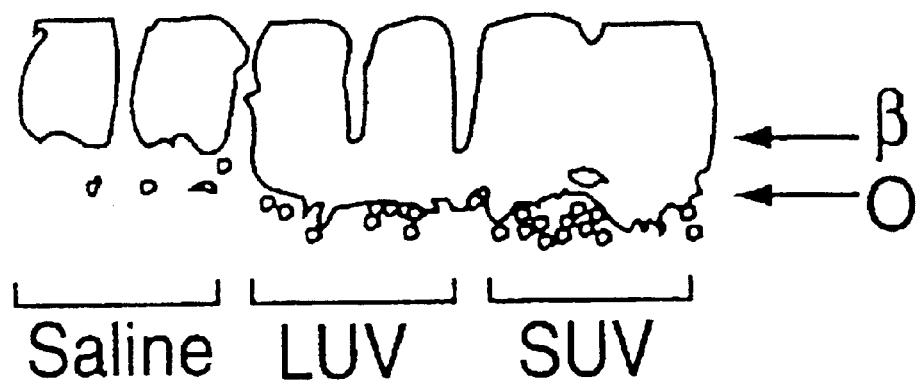
FIG. 28 illustrates an agarose gel electrophoresis of whole plasma following repeated injections of LUVs, SUVs, or saline.

FIG. 28 illustrates an agarose gel electrophoresis of whole plasma following repeated injections of LUVs, SUVs, or saline. Experimental details are referenced in FIGS. 2–8 & elsewhere herein. Four-$\mu$L plasma samples from two rabbits in each group at day 6 were electrophoresed through 1% agarose then stained for lipids with Sudan black. O: origin. β: migration of an LDL standard. The SUV-mediated increase in LDL concentration is illustrated by the darker but otherwise unremarkable p-band in those lanes. SUVs in plasma exhibited a mobility ahead of LDL, owing to their acquisition of plasma proteins, chiefly from HDL. In contrast, plasma LUVs exhibited essentially the same mobility as freshly prepared, protein-free vesicles, i.e., just above the origin (O), indicating a substantial absence or reduction of acquired proteins on the LUVs.

Based on the electrophoretic mobilities in FIG. 28, quantification of the acquisition of protein by LUVs versus SUVs was obtained. LUVs and SUVs were incubated with human HDL in vitro for 4 hours at 37° C., then separated from the HDL by gel filtration chromatography and assayed for protein and phospholipid. LUVs acquired 1.09 $\mu$g of protein per mg of liposomal phospholipid, whereas SUVs acquired 40.4 $\mu$g/mg, i.e., almost 40 times as much. Thus, the two types of liposomes exhibit a striking quantitative difference in protein adsorption. SUVs, but not LUVs, avidly strip apoE from VLDL, thereby slowing its clearance from plasma and favoring its conversion to LDL. In addition, adsorbed proteins play a role in directing the SUVs into a hepatic metabolic pool that disrupts hepatic cholesterol homeostasis, whereas LUVs are not directed into such a pool. Liposomes, emulsions, or any other particles or compounds that extract tissue lipids but do not acquire large amounts of plasma proteins behave similarly to LUVs in these regards.

Specific vascular genes affected by cholesterol loading of cells include genes for prolyl-4-hydroxylase; hnRNP-K; osteopontin (there may be a role for oxidized lipids in provoking arterial calcifications); and Mac-2. A method described aboves of regulating these genes described herein effect restoration of normal vascular or arterial function. Elevated expression of prolyl-4-hydroxylase (an enzyme in the synthesis of collagen, a component of fibrotic plaques) and hnRNP-K (identified in pre-mRNA metabolism and cell cycle progression) messages were found in aortic smooth muscle cells after cholesterol feeding. These would normalize after the liposome treatments described herein. Other genes or enzymes that are abnormal with cholesterol-loading and should normalize with liposome treatment as described herein include osteopontin, nitric oxide synthase (NOS), adhesion molecules, chemoatractants, tissue factor, PAI-1 (plasmidigen activator inhibitor), tPA (tissue plasmidigen activator) and Mac-2 (Ramaley et al. 1995). Other genes affected by cholesterol, cholesterol loading, oxidized lipids would also be corrected.

Many examples of small acceptors such as SUVs, apolipoprotein-phospholipid disks, and HDL are commercially available and can be used in the invention. Kilsdonk EP et al. Cellular cholesterol efflux mediated by cyclodextrins, J. Biol. Chem. 270:17250–17256, 1995. By way of further example, another small acceptor includes the cyclodextrins. Small acceptors (specifically HDL) shuttle cholesterol from cells to liposomes. Cyclodextrins and also other small acceptors can shuttle cholesterol and other exchangeable material from cultured cells to LUVs, which substantially increases the removal and donation of material between cells and LUVs.

Examples of anti-hyperlipidemic drugs include fibric acid derivatives, HmG CoA reductase inhibitors, Niacin, probucol, bile acid binders, other drugs and combinations thereof. Anti-hyperlipidemic treatments also include LDL, apheresis, ileal bypass, liver transplantation and gene therapy.

The data presented in this application support three possible explanations for the difference in metabolic response to LUVs versus SUVs. The three mechanisms act separately or in combination. First, LUVs are taken up largely by Kupffer cells, whereas SUVs are primarily directed towards hepatic parenchymal cells. This is partly a mechanical consequence of hepatic architecture: hepatic endothelial fenestrae are oval openings of about 100×115 nm, through which SUVs of 30-nm diameter or so can readily pass and gain access to parenchymal cells. Large particles, such as large liposomes, of sufficient diameter will not pass easily, and are cleared instead by the macrophage Kupffer cells that line the liver sinusoids. While SUVs also have access to Kupffer cells, their sheer number (—10 times as many SUVs as LUVs per mg of phospholipid) appears to saturate the reticuloendothelial system, and so parenchymal cells predominate in their clearance. Other methods to direct artificial particles away from parenchymal cells are also available, such as by changing the particle structure or composition, including charge and specific ligands for cell-specific binding.

Cholesterol clearance pathways mediated by parenchymal versus Kupffer cells have distinct metabolic consequences. Direct delivery of cholesterol to parenchymal cells by SUVs suppresses sterol-responsive messages (FIGS. 5, 6, & 8). Delivery of cholesterol to Kupffer cells can be followed by gradual transfer of lipid to parenchymal cells, for example, via the extensions of Kupffer cells that reach down through the space of Disse to make physical contact with parenchymal cells. The rate of sterol delivery to the parenchymal cells by transfer from Kupffer cells can be slower than by direct uptake; the chemical form of the sterol may be altered by the Kupffer cells before transfer; there is other cell—cell communication; and, based on other pathways for lipid transfer amongst liver cells, the process of transfer from Kupffer to parenchymal cells may be regulated, whereas SUV clearance does not appear to be.

The second contributing explanation for the difference in metabolic response to LUVs versus SUVs is based solely on differences in the kinetics of their delivery of cholesterol to the liver. LUVs are cleared from plasma somewhat more slowly than are SUVs, and thereby produce a relatively constant delivery of cholesterol mass to the liver from the time of injection until the bulk of injected material is cleared. SUVs are cleared more rapidly, thereby delivering a large bolus of cholesterol mass to the liver several hours after each injection, which is followed by the sustained rise in plasma concentrations of cholesteryl ester and atherogenic lipoproteins. The slow, steady delivery by LUVs avoids disrupting hepatic cholesterol homeostasis, while the more rapid uptake of SUV cholesterol overwhelms the ability of the liver to maintain homeostasis, thereby provoking suppression of hepatic LDL receptors. Other methods to deliver artificial particles or their components to the liver at a proper rate are also available, such as by changing the particle structure or composition, including charge and specific ligand for cell-specific binding.

The third contributing explanation is based on the striking quantitative difference in protein adsorption between the two types of vesicles (FIG. 28), which, in that particular experiment, was a result of their distinct surface curvatures. Thus, SUVs, but not LUVs, would avidly strip apoE from VLDL, thereby showing its clearance from plasma and favoring its conversion to LDL. SUVs that acquire apoE will compete with VLDL, LDL, and other particles for receptor mediated uptake by the liver. Also, adsorbed apoproteins can play a role in directing phospholipid vesicles to different hepatic metabolic pools. Other methods to reduce protein uptake by artificial particles are also available, such as by changing the particle structure or composition, including charge and specific ligands for cell-specific binding.

Overall, given the observation that cholesteryl ester and LDL concentrations do not increase after delivery of large amounts of cholesterol and other exchangeable material to the liver by LUVs, it was apparent that delivery was to a specific metabolic pool or pools with unique properties that do not increase plasma concentrations of atherogenic lipoproteins or harmfully disturb hepatic cholesterol homeostasis, including the regulation of genes and other functions. Thus, these inventions can be regarded in part as a unique delivery system that brings original particle components, such as phospholipid, plus material acquired by the particles, such as cholesterol, to a specific delivery site for harmless disposal and other additional benefits. The delivery system with these characteristics will be useful in any situation whatsoever in which control of hepatic cholesterol homeostasis, hepatic phospholipid homeostasis, and hepatic metabolism in general is advantageous.

For example, in a situation in which it is desirable to modify erthyrocyte lipids, a straightforward approach would be to administer artificial particles that can donate and remove the appropriate lipids. If SUVs are used for this purpose, however, they will transport cholesterol and other material to the liver in a harmful manner, to the wrong pool and/or at the wrong rate, and this will cause increases in plasma concentrations of atherogenic lipoproteins, which is an undesirable side-effect that would preclude this approach. In contrast, the use of large liposomes or other particles with similar properties will result in the proper delivery of original and acquired material, to the proper pool(s) at a proper rate, so that the desired effect (modification of erythrocyte lipids) can be achieved without harmful increases in plasma concentrations of atherogenic lipoproteins.

As another example, it can be desirable to modify infectious agents, such as bacteria, fungi, and viruses, using the compositions and method described herein. Administration of large liposomes or other particles with similar properties will remove and donate exchangeable materials to and from these infectious agents, and then the administered particles will be delivered to the proper pool(s), so that the desired effect can be achieved without harmful increases in plasma concentrations of atherogenic lipoproteins.

As another example, a valuable therapy may provoke an increase in plasma concentrations of atherogenic lipoproteins as an unwanted side-effect. Administration of large liposomes or other particles with similar properties will alter this response through the delivery of lipids and other material to the proper hepatic metabolic pool. The data with the "Mix" animal provides a specific example of this effect (FIG. 4).

There are several mechanisms for affecting arterial uptake, accumulation, and retention of lipoproteins. Liposomes can pick up apoE from atherogenic lipoproteins, thereby reducing lipoprotein binding to arterial cells and also competing for binding to arterial cells. Finally, alterations in LDL size and/or composition affect its binding to extracellular matrix and affect subsequent, harmful alterations within the arterial wall, for example, susceptibility to oxidation or enzymatic modifications.

The action or mode of operation of large acceptors, such as large liposomes, can be aided by small acceptors, and vice-versa, and this applies to both endogenous (e.g., HDL) and exogenous (e.g., apoprotein-phospholipid complexes) small acceptors. Large acceptors penetrate poorly into the interstitial space and appear to inefficiently approach the cell surface under certain circumstances. These effects impede their uptake and donation of exchangeable material from membranes, cells, tissues, organs, and extracellular regions and structures. Small acceptors do penetrate well into the interstitial space and are able to approach the cell surface, thereby allowing efficient uptake of exchangeable material. Small acceptors have major disadvantages, however. They have a very limited capacity to acquire or donate material (even though the initial rate of acquisition or donation is rapid, until their capacity becomes saturated) and, once they have acquired material, they deliver it to the liver in a way that disrupts hepatic cholesterol homeostasis.

Large acceptors and small acceptors together, however, synergistically overcome each other's drawbacks through at least three mechanisms. First, the large acceptors act as a sink (or supply) for exchangeable material, while the small acceptors act as a shuttle that siphons material from peripheral stores to the large acceptors and in the other direction.

Thus, for example, the small acceptors penetrate tissue, acquire (and/or donate) material from the tissue, and their capacity becomes at least partly saturated. They leave the tissue and encounter the large acceptors in the plasma, at which point the small acceptors are stripped of tissue lipids. The capacity of the small acceptors is thereby restored, so that when they return to the tissue, they can acquire (and/or donate) more material. This cycle can continue many times. Second, the large acceptors can re-model some small acceptors. For example, large acceptors can donate phospholipid to HDL, which increases the capacity of HDL acquire tissue cholesterol and other material. Third, as noted elsewhere, the presence of large acceptors can block or reduce the harmful disruptions in hepatic cholesterol homeostasis caused by the small acceptors.

Large liposomes avoid raising plasma concentrations of atherogenic lipoproteins in general, not just LDL. This list includes all lipoproteins that contain apolipoprotein B (apoB), such as LDL, IDL, VLDL, Lp(a), β-VLDL, and remnant lipoproteins.

Immune cells are also the targets for depletion using a method described aboves and modes of operation disclosed herein. It is understood that administration of an HMG-CoA reductase inhibitor, pravastatin, to cardiac transplant recipients reduced their natural-killer-cell cytotoxicity in vitro, reduced episodes of rejection accompanied by hemodynarnic compromise, reduced coronary vasculopathy, reduced plasma LDL levels (and increased HDL levels), and significantly enhanced one-year survival. The effect on survival was dramatic: in the control group, 22% died in the first year, whereas only 6% died in the pravastatin-treatedgroup.

Immunologic effects of HMG-CoA reductase inhibitors have been reported in vitro. These reported immunologic effects include the regulation of DNA in cycling cells, the inhibition of chemotaxis by monocytes, the regulation of natural-killer-cellcytotoxicity, and the inhibition of antibody-dependent cellular cytotoxicity. Regulation of such inhibitors results from changes in circulating lipids or other effects and by utilization of a method described aboves and modes of operation disclosed herein.

HMG-CoA reductase catalyzes an early step in cholesterol biosynthesis and is crucial in the synthesis of molecules besides cholesterol. Adding cholesterol to immune cells treated with HMG-CoA reductase inhibitors does not restore function, although the addition of mevalonate does. Although this suggests that cholesterol depletion is not directly responsible for the immune effects, the use of liposomes or other acceptors to remove cholesterol from cells increases endogenous consumption of mevalonate, as the cells try to make more cholesterol. To impede the ability of the immune or other cells to make up their cholesterol loss by picking up more LDL or other lipoproteins, a method described aboves and treatment described herein are also be done in conjunction with therapies to lower plasma cholesterol concentrations (including HMG-CoA reductase inhibitors, fibric acids, niacin, bile acid binders, LDL-pheresis, etc.).

These processes include enhancement of cholesterol removal and reduction of cholesterol influx. Levels of HDL, the apparent natural mediator of cholesterol removal from peripheral cells, increased in a treated group of patients, and LDL levels were deceased. The administration of HMG-CoA reductase inhibitors in vivo usually causes very tiny changes in reductase enzyme activity: cells simply make more enzyme to overcome the presence of the inhibitor. They also make more LDL receptors (especially in the liver) and so LDL levels fall.

The invention further provides for additives to PD (peritoneal dialysis solutions) that reduce the accelerated atherosclerosis that occurs in renal failure.

Chemotaxis of monocytes is an important early event in atherosclerotic lesion development: monocytes become attracted to abnormal arterial lipid deposits, and to cellular products made in response to the presence of these deposits, enter the vessel wall, transform into macrophages, internalize the lipid by phagocytosis and/or endocytosis, and become a major component of the so-called lipid-rich foam cells of human atherosclerotic lesions. Thus, inhibition of monocyte chemotaxis is important for atherosclerosis as well and can be accomplished using a method described aboves disclosed herein. Both cellular and humoral immunity seem to be affected by reductase inhibition: cardiac rejection accompanied by hemodynamic compromise has often been associated with humoral rejection (i.e., that occurring without producing marked lymphocytic infiltration in endomyocardial-biopsyspecimens).

Pravastatin may interact with cyclosporine [an important immunosuppressive drug], which blocks the synthesis of interleukin-2 in stimulated T-lymphocytes. The addition of interleukin-2 restored the natural-killer-cell cytotoxicity and partly restored the antibody-dependent cytotoxicity that were inhibited in lovastatin-treated in vitro cell cultures. A synergy between cyclosporine and pravastatin explains increased immunosuppression in recipients of cardiac transplants, whereas patients without transplants who receive HMG-CoA reductase inhibitors for hypercholesterolemiado not have clinical immunosuppression.

Thus, the use of safe cholesterol acceptors with other immunosuppressives, such as cyclosporine &/or glucocorticoids (which can also suppress IL-2) is also contemplated by this invention.

It is also appreciated that the invention utilizes derivatives of various compounds described herein.

Pathological specimens from patients with cardiac transplants who have severe coronary vasculopathy have been reported to have a high cholesterol content. Therefore, early cholesterol lowering with pravastatin may play a part in decreasing the incorporation of cholesterol into the coronary arteries of the donor heart. Large liposomes or other cholesterol acceptors are used to accomplish the same effect, quickly and directly, alone or in combination, therewith.

Immune modulations is important in many conditions, not just cardiac transplantation. Areas in which the above approaches could be used also include transplantations of other organs, autoimmune diseases (in which the body's immune system mistakenly attacks the body's own tissues), some infections (in which the immune reaction becomes harmful), and any other situation in which immune modulation would be helpful.

With respect to infections, modification of the lipid content and composition of foreign objects in the body (such as infectious agents) while maintaining normal hepatic cholesterol homeostasis should also be mentioned.

Oxidized lipids alter tissue function and cause damage, including decreased EDRF, and increased adhesion molecules, cell damage, and macrophage chemotaxis.

There are interactions between LUVs and small acceptors, such as HDL, apoprotein phospholipid complexes, and cyclodextrins. Liposomes remodel HDL into a better acceptor by donating extra phospholipid, and the small acceptors act as a shuttle, carrying cholesterol efficiently from cells to liposomes. LUVs do not elevate LDL concentrations and do not suppress hepatic LDL receptor gene expression. The medical utility for LUVs includes restoring EDRF secretion by endothelial cells. High cholesterol levels inhibit endothelial release of EDRF not through cholesterol, but through an oxidized derivative of cholesterol. Because HDL itself restores EDRF release, perhaps through the removal of cholesterol or of oxidized lipids, then liposomes would be able to do the same (the HDL ferries cellular oxidized lipids to liposomes, for example).

The invention provides a method and mode of operation for modifying cellular lipids, including oxidized lipids, without provoking a rise in LDL concentrations or harmfully disturbing hepatic homeostasis. Thus, the LUVs, presumably acting in concert with endogenous (or exogenous) small acceptors of cholesterol (such as HDL), pull oxidized lipids out of peripheral tissues and deliver them to the liver for disposal. Oxidized lipids have a wide range of harmful biological effects, including suppression of EDRF release, induction of cell adhesion molecules, cellular damage, chemotaxis of macrophages, and so forth.

Oxidized lipids and their harmful effects include decrease endothelial C-type ANF; increased endothelial PAI-1 and decreased tPA and decreased endothelial thrombomodulin. Liposomes enhance or participate in this effect. These changes impair the body's ability to dissolve clots. A method described aboves disclosed herein assist in ameliorating these harmful effects of oxidized lipids. HDL acts in part by transporting enzymes that inactivate biologically active oxidized lipids.

It is understood that oxidized LDL inhibits endothelial secretion of C-type natrizuretic peptide (CNP). It is the lipid component of oxidized LDL that mediates this effect. Most importantly, HDL blocks the action of oxidized LDL, presumably by picking up oxidized lipids (e.g., oxidized cholesterol). Coincubation with high-density lipoprotein (HDL), which alone had no effect on CNP release, significantly prevented Ox-LDL-induced inhibition of CNP secretion by endothelial cells (ECs). Analysis by thin-layer chromatography demonstrated that oxysterols, including 7-ketocholesterol, in Ox-LDL were transferred from Ox-LDL to HDL during coincubation of these two lipoproteins. These results indicate that Ox-LDL suppresses CNP secretion from ECs by 7-ketocholesterol or other transferable hydrophilic lipids in Ox-LDL, and the suppressive effect of Ox-LDL is reversed by HDL.

Whatever molecule HDL picks up, the presence of liposomes or other acceptors around as described herein will allow it to do a better job, because of remodeling of HDL by liposomes & shuttling of oxidized lipids by HDL from tissues to liposomes (i.e., the liposomes continuously strip the HDL). Liposomes with an exogenous small acceptor will also work.

It is further understood that transferable lipids in oxidized low-density lipoprotein stimulate plasminogen activator inhibitor-1 and inhibit tissue-type plasminogen activator release from endothelial cells. As above, it is the lipids in oxidized LDL, such as oxidized forms of cholesterol, that produce the effect. It is understood that oxidized low density lipoprotein reduced thrombomodulin transcription in cultured human endothelial cells. It is appreciated that oxidized lipids play a role in atherosclerosis, and enzymes on HDL that inactivate oxidized lipids may contribute to a protective effect. It is contemplated that a method described aboves and compositions disclosed herein will help this proposed mechanism as well, for example, by removing end-products of these enzymes, by otherwise altering HDL, and by providing an additional platform for enzyme transport and action.

As such the use of large liposomes to remove harmful lipids in general (here, oxidized lipids) from peripheral tissues, either directly or via HDL, which would extract the lipids first, possibly inactivate them, then deliver them or their break-down products to liposomes in the circulation is described. Direct methods to assess oxidation and oxidative damage in vivo include for lipids, assays for 8-epiPGF$_2$alpha; for DNA, assess 8-oxo-2' deoxyguanosine; generally assess anti-oxidant enzymes in tissues; and assess anti-oxidants levels, such as vitamin E, vitamin C, urate, and reduced/oxidizedglutathione.

Methods relating to and modes for effecting the reverse lipid transport, from cells, organs, & tissues, including transport of extracellular material, and any exchangeable material in general are described herein. This covers not just cholesterol, but also sphingomyelin, oxidized lipids, lysophophatidylcholine, proteins, and also phospholipid donation. Some effects of oxidized material include increased calcification in arterial cells as described above and below.

Three potential differences between large versus small liposome to explain their different effects on LDL and apoB levels include: fenestral penetration (LUV<<SUV); rate of clearance (LUV<SUV, so that LUVs produce a slow, sustained cholesterol delivery to the liver that may be less disruptive); and protein adsorption (LUV<<SUV).

Unesterfied cholesterol increases tissue factor expression by macrophages. This is extremely important, because it is macrophage-derived tissue factor that makes the material released by unstable, rupturing plaques such a powerful stimulus for a clot to form that then blocks the vessel leading to a heart attack. A method described aboves and modes of operation and compositions of the invention act upon the expression of tissue factor.

Poor absorption of proteins by large liposomes affects LDL levels and/or atherosclerosis by the following mechanisms: 1) acquisition of apoE from VLDL by small liposomes impairs the removal of VLDL from the circulation, thereby allowing it to be more efficiently converted into atherogenic LDL; ii) absorbed proteins on small liposomes direct these particles into the wrong metabolic pool within the liver. Polyacrylamide gel electrophoresis shows that liposomes (actually small liposomes) increase the size of LDL. Liposomes are used to alter LDL size, composition and structure to decrease its atherogenicity.

Other properties of LDL could be changed by administration of liposomes. For example, liposomes reduce surface unesterified cholesterol; reduce surface sphingomyelin; replace surface phospholipids with POPC which is poorly oxidized; supplement the LDL with antioxidants that were added to the liposomes before administration. These changes would substantially alter arterial entry, retention, modification and atherogenicity of LDL.

The side-effects controlled are focused on hepatic cholesterol metabolism, hepatic expression of genes involved in cholesterol metabolism, and plasma concentrations of cholesterol-rich atherogenic lipoproteins that contain apolipoprotein B (chiefly, LDL). Reverse transport of sphingomyelin, for example, changes hepatic cholesterol metabolism (cellular sphingomyelin affects the intracellular distribution of cholesterol, and hence its regulatory effects; also sphingomyelin is a precursor to ceramide, which mediates intracellular signaling), though large liposomes appear to avoid any problems in the area. The same holds true for reverse transport of oxidized forms of cholesterol (they are even more potent that unoxidized cholesterol in suppressing LDL receptor gene expression). Cyclodextrins do not pick up phospholipids.

Liposomes pick up any exchangeable lipid (actually, any exchangeable amphipathic or hydrophobic material, which includes lipid or protein or anything else with these characteristics). This includes sphingomyelin, oxidized or modified lipids, such as oxidized sterols and phospholipids. Typically, such liposomes can pick up unesterified cholesterol and other exchangeable material from other lipid bilayers, such as cell membranes, and from lipoproteins. Liposomes also pick up proteins and donate phospholipids. During and after these modifications, the liposomes are removed from the plasma, chiefly by the liver. Throughout this application, we will refer to this general process as "reverse lipid transport", although it is understood that any exchangeable material in tissues, blood, or liposomes could participate. Specific examples of exchangeable material include unesterified cholesterol, oxidized forms of cholesterol, sphingomyelin, and other hydrophobic or amphipathic material.

These molecules accumulate in atherosclerosis and mediate harmful effects (e.g., cholesterol, oxidized cholesterol, and other material, such as lysophospholipids) or in aging (e.g., sphingomyelin). For example, oxidized lipids, particularly sterols, alter many peripheral tissue functions, including stimulating calcification by arterial cells in atherosclerosis & stimulating endothelial plasminogen activator inhibitor-1 release by endothelial cells; other oxidized lipid products include lysophospholipids that stimulate endothelial expression of adhesion molecules that attract macrophages into lesions, and sphingomyelin accumulates in some cell-culture models of aging and, with cholesterol, may account for some of the cellular changes. Other changed, such as oxidation, may also mediate or accelerate aging. Many of these molecules have been shown to be picked up by liposomes in vitro (e.g., cholesterol, sphingomyelin, & probably oxidized cholesterol) and many by HDL (cholesterol, oxidized cholesterol by liposomes) but it is likely that they pick up these other molecules as well. In terms of total mass, however, the bulk of the acquired material is unesterified cholesterol, with proteins in second place. Alternatively, by acquiring unesterified cholesterol, the liposomes may reduce the amount of oxidized cholesterol that develops, because there will be less starting material.

The effective periods of time described herein should not be interpreted to exclude very long courses of treatment, lasting years, for example. Nor should it exclude repeated courses of treatment separated by weeks, months, or years.

Side effects include overload of the liver with cholesterol or other materials acquired by the liposomes; with subsequent alterations in hepatic function, such as suppression of LDL receptors, stimulation of intrahepatic cholesterol esterification, stimulation of intrahepatic cholesterol esterification, stimulation of hepatic secretion of atherogenic lipoproteins that contain apolipoprotein-B, and impaired uptake of atherogenic lipoproteins by the liver from plasma.

As used herein the word, "endogenous" indicates that the HDL arises from within the body, and is not itself administered. HDL and related acceptors can, however, be administered.

The data indicates another difference between large and small liposomes in vivo. Before injection, the liposomes that are used in our experiments were essentially electrically neutral, indicated by a failure to migrate rapidly through a gel of agarose when an electric field is applied. (This does not imply that charged liposomes or other particles could not be used. The small liposomes pick up proteins and other material, and become electrically charged: they now rapidly migrate through agarose gels when an electric field is applied. Agarose gels of plasma samples we had stored from the three groups of rabbits were run. The small liposomes became more mobile LDL in these gels. The large liposomes were substantially less mobile, indicating a lower charge density, reflecting a lower protein content.

Two explanations for the difference between large and small liposomes exist: 1) small ones penetrate through hepatic endothelial fenestrae while large ones do not (thus, large ones go to Kupffer cells and small ones go to hepatic parenchymal cells and cause problems); 2) large liposomes are known to be cleared by the liver somewhat more slowly than are small liposomes (the reason is not known), and so may not overwhelm the liver as easily. The data on charge density provides an explanation in part: less protein, therefore slower or altered hepatic uptake.

The delivery of cholesterol to the liver by LUVs is actually more efficient than by SUVs, per mg of phospholipid. One difference is that the delivery by LUVs is steady over a long period after the injection, whereas the delivery by SUVs peaks then falls.

Some of the composition described herein include egg phosphatidylcholine; synthetic phosphatidylcholines that are not crystalline at body temperature (e.g., they contain at least one double bond) yet are resistant to oxidation (e.g., they do not have many double bonds, such as 1-palmitoyl, 2-oleyl phosphatidylcholine, abbreviated POPC); other natural or synthetic phospholipids alone or in mixtures; any of the preceding supplemented or replaced with hydrophobic or amphipathic material that still allows a liposomal or micellar structure. An extruder is certainly not the only conceivable method for making large liposomes or even particularly LUVs. Other methods known to practioners in the field are available or can be adapted to make large liposomes in general and LUVs in particular.

As used herein, a dose includes from 10 to 1600 mg of phospholipid, in the form of large liposomes, per kg of body weight. Other acceptable rates described herein can be determined empirically by the response of plasma LDL concentrations.

Where there is a change in membrane composition, as well as function, one can use an assay of membrane composition or an assay of tissue composition. Compositional assays should include lipids, proteins, and other components.

HDL can pick up oxidized material, and HDL-associated enzymes may inactivate oxidized material.

The separations in time will depend on the actual dose of material, its effects on hepatic cholesterol homeostasis, and whether cholesterol-lowering agents are being concurrently administered. Thus, for doses of about 300 mg of small liposomes per kg of body weight, slight disruptions will occur after even a single dose, and single administrations of higher doses may cause even more disruptions. Exemplary separations in time include one day to one month, but the precise schedules would have to be determined by monitoring hepatic cholesterol metabolism and plasma levels od LDL and other atherogenic lipoproteins.

The major macrophages that would be involved in liposomal clearance would be Kupffer cells in the liver and macrophages in the bone marrow or spleen. The catabolism here would be the so-called alternative pathway for initiating the conversion of cholesterol into bile acids (macrophages are known to have at least one cholesterol-catabolizing enzyme), or would be transfer of sterol (enzymatically altered or not) to other cells, such as hepatic parenchymal cells that would then dispose of the molecules.

A method described aboves described herein also control effects of cellular aging.

The invention includes means for assessing the efficacy of liposomal therapy by performing assays of oxidation in vitro and in vivo, assays of oxidative susceptibility of plasma components, and assays of the ability of altered HDL to inhibit oxidation (by binding oxidative products and/or through its paroxinase or other anti-oxidant components), and the ability of HDL or plasma or serum or blood to mobilize cholesterol and other exchangeable material.

Large liposomes may cause the mobilization of some material that is trapped between cells as well (this is the extracellular space). This extracellular material causes problems a) when it contacts cells or platelets, altering their function and b) by simply taking up space.

Estimate rates of cholesterol mobilization can be empirically determined. It is appreciated that the kinetics of liposomal clearance is different in different species (the $t_{1/2}$ of LUVs in mice is about 8 h, but in rabbits it is about 24th, and in humans it is longer). Thus, rates calculated may vary from species to species. Based on my data on injection of 300 mg of SUVs into rabbits, the peak rate of liposomal cholesterol removal from plasma was between 3 h and 6 h after the injection. At that point, the liposomes had raised plasma unesterified cholesterol by just over 2 mmol/L; assuming a total plasma volume of 90 mL in a 3-kg rabbit, the total liposomal cholesterol at that point was 180 $\mu$moles; the $t_{1/2}$ for SUVs in these rabbits was about h, so roughly 10% is removed in 3 h; thus, the peak rate of liposomal cholesterol removal was about 2 $\mu$moles/h/kg, and this caused a subsequent rise in plasma cholesteryl ester concentrations. Notice that at other time periods after the injection, the rate of liposomal cholesterol removal from plasma was less. Note also that the liver is the predominant organ for clearance, but not the sole organ for clearance.

It has been calculated that a single injection of 300 mg LUVs/kg into 20–22-g mice mobilized about 2400 nmoles of cholesterol in the first 24 h after injection. In contrast to the data with SUVs in rabbits, the mobilization of cholesterol during the first 24 h in the mice injected with LUVs was quite steady. This calculates to about 4.7 $\mu$moles/h/kg over this first 24-h period, which is actually more than the above figure of 2 $\mu$moles/h/kg, which was a peak rate. It is not fair comparison, because the clearance of LUVs in mice is three times as fast as in rabbits. If we take 4.7 divided by 3, we get 1.6 $\mu$moles/h/kg, which is less than 2, but these are imperfect estimates. Human rates can be empirically determined. It is clear, however, that LUVs deliver their cholesterol at a steady rate, whereas SUVs make a brief, rapid push of lipid into the liver. At body temperature, the most desirable liposomes are fluid within the confines of the bilayer, which is called the liquid crystalline state. Less desirable are liposomes in the gel state, which is less fluid.

It is understood that unesterified cholesterol stimulates macrophages to express more tissue factor, a substance known to provoke blood clots. This explains the presence of abundant tissue factor in rupture-prone plaques, which, when they rupture, expose tissue factor to plasma and provoke a clot that can occlude the vessel, causing a heart attack. This would be another example of an abnormal cellular function that may be reversed by removal of cholesterol by liposomes.

Several human conditions are characterized by distinctive lipid compositions of tissues, cells, membranes and/or extracellular regions. For example, in atherosclerosis, cholesterol (unesterified, esterified, and oxidized forms) and other lipids accumulated in cells and in extracellular areas of the arterial wall and elsewhere. These lipids have potentially harmful biologic effects, for example, by changing cellular functions and by narrowing the vessel lumen, obstructing the flow of blood. Removal of the lipids would provide numerous, substantial benefits. Moreover, cells, membranes, tissues and extracellular structures would benefit from composition and alteration that include increasing resistance to oxidation and oxidative damages, such as by increasing the content and types of anti-oxidants, removing oxidized material, and increasing the content of material that is resistant to oxidation. In aging, cells have been shown to accumulate sphingomyelin and cholesterol, which alter cellular functions. These functions can be restored in vitro by removal of these lipids and replacement with phospholipid from liposomes. A major obstacle to performing similar lipid alterations in vivo has been disposition of the lipids mobilized from tissues, cells, extracellular areas, and membranes. Natural (e.g., high-density lipoproteins) and synthetic (e.g., small liposomes) particles that could mobilize peripheral tissue lipids have a substantial disadvantage: they delivery their lipids to the liver in a manner that disturbs hepatic cholesterol homeostasis, resulting in elevations in plasma concentrations of harmful lipoproteins, such as low-density lipoprotein (LDL), a major atherogenic lipoprotein.

The invention described herein provides methods and compositions related to the "reverse" transport of cholesterol and other materials and compounds from peripheral tissues to the liver in vivo while controlling plasma LDL concentration.

Agarose gel electrophoreses of plasma samples from the last a set of rabbits injected with LUVs, SUVs, or saline (these agarose gels separate particles by their charge, which is not the same from one type of particle to another) were performed. Freshly made SUVs migrate very slowly through agarose, which indicates that freshly made liposomes have very little charge. After injection into animals or after co-incubation with plasma or lipoproteins, SUVs pick up proteins from lipoproteins. These proteins give more charge to the SUVs and substantially enhance their migration through agarose gels. SUVs after exposure to plasma migrate faster through these gels than does LDL.

The gels showed a substantial difference between LUVs and SUVs. As expected, the SUVs migrated ahead of LDL in these gels. The LUVs, however, migrated almost exactly where freshly made, protein-free liposomes migrate. This result indicates that LUVs, unlike SUVs, do not readily pick up proteins from circulating lipoproteins.

There is a direct verification of this difference between the liposomes. Human HDL (which has most of the proteins that liposomes pick up) was incubated with either LUVs or SUVs, then the liposomes were reisolated, and assayed their protein-to-phospholipidratios. Per amount of liposomal phospholipid, the SUVs picked up about 40 times as much protein as did the LUVs. This difference appears to arise because of the difference in surface curvature: SUVs are smaller, so their surface is more tightly curved, thus under greater strain, proteins can more easily insert.

There are three most likely metabolic effects of the difference in protein uptake between the two types of liposomes are as follows:

1. VLDL has two metabolic fates: it can be removed from plasma before it is fully converted to LDL by lipolytic enzymes, or it can be fully converted into circulating LDL. SUVs strip apoE off VLDL, thereby slowing its clearance from plasma and favoring its conversion to LDL. In contrast, LUVs leave apoE on VLDL, and so LDL concentrations in plasma would not rise.

2. Absorbed apoproteins might play a role in directing liposomes to different hepatic metabolic pools.

Here are some ways to assay effect on oxidation in vivo: Catella F, Reilly MP, Delanty N, Lawson JA, Moran N, Meagher E, FitzGerald GA. Physiological formation of 8-epi-PGF2 alpha in vivo is not affected by cyclooxygenase inhibition. Adv Prostaglandin Thromboxane Leukot Res. 23:233–236, 1995. These authors describes 8-epi-PGF$_2$alpha, which is an end-product of lipid oxidation. This molecule can be used, they suggest, as a measure of lipid oxidative flux in an animal. It is superior to other commonly used measure of oxidation in vivo, such as anti-oxidant levels (which are affected by diet), thiobarituric acid reactive substances (some sugars interfere with this assay), and short-lived oxidative intermediates (these do not indicate total flux of material being oxidized). Administration of LUVs, by removing oxidized lipids from the periphery, would lower total oxidative flux in vivo, and 8-epi-PGF$_2$alpha would be a suitable way to measure this; Cadet J, Ravanat JL, Buchko GW, Yeo HC, Ames BN. Singlet oxygen DNA damage: chromatographic and mass spectrometric analysis of damage products. Methods Enzymol. 234:79–88, 1994, they describe 8-oxo-2'-deoxyguanosine, which is an end-product of DNA oxidation. As above, this molecule can be used as a measure of DNA oxidative flux in an animal. Administration of LUVs would lower DNA oxidative flux in vivo, and this is a suitable way to measure this; and, Xia E, Rao G, Van Remmen H, Heydari AR, Richardson A. Activities of antioxidant enzymes in various tissues of male Fischer 344 rats are altered by food restriction. J Nutr. 125(2):195–201, 1995. Antioxidant enzymes in tissues were measured, to indicate de-oxidant capacity. LUVs help this. Anti-oxidant levels (vitamin E, ascorbate, urate); oxidized and reduced glutathione; and many other measures can be used to assess peripheral oxidation and oxidative damage. Again, these and other measures would be coupled with LUV administration, to assess efficacy of the therapy.

Other particles that mimic there properties of large liposomes will act similarly, to mobilize peripheral lipids and other exchangeable materials, and deliver exchangeable materials, while avoiding harmful disruptions in hepatic cholesterol homeostasis. For example, these would include emulsion particles that are two large to penetrate hepatic endothelial fenestrae, of a composition and structure that is taken up by the liver slowly, and/or a composition and structure that does not readily acquire specific endogenous proteins. Such emulsions could be made with or without proteins, and could be made from phospholipid and a neutral lipid, such as triglycerides or another neutral lipid.

The invention also provides a pharmaceutical composition comprised or consisting essentially of liposomes dimensioned and of a composition so that the liposomes are taken up slowly by the liver.

The invention also includes a method of forcing the reverse transport of cholesterol from peripheral tissues to the liver in vivo while controlling plasma LDL concentrations comprising the step of parenterally administering a therapeutically effective amount of a multiplicity of large liposomes comprised of phospholipids substantially free of sterol for a treatment period, whereby the liposomes pick-up the cholesterol during the treatment period. A method described above includes the optional step of enhancing tissue penetration of a cholesterol acceptor and increasing extraction of tissue cholesterol and other exchangeable material by co-administration of an effective amount of a compound. The compound is selected from the group consisting of a small acceptor of cholesterol and a drug that increases endogenous small acceptors of cholesterol. In a variant, co-administration of the compound is simultaneous with the parenteral administration of the large liposomes. In another variant, co-administration of the compound is separated in time from the parenteral administration of the therapeutically effective amount of a multiplicity of the large liposomes by an effective time period. The effective time period is in the range of about 1 minute to about two weeks.

In another aspect the invention includes an improved method of reducing the lipid content of arterial lesions comprising the steps of inducing the reverse transport of cholesterol from peripheral tissues to the liver in vivo by administering a therapeutically effective amount of an agent to a subject. The agent is selected from the group consisting of large liposomes comprised of phospholipids substantially free of sterol and small acceptors; periodically monitoring plasma LDL concentrations of the subject to obtain an LDL concentration profile; adjusting the therapeutically effective amount of the agent responsive to the LDL concentration profile; and, administering a pharmaceutical agent to the subject. The agent is selected from the group consisting of compounds to lower LDL concentrations, small acceptors, and compounds to raise HDL concentrations, responsive to the LDL concentration profile, whereby the reduction in lipid content of the arterial lesions is effectively treated and monitored over a treatment period. The arterial lesions comprise lipid rich, rupture prone, type IV and type V arterial lesions. Plaque rupture, thrombosis, and tissue infarction are greatly reduced.

In yet another aspect the invention provides for an improved method of assessing the efficiency of a treatment for reducing the lipid content of arterial lesions. The lesions coming into contact with plasma and a component thereof comprising the steps of inducing the reverse transport of cholesterol from peripheral tissues to the liver in vivo by administering a therapeutically effective amount of an agent to a subject. The agent is selected from the group consisting of large liposomes comprised of phospholipids substantially free of sterol and small acceptors; and, periodically monitoring the plasma component with an assay. The assay is selected from the group consisting of an assay for plasma unesterified cholesterol and phospholipid, an assay of bile acids and cholesterol in stool, an assay of bile acids and cholesterol in bile, an assay of hepatic gene expression in a liver biopsy, an assay of gene expression in peripheral blood leukocytes, the gene comprising a gene involved in cholesterol metabolism, an assay of plasma LDL concentration, and a vascular imaging technique. The vascular imaging technique is selected from the group consisting of cardiac catherization, magnetic resonance imaging, ultrasound, ultrafast CT and a radionuclide assay which optionally includes a stress-thalium scan.

The invention also includes a method of beneficially altering arterial function, blood platelet function, and controlling plasma LDL concentrations and hepatic cholesterol homeostasis in vivo comprising the step of parenterally administering a therapeutically effective amount of a multiplicity of large liposomes comprised of phospholipids substantially free of sterol for a treatment period with or without administration of other agents. The other agents optionally include small acceptors and LDL lowering agents. Optionally a method described above includes the step of taking a measurement of arterial function. The measurement is selected from the group consisting of a measurement of endothelial-derived relaxing factor, a measurement of intracellular calcium concentration in arterial cells, a measurement of arterial cell proliferation, an assay of arterial enzymes, an assay in the presence of calcium channel blockers, an assay of arterial uptake, accumulation and retention of lipoproteins, an assay of arterial accumulation of liposomes, an assay of arterial retention of liposomes, an assay of gene products, and an assay of arterial cell functions. The measurement of endothelial-derived relaxing factor is selected from the group consisting of a functional determination of endothelial-dependent arterial relaxation, chemical determination of production of the endothelial relaxing factor, and an assay of nitric oxide synthase.

A method of beneficially altering blood platelet function while controlling plasma LDL concentrations, arterial function, hepatic cholesterol homeostasis and the platelet function in vivo is also included. A method described above comprises the step of parenterally administering a therapeutically effective amount of a multiplicity of large liposomes comprised of phospholipids substantially free of sterol for a treatment period, the liposomes administered with or without other agents. A method described above optionally includes the step of taking a measurement of arterial function. The measurement selected from the group consisting of a measurement of endothelial-derived relaxing factor, a measurement of intracellular calcium concentration in arterial cells, a measurement of arterial cell proliferation, an assay of arterial enzymes, and an assay of gene products. The measurement of endothelial relaxing factor is selected from the group consisting of a functional determination of endothelial-dependant arterial relaxation and chemical determination of production of the endothelial relaxing factor.

Also included is a method of catabolizing cholesterol with macrophages in vivo and also affecting a plasma component or structural aspects of an artery, comprising the step of administering an effective amount of liposomes to a subject substantially free of cholesterol and being of a size and composition such that the liposomes are capable of being taken up by the macrophages and capable of being catabolized by the macrophages. The cholesterol is mobilized by the liposomes resulting in the liposomes being taken up by the macrophages and catabolized. A method described above also can include the step of periodically monitoring the plasma component with an assay. The assay is selected from the group consisting of an assay for plasma unesterified cholesterol and phospholipid, an assay of plasma cholesterol ester transfer protein activity, an assay of bile acids and cholesterol in stool, an assay of hepatic gene expression in a liver biopsy, an assay of gene expression in a peripheral blood leukocytes, the gene comprising a gene involved in cholesterol metabolism, an assay of plasma LDL concentration, and a vascular imaging technique.

In yet another aspect the invention includes a method of delivering a drug in vivo and avoiding harmful disruptions of hepatic cholesterol homeostasis, comprising the steps of entrapping the drug with an agent. The agent is selected from the group consisting of a cholesterol poor liposome, a cholesterol free liposome, an emulsion, a liposome primarily taken up slowly by hepatic parenchymal cells, an emulsion primarily taken up slowly by hepatic parenchymal cells. The agent is selected from the group consisting of an agent with a protein and an agent without protein to obtain an entrapped drug. A method described above also includes the step of administering a therapeutically effective amount of the entrapped drug for a treatment period. The step of administering comprises the step of slowly infusing the entrapped drug. In variants, the step of administering comprises the step of administering small doses of the agent, appropriately separated in time, to avoid harmful disruptions in hepatic cholesterol homeostasis, and includes using low doses of the agent, whereby disrupting hepatic cholesterol homeostasis is avoided.

A method of controlling plasma LDL levels, hepatic cholesterol homeostasis, arterial enzymes, arterial function, and platelet function, and altering platelet hormone production is also provided. A method described above includes the step of parenterally administering a therapeutically effective amount of a multiplicity of large liposomes comprised of phospholipids substantially free of sterol for a treatment period. The effective amount is administered in a dosage and the dosage is selected from a single dose and repeated doses. A method described above optionally includes the step of diagnosing the efficacy of the administration by taking a measurement of the hormone production and regulating the effective amount in response to the measurement. The measurement of hormone production is an assay selected from the group consisting of an assay for thromboxanes, an assay for prostacyclines, an assay of prostaglandins, an assay for leukotrienes, and an assay for derivatives thereof.

In yet a further aspect the invention provides a method of increasing plasma HDL concentrations, while controlling plasma LDL levels, hepatic cholesterol homeostasis, and hepatic gene expression. A method described above comprises the step of parenterally administering a therapeutically effective amount of a first agent. The first agent comprising a multiplicity of small liposomes to raise HDL concentrations for a treatment period. A method described above then includes the step of co-administering a second agent. The second agent includes large liposomes comprised of phospholipids substantially free of sterol for a treatment period. The effective amount is administered in a dosage selected from a single dose and repeated doses. The co-administration acts to prevent the small liposomes from stimulating harmful changes in hepatic cholesterol homeostasis and an increase in plasma LDL. In a variant, the first agent consists essentially of small liposomes and the second agent consists essentially of large liposomes. A method described above also includes the step of diagnosing the efficacy of the administration by taking a measurement of plasma HDL and LDL levels before, during and after the treatment period.

A method of controlling plasma LDL levels, and hepatic cholesterol homeostasis in vivo while altering cell membrane composition and function is also described herein. A method described above includes the step of parenterally administering a therapeutically effective amount of a multiplicity of large liposomes comprised of phospholipids substantially free of sterol for a treatment period. The effective amount administered in a dosage selected from a single dose and repeated doses. A method described above includes the step of co-administering a small acceptor selected from the group consisting of a small acceptor of cholesterol, an acceptor of sphingomyelin, an acceptor of lysophosphatidylcholine, and an acceptor of a lipid. A method described above can optionally include the step of diagnosing the efficacy of the administration by performing a measurement selected from the group consisting of a measurement of membrane fluidity, a measurement of transmembrane ion flux, the ions selected from the group consisting of calcium ions, sodium ions, and potassium ions, an assay of membrane fragility, and an assay of membrane function.

In a further embodiment, the invention includes a pharmaceutical composition for mobilizing peripheral cholesterol and sphingomyelin that enters the liver of a subject consisting essentially of liposomes selected from the group of uni-lamellar liposomes, multi-lamellar liposomes, combinations thereof, and derivatives thereof, and a pharmaceutical composition for reducing the size of arterial lesions that enters the liver of a subject consisting essentially of a multiplicity of non-liposomal particles for cholesterol depletion of peripheral tissues while avoiding harmful disruptions of hepatic cholesterol homeostasis. The particles are selected from the group of particles substantially free of cholesterol and particles free of cholesterol.

Non-liposomal particles are selected from the group consisting of triglyceride-phospholipid emulsions. The emulsions include emulsions that are not taken up rapidly by hepatic parenchymal cells, emulsions that are not taken up to a large extent by parenchymal cells, and triglyceride-phospholipid-proteinemulsions.

Also included in the invention is a pharmaceutical composition for reducing the size of arterial lesions that enters the liver of a subject consisting essentially of a drug entrapped within an agent. The agent is selected from the group consisting of a cholesterol poor liposome, a cholesterol free liposome, an emulsion, a liposome primarily taken up slowly by hepatic parenchymal cells, and an emulsion primarily taken up slowly by hepatic parenchymal cells. The agent is selected from the group consisting of an agent with a protein and an agent without protein.

The invention also provides for a pharmaceutical composition for increasing plasma HDL concentrations, while controlling plasma LDL levels, hepatic cholesterol homeostasis, and hepatic gene expression, comprising a first agent which comprises a multiplicity of small liposomes to raise HDL concentrations, and a second agent which comprises large liposomes comprised of phospholipids substantially free of sterol.

In yet another aspect a method of controlling cholesterol metabolism in hepatic parenchymal sells in a subject in vivo through cell—cell communication from Kupffer cells to the parenchymal cells is included. A method described above includes the steps of administering a liposome composition to the subject. The liposome composition is selected from the group consisting of large unilamellar liposomes and large multilamellar liposomes. The liposomes have an average diameter of about 50–150 nanometers. The LDL levels in the subject do not increase. A method described above also includes the step of diagnosing the efficacy of the control of cholesterol metabolism by assaying an indicator in the subject. The indicator is selected from the group consisting of plasma LDL concentrations of the subject, hepatic gene expression of the subject, sterol excretion controlling cholesterol metabolism in hepatic parenchymal cells in the subject, and sterol excretion in bile of the subject; and adjusting the administration in response to the assay.

The present invention further provides a mode of operation of artherogenic lipoproteins, cellular structures, and extracellular structures that is altered by the compositions described herein through which beneficial physiological effects are obtained.

Cellular and organism aging and oxidation can be reversed or slowed utilizing a method described aboves and devices described herein.

In another variant, the present invention provides pharmaceutical compositions consisting essentially of unilamellar liposomes having an average diameter of about 100–150 nanometers, which liposomes are not bound to a drug; and a pharmaceutically acceptable carrier. Also provided are methods for treating atherosclerosis using the compositions of the present invention.

As used herein, "drug" is meant to indicate a synthetic compound suitable for therapeutic use without associated bound carriers, adjuvants, activators, or co factors. "Drug" does not include apoproteins, lecithin cholesterol acyltransferase, or albumin. In one variant of the invention, "liposome", "vesicle" and "liposome vesicle" will be understood to indicate structures having lipid-containing membranes enclosing an aqueous interior. The structures may have or one more lipid membranes unless otherwise indicated, although generally the liposomes will have only one membrane. Such single layered liposomes are referred to herein as "unilarnellar". Arterial atherosclerotic lesions have been shown to regress when treated with liposome infusions; In some instances, however, LDL cholesterol has been observed to increase following liposome administration. Prior to the present invention, the cause of this paradox has not been understood.

The present invention is based, in part, on the discovery that liposome size plays a critical role in the metabolism of cholesterol removed from atherosclerotic plagues by the liposomes. Contrary to previous descriptions of liposome therapy, liposomes having a diameter of greater than 100 nanometers are more effective for removing cholesterol from atherosclerotic plaques than smaller liposomes.

The superior action of liposomes greater than 100 nanometers in diameter may be explained by the micro-anatomy of the liver. When circulating in the liver, large liposomes (as used herein, lipoiames greater than 100 nm in diameter) may be cleared by the EMpffer cells that line the sinusoidal openings. The Kupffer cells transfer cholesterol to hepatocytes for excretion in the bile or re-utilization. Small liposomes (as used herein, liposomes smaller than 100 nm may directly access hepatocytes without prior processing by the Kupffer cells. Because these small liposomes are infused in relatively large doses, hepatocytes may be acutely exposed to a relatively high concentration of small liposomes and their accumulated cholesterol. The rapid influx of cholesterol to hepatocytes as delivered by the small liposomes may induce synthesis of apoprotein B. Synthesis of apoprotein B by hepatocytes increases the concentration of plasma LDL that can cause atherosclerotic plaque formation, thus paradoxically worsening vascular disease The pharmaceutical compositions of the present invention generally consist essentially of unilamellar liposomes having an average diameter of about 100–150 nanometers, which liposomes are not bound to a drug; and a pharmaceutically acceptable carrier. In some instances multilamellar liposames may also be employed in the compositions of the present invention, either exclusively or in addition to unilamellar liposomes. The liposomes will have an average diameter of about 100–150 nanometers, typically about 125–140 nanameters. In same embodiments, liposomes having an average diameter larger than 150 nanometers, either uni- or multilamellar, may also be present in the compositions of the present invention.

Persons of skill will appreciate that the liposomes in the compositions of the present invention may be synthesized by a variety of methods, such s described in, e.g., U.S. Pat. No. 4,186,183; U.S. Pat. No. 4,217,344; U.S. Pat. No. 4,261,975; U.S. Pat. No. 4,485,054; U.S. Pat. No. 4,774,085; U.S. Pat.

No. 4,946,787; PCT Publication No. WO 1/17424, Deamer and Bangham, Biochem., Biophys. Acta, 443:629–634 (1976); Fraley et al., Proc. Natl. Aca . Sci. USA, 76:3348–3352 (1979); Hope et al., Biochem. Biophys. Acta, 812:55–65 (1985); Mayer et al., Biochem. Biophys. Acta, 858:161–168 (1986); and Williams et al., Proc. Natl. Acad. Sci., 85:242–246 (1988), each of which is incorporated herein by reference. Suitable methods include, e.g., sonication, extrusion, high pressure/homogenization, microfluidization, detergent dialysis, calcium-induced fusion of small liposome vesicles, and ether-infusion methods, all well known in the art.

Generally, the liposomes are most conveniently generated by sonication and extrusion procedures. Briefly, a chloroform solution of lipid is vortexed and the solvent removed under a steady stream of N2. The sample is dried under a high vacuum. The resulting dry lipid film is rehydrated in 150 mM NaCl and 20 mM (4-(2-hydroxyethyl)] piperazine-ethanesulfonic acid (Hepes, pH 7.4). This generally produces multilamellar liposomal vesicles.

Unilamellar vesicles are prepared by sonication or extrusion. Sonication is generally performed with a tip sonifier, such as a Branson tip sonifier, in an ice bath. Typically, the suspension is subjected to several sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass.

The size of the liposomal vesicles may be determined by quasi-electric light scattering (QELS) as described in Bloomfield, Ann. Rev. Biohyg, Bioeng., 10:421–450 (1981), incorporated herein by reference. Average liposome diameter may be reduced by sonication of formed liposomes. Intermittent sonication cycles may be alternated with QELS assessment to guide efficient liposome synthesis. The liposomes may be composed of a variety of lipids. Generally, the liposomes will be composed of at least one phospholipid, typically egg phosphatidylcholine, egg phosphatidylglycerol, distearoylphosphatidylcholine, or distearoylphosphatidylglycerol. However, synthetic, non-allergenic, phospholipids are perferable to naturally occuring phospholipids.

Many embodiments of the present invention will include more than one phospholipid. Other phospholipids suitable for formation of liposomes comprising the compositions of the present invention include, e.g., soybean phosphatidylcholine, soyybean phosphatidylglycerol, lecithin, P,y-dipalmitoyl-a-lecithin, sphingomyelin, phosphatidylserine, phosphatidic acid, N(2,3di(9-(Z)-octadecenyloxy))-prop-1-yl-N,N,N-trimethylammonium chloride, phosphatidylethanolarnine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl phosphatidylcholine, stearoyl-palmitoyl-phosphatidylcholine, di-palmitoyl-phosphatidylethanolamine, di-stearoyl phosphatidyl-ethanolamine, di-myrstoyl-phosphatidylserine, di-oleyl-phosphatidylcholine, and the like. Non-phosphorus containing lipids may also be used in the liposomes of the compositions of the present invention. These include, e.g., stearylamine, docecylamine, acetyl palmitate, fatty acid amides, and the like. Additional lipids suitable for use in the liposomes of the present invention are well known to persons of skill in the art and are cited in a variety of well known sources, e.g., McCutcheon's Detergents and Emulsifiers and McCutcheon's Functional Materialg, Allured Publishing Co., Ridgewood, N.J., both of which are incorporated herein by reference.

Generally, it is desirable that the liposomes be composed of lipids that are liquid-crystalline at 37 degrees C., often at 35 degrees C., and even 32 degrees C. Liposomes in the liquid-crystalline state typically accept cholesterol more efficiently than liposomes in the gel state. As patients typically have a core temperature of about 370 C., liposomes composed of lipids that are liquid-crystalline at 370 C. are generally in a liquid crystalline state during treatment and, therefore, optimize removal of cholesterol from plaques.

The pharmaceutical compositions of the present invention also comprise a pharmaceutically acceptable carrier. Many pharmaceutically acceptable carriers may be employed in the compositions of the present invention. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of liposomes in the carrier may vary. Generally, the concentration will be about 20–200 mg/ml, usually about 50–150 mg/ml, and most usually about 100 mg/ml. Persons of skill may vary these concentrations to optimize treatment with different liposomal components or of particular patients. For example, the concentration may be increased to lower the fluid load associated with treatment.

This may be particularly desirable in patients having atherosclerosis-associated congestive heart failure or severe hypertension. Alternatively, liposomes composed of irritating lipids may be diluted to low concentrations to lessen inflammation at the site of administration.

The liposomes may also be bound to a variety of proteins and polypeptides to increase the rate of cholesterol transfer or the cholesterol-carrying capacity of the liposomes. Binding of apoproteins to the liposomes is particularly useful. As used herein, "bound to liposomes" or "binding to liposomes" indicates that the subject compound is covalently or non-covalently bound to the surface of the liposome or contained, wholly or partially, in the interior of the liposome. Apoprotein A., apoprotein A2, and apoprotein E will generally be the most useful apoproteins to bind to the liposomes. These apoproteins promote transfer of cholesterol and cholesteryl esters to the liver for metabolism. Lecithin cholesterol acyltransferase is also useful for metabolizing free cholesterol to cholesteryl esters. Liposomes in the pharmaceutical compositions of the present invention may be bound to molecules of apoprotein A, apoprotein A and lecithin-cholesterol acyltransferase, singly or in any combination and molar ratio. Additional proteins or other nonprotein molecules may also be useful to bind to the liposomes to enhance liposome stability or half-life and the like. These include, e.g., cholesterol, polyethyleneglycol, alkylsulfates, ammonium bromide, albumin, and the like.

Also provided are methods for treating atherosclerosis in an animal. The methods generally comprise administering a liposome composition to the animal, which liposome composition consists essentially of unilamellar liposomes having an average diameter of about 100–150 nanometers. By treating "atherosclerosis", it is meant performing a therapeutic intervention that results in reducing the cholesterol content of at least one atherosclerotic plaque or prophylactically inhibiting or preventing the formation or expansion of an atherosclerotic plaque. Generally, the volume of the atherosclerotic plaque, and hence the degree of obstruction of the vascular lumen, will also be reduced. The present methods are particularly useful for treating atherosclerotic lesions associated with familial hyperlipidemias.

The methods of the present invention may reduce the cholesterol content of atherosclerotic plaques and/or the volume of atherosclerotic plaques. The cholesterol content will generally be reduced by at least 10%–30%, often by 300 50%, and in some instances as much as 75%–85% or more. The volume of the atherosclerotic plaques will also generally be reduced. The reduction in plaque volume will generally be at least 5%–30%, often as much as 50%, and in some instances 75% or more.

Cholesterol may be mobilized from the plaques by either direct efflux into the liposomes or into lipoproteins that subsequently transfer the cholesterol to the liposomes. As cholesterol is transferred to the liposomes from the lipoproteins, the lipoproteins may receive more cholesterol from plaques. Generally, when cholesterol is received from lipoproteins, the cholesterol is transferred from HDL.

The methods may be useful to treat atherosclerosis in a variety of animals and in a variety of blood vessels. Typically, the animal will be human, although non-human primates, dogs, cats, rodents, horses, cows, and the like may be treated by the methods of the present invention. Atherosclerosis of Any blood vessel, such as the aorta, carotid arteries (common, internal, and external), coronary arteries, mesenteric arteries, renal arteries, iliac arteries, popliteal arteries, and the like, may also be treated by the methods of the present invention.

The methods may also be useful for prophylactic treatments. Such prophylactic treatments are particularly useful following invasive vascular procedures. Vascular regions having injured endothelium are at increased risk for developing atherosclerotic plaques. Therefore, invasive vascular procedures, such as coronary angioplasty, vascular bypass grafting, and other procedures that injure the vascular endothelial layer, may be practiced in conjunction with the methods of the present invention. As the invasive procedure injures the endothelium, the liposomes act to remove cholesterol from the injured region and inhibit or prevent plaque formation of expansion during endothelial healing.

Hyperlipidemias may also be treated by the methods of the present invention. Administration of liposomes, alone or bound to apoprotein A1 and apoprotein A2, to individuals having hypoalphalipoproteinemia from genetic or secondary causes, familial combined hyperlipidemia, and familial hypercholesterolemia is a useful treatment.

The liposomes administered in the methods of the present invention will be composed of lipids as described above. The lipids will generally be in the liquid-crystalline state at 370 C. The lipids will also generally include one or more phospholipids, often egg phosphatidylcholine or egg phosphatidylglycerol, although liposomes may be composed of many other lipids, examples of which are described above.

The liposomes may be administered in many ways. These include parenteral routes of administration, such as intravenous, intramuscular, subcutaneous, and intraarterial. Generally, the liposomes will be administered intravenously. Often, the liposomes will be administered into a large central vein, such as the superior vena cava or inferior vena cava, to allow highly concentrated solutions to be administered into large volume and flow vessels. The liposomes may be administered intraarterially following vascular procedures to deliver a high concentration directly to an affected vessel.

The liposomes may also be administered directly to vessels in a topical manner by surgeons during open procedures. In some instances, the liposomes may be administered orally or transdermally. The liposomes may also be incorporated in vascular stents for long duration release following placement.

This is particularly effective for angioplasty treatment of restenosis of lesions in the coronary arteries. As described above, the liposomes will generally be administered intravenously in the methods of the present invention. Often multiple treatments will be given to the patient, generally weekly. Typically, the therapy will continue for about 4–16 weeks (4–16 treatments), usually about weeks (10 treatments). The duration and schedule of treatments may be varied by methods well known to those of skill.

The dose of liposomes may vary depending on the clinical condition and size of the animal or patient receiving treatment. Humans will generally be treated with about 0.1–1.5 gm of liposomes/kg body weight, usually about 0.2–0.75 gm gm/kg, and most usually about 0.28–0.42 gm/kg.

Serum measurements of total free cholesterol, total esterified cholesterol, HDL cholesterol, LDL cholesterol, and VLDL cholesterol may be used to assess and modify dosage amounts and schedules during the treatment regimen. As cholesterol is mobilized from plaqpes, total serum cholesterol rises. It is desirable that total serum cholesterol and HDL cholesterol , rise during therapy, and esterified cholesterol drop during therapy. The liposome dose for different animals will generally approximate the human weight-determined dosage.

The following examples are offered by way of illustration and not limitation.

EXAMPLES

Example 1

Influence of Liposome Size and Composition on In Vivo Cholesterol Mobilization

This example demonstrates the relative cholesterol mobilizing efficacy of liposomes of different sizes and compositions in mice. Liposomes having a mean diameter of about 125 nm were found to be the most effective in mobilizing cholesterol in vivo.

Liquid-crystalline liposomes were more effective in mobilizing cholesterol than gel-state liposomes. Cholesterol and [4-(2-hydroxyethyl)] piperazineethanesulfonic acid (Hepes) were obtained from Sigma. [$^{14}$C]cholesterol hexadecyl ether and [3H]cholesterol were purchased from New England Nuclear. Egg phosphatidylcholine (EPC), distearoylphosphatidylcholine (DSPC), distearoylphosphatidylglycerol (DSPG) and egg phosphatidylglycerol (EPG)

were supplied by Avanti Polar Lipids. Bio-Gel A-15 m medium was purchased from Bio-Rad. All chemicals, thin layer chromatography plates and solvents were of analytical grade and purchased from BDH Chemicals.

All liposome preparations were labelled using trace amounts of ($^{14}$C)cholesterol hexadecyl ether (CHE). This labelling is useful as (1) it does not undergo passive exchange between membranes; (2) mice do not exhibit cholesterol-ester exchange protein activity; and (3) the ether-linked fatty acid is not cleaved in the plasma.

Consequently, in this model system CHE is an excellent liposome marker and vesicle concentrations in the plasma were estimated from the specific activity of this label. A chloroform solution of EPC and CHE was vortexed and solvent was removed under a stream of N2. The sample was dried under high vacuum for 2 h. The dry lipid film was hydrated in 150 mM NaCl, 20 mM Hepes (pH 7.4) to generate multilamellar vesicles (MLV). Vesicles were prepared from MLV either by sonication, to generate small unilamellar vesicles (SUV) or extrusion to produce large unilamellar vesicles (LUV). Sonication was performed using a Branson tip sonifier, following standard protocols. The MLV suspension was diluted to 30 mg/ml, immersed in an ice bath and subject to 3 cycles of sonication, each of 10-min duration. The initial milky suspension became clear and the vesicle size was effective, as determined by quasi-elastic light scattering (QELS).

The SUV were centrifuged at 10000Xg for 30 min to remove titanium fragments originating from the sonicator tip. Extrusion was carried out using a 10 ml Lipex Biomembranes Extruder equipped with a water jacketed thermobarrel as described by Hope et al., Biochim. Biophys. Acta, 812:55–65 (1985), incorporated herein by reference. MLV were sized through two stacked polycarbonate filters of defined pore size to generate a variety of LUV and homogeneous MLV as described in Hope et al., supra, and Mayer et al., Biochim. Biophys. Acta, 858:161–168 (1986), incorporated herein by reference.

The size of vesicles generated by sonication and extrusion procedures was determined by QELS analysis utilizing a Nicomp Model 370 submicron laser particle sizer equipped with a 5-mW He-Ne Laser. The Nicomp QELS analyzes fluctuations in light-scattering intensities due to vesicle diffusion in solution. The measured diffusion coefficient is used to obtain the average hydrodynamic radius and thus, the mean_ diameter of vesicles. The following diameters are expressed as the mean plus or minus;S.D. of vesicle preparations prior to injection. Vesicles prepared by sonication were 30 plus or minus 7 nm in diameter (SUV30)-Vesicles prepared by extrusion through filters with a pore size of 0.05 $\mu$m were 70 nm plus or minus 19 nm, 0.1 $\mu$m pore size were 125 nm plus or minus 30 nm, and 0.4 $\mu$m pore size were 237 nm plus or minus 90 nm. Generally, the vesicles prepared by extrusion are referred to herein by the filter pore size used in their preparation, i.e., LUV50, LUV100 and MLV400 Female BDF-1 or CD-1 mice, weighing 20–22 g (Sprague-Dawley), were used throughout this study. Liposomes were injected via the tail vein at a dose of 300 mg/kg, which was typically 6 mg of liposomes in 200 ml of buffer injected for each animal. Control mice were injected with an equal volume of buffer and both groups were sacrificed at specified times with blood collection in EDTA microtainer tubes by heart—puncture. Plasma was obtained following centrifugation at 2000×g for 10 min, and an aliquot removed for scintillation analysis using a Beckman LS 3801 liquid scintillation counter.

The average of data from 16 mice (from four separate experiments) is indicated at each time point, unless indicated otherwise. A 27×1.5 cm Bio-Gel A-15 m gel filtration column, equilibrated with 150 mM NaCl, 10 mM Tris, 0.1% EDTA, 0.3% NaN3 QH 7.4) was used to fractionate plasma samples. Columns were eluted at a flow rate of 1 ml/min and 1-ml fractions were collected for radioactivity and lipid analyses. Data on the cholesterol:phospholipid (C/P) ratio of vesicles and lipoproteins after infusion was obtained from pooled fractions corresponding to the liposomal and lipoprotein peaks. The Bio-Gel columns were calibrated with respect to lipoprotein elution by preparing purified human lipoprotein fractions using standard ultracentrifugation procedures as described in Schumaker et al., Methods Enzymol., 128:155–181 (1986), incorporated herein by reference. The lipoprotein fractions were each labelled with [$^3$H]cholesterol. The elution profiles of the columns were monitored for radioactivity.

Pooled column fractions and plasma samples were extracted employing the Bligh and Dyer procedure. Bligh and Dyer, Can. J. Biochem. Physiol., 37:911–917 (1959), incorporated herein by reference. The lipid extracts were analyzed for total cholesterol using the assay method of Rudell and Morris, J. Livid Res., 14:364–366 (1973). Free and esterified cholesterol concentrations were determined following separation by TLC using hexane/ethe,/acetic acid (70:30:1 (v/v)). Standards were used to identify the area of the plate corresponding to these two lipids, the silica was aspirated and the lipid eluted for assay using chloroform/methanol (2:1 (v/v)). Plasma vesicle phospholipid content was determined by dividing [$^{14}$C]CHE radioactivity by liposome-specific activity and phospholipid concentrations were determined by the method of Fiske and SubbaRow, J.Biol Chem., 66:375–400 (1925). Erythrocytes were extracted using the method of Rose and Oklander (J. Lipid Res., 6:428–431 (1965)), followed by a Bligh and Dyer wash to remove residual salts. An aliquot of red blood cells was retained for cell number determination using a Coulter cell counter in order to express cholesterol and phospholipid concentrations as mmol/$10^9$ cells.

Blood was pooled from a group of mice and red cells packed by low-speed centrifugation. The serum was labelled with [$^3$H]cholesterol by incubation for 10 min at 37 degrees C. with 100 $\mu$Ci of radioisotope dried from ethanol. The labelled serum was added to the packed cells and the mixture incubated at room temperature for 30 min. The cells were washed and approximately $10^6$ dpm of [3H]cholesterol-labelled cells injected into the experimental groups via the tail vein. Approximately 1 min after the injection of cells, saline or liposomes were administered.

Donor and acceptor liposomes were separated employing ion exchange chromatography. A 10-fold excess of donor vesicles (100 nm diameter) composed of EPC/EPG/Chol (40:15:45 molar ratio) were incubated with 100-nm or 400-mm EPC acceptors. Donor liposomes were labelled with [3H]cholesterol at 5 $\mu$Ci/100 mg total lipid and acceptors were labelled with [14C] CHE at 0.5 gCi/100 mg lipid. At specified time intervals, 50 $\mu$l aliquots of the incubation mixture Q mg acceptor+10 mg donor/ml) were removed and passed down a DEAE-Sepharose 6B-CL column prepared in a 1-ml tuberculin syringe equilibrated with 30 XM NaCl, 20 mM Hepes QH 8.0). Columns were spun at 1000×g for 1 min prior to applying aliquots of the incubation mixture. The liposome mixture was spun through the column and the eluant (acceptors) obtained with two subsequent wash/spin cycles with 500-ml aliquots of buffer. Recovery of 14C-labelled vesicles (acceptors) was typically >90%. Control experiments in which donors were labelled with a non-exchangeable marker indicated that all of the donor vesicles bound to the ion exchange column under the conditions of the experiment.

Cholesterol accumulation by acceptors was determined using an LS 3801 Beckman scintillation counter equipped with a 14C/3H dual-label program. Two groups of mice (n=4) were maintained in metabolic cages and feces collected daily. After 3 days one group was injected with 200 $\mu$l of saline and the second group with approx. 6 mg of EPC IUV100 (dose 300 mg/kg). Fecal material was collected for a further 7 days. Samples were extracted using an isopropanol/chloroform extraction procedure and subsequently assayed for total cholesterol, free cholesterol and cholesteryl esters, as described above.

Experiments were carried out on mice maintained on regular, laboratory food for rodents (cholesterol excretion rate 10–12 Amol/g faeces) and on Teklad low cholesterol (casein-based diet which resulted in an excretion rate of approx. 0.8 $\mu$mol cholesterol/g feces).

Figure 29:
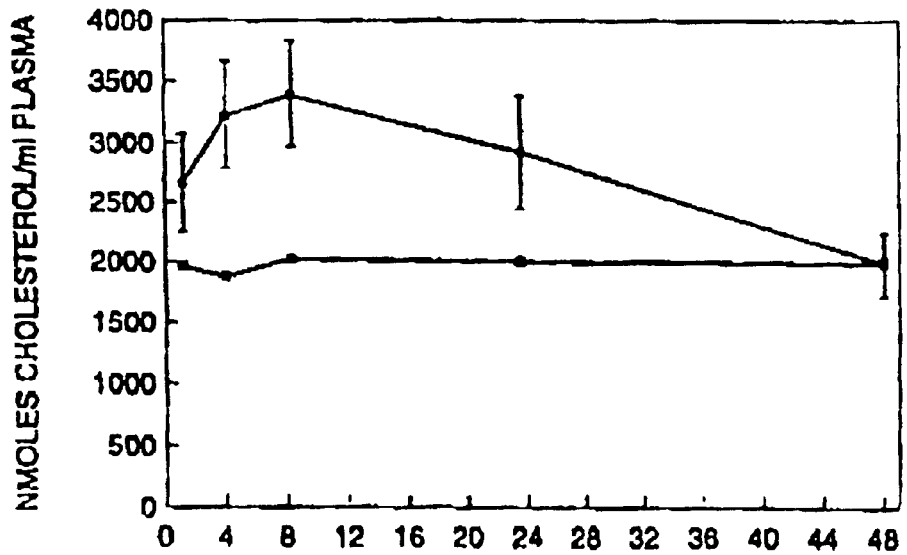
FIGS. 29–30 demonstrates cholesterol mobilization by a homogeneous population of large unilamellar vesicles with a mean diameter of 125 nm.
Figure 30:
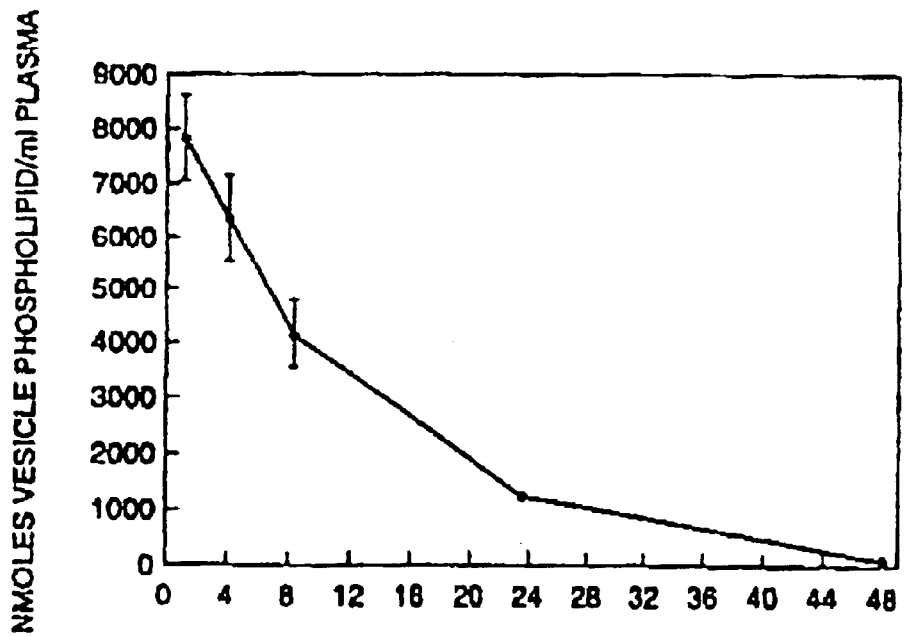

FIGS. 29 and 30 demonstrate cholesterol mobilization by a homogeneous population of LUV with a mean diameter of 125 nm as determined by QELS (referred to as $LUV_{100}$ prepared by extrusion as described above). A dramatic increase in plasma cholesterol was observed for animals receiving liposomes (FIG. 29). Sterol levels peaked 4–8 h after injection at a concentration nearly double that measured in the control mice injected with an equivalent volume of saline. Plasma cholesterol concentrations gradually returned to normal levels after 48 h correlating well with the liposome clearance profile shown in FIG. 30. Liposomes were labelled with trace amounts of [$^{14}C$]CHE, a non-exchangeable, non-metabolizable marker frequently used to monitor liposome clearance and distribution in vivo.

Figure 31:
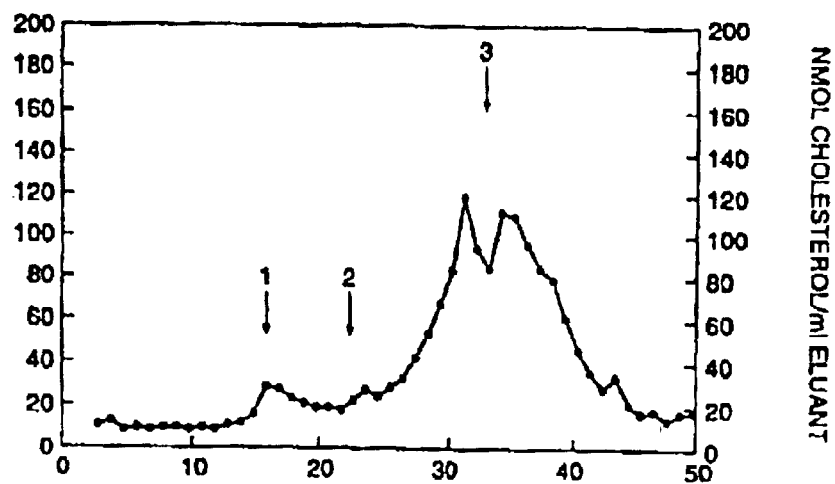
FIGS. 31–32 illustrates plasma cholesterol distribution in normal and liposome animals.
Figure 32:
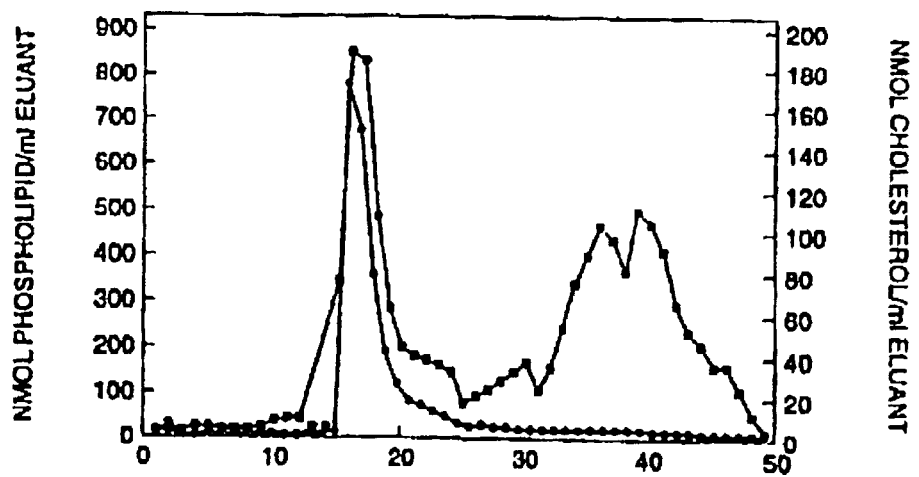

Using gel filtration as described above, mouse plasma was fractionated and the cholesterol profile determined using the chemical assay procedure of Rudel and Morris. Plasma from control and liposome-treated animals were compared and the results are shown in FIGS. 31 and 32. FIG. 31 shows a normal cholesterol distribution with the majority of cholesterol associated with combined LDL and HDL peaks (fractions 22–50). The elution volumes of VLDL, LDL and HDL were determined as described above. A minor quantity of sterol was detected in the void volume, corresponding to the larger chylomicron and VLDL lipoprotein particles, but quantitatively these fractions represent <5% of the total cholesterol content of the plasma. The elution profile of plasma from liposome-treated animals (4 h time point) is shown in FIG. 32. The [14C]CHE liposome marker was almost exclusively detected in the void volume, indicating that the LUV100 were well separated from the fractions containing LDL and HDL (liposomes smaller than 100-nm diameter are included in the gel and cannot be separated from LDL). The absence of radioactivity in the remaining fractions indicated that little, if any, assimilation of vesicles into the lipoprotein pool occurred. However, it is possible that small quantities of vesicles had undergone structural transitions to lipoprotein-like particles, but were removed rapidly from the circulation and therefore, not detected.

The cholesterol content of column fractions shown in FIG. 32 clearly shows that the excess sterol in the plasma of treated mice is associated with LUV. The slight frame shift of peaks between FIG. 31 and FIG. 32 is the result of differences in elution rate and not due to changes in lipoprotein size. Using TLC analysis it was determined that >90% of the liposomal cholesterol was free cholesterol, the remainder being cholesterol ester.

Figure 33:
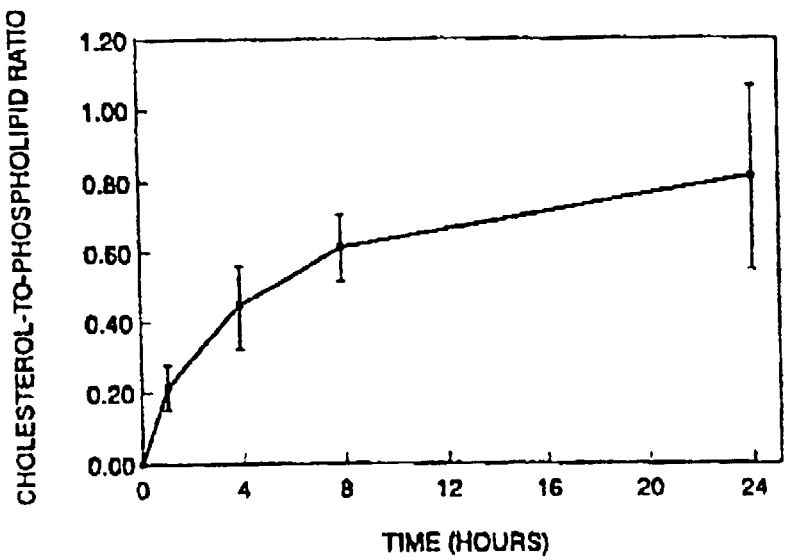
FIG. 33 illustrates liposome cholesterol accumulation over a 24-h time-course in vivo.

The excellent separation of LUV100s from the quantitatively most abundant lipoproteins enabled straight forward isolation and subsequent analysis of the vesicle lipids. Liposome cholesterol accumulation was shown by the increasing C/P ratio of vesicles over a 24-h time-course in vivo, as shown in FIG. 33. Consequently, after 24 h the liposomes remaining in the circulation (approx. 10–15% of the initial dose) were in equilibrium with respect to cholesterol and net sterol movement was negligible.

Plasma cholesterol concentrations were measured over a 48-h period in animals treated with a variety of liposomal preparations varying in diameter from 30–250 nm. Sonicated vesicles were prepared as described above. The remaining vesicles were produced by extrusion of MLV through filters with defined pore-sizes to give vesicle populations with the mean diameters described above. Vesicles are referred to-by the filter pore size used for their synthesis.

Figure 34:
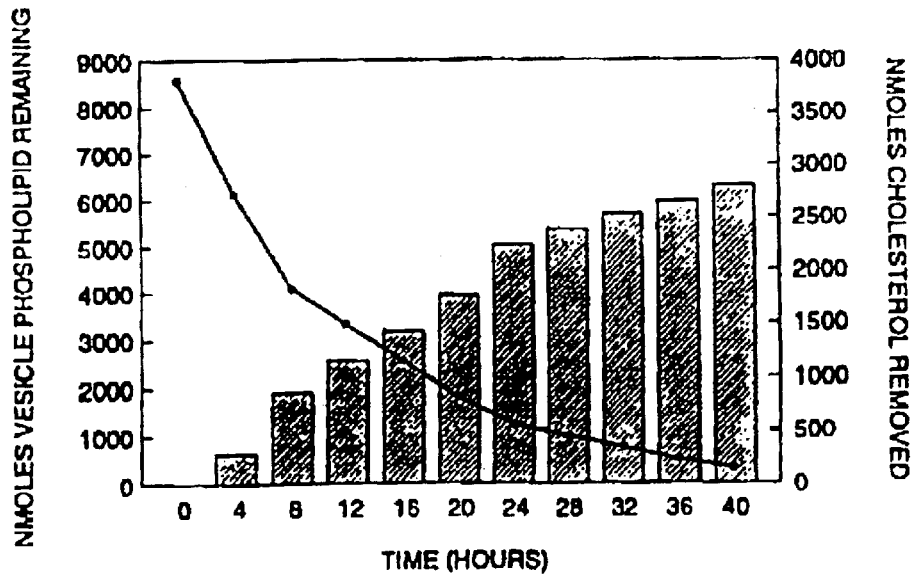
FIGS. 34–35 illustrates cholesterol mobilization by liposomes.

The amount of cholesterol accumulated and removed by liposomes in vivo is a function of both the rate of cholesterol uptake and the rate of liposome clearance. An estimate of the mass of cholesterol removed from the circulation (mostly by the RES) can be made by calculating the C/P ratio of vesicles in yivo from plasma concentration of vesicle phospholipid and cholesterol as the excess plasma concentration above the control at the various experimental time points. All cholesterol above control levels is associated with circulating liposomes. The plasma volume of mice used in these studies was approx. 1 ml, consequently the total amount of phospholipid cleared from the circulation between time points was known. Using the average C/P ratio measured for vesicles between each assay interval an estimate of the amount of cholesterol removed was obtained. The analysis was not continued beyond the point where less than 5% of the initial phospholipid dose remained in the circulation as below this level the measurement error was too large to determine accurate C/P ratios. FIG. 34 shows the cumulative level of cholesterol removed by IDV 100 up to the time when approx. 5% of the dose remains. After 40 h 2800 nmol of cholesterol were removed from the circulation by the RES, which represents 33 mol % of the injected phospholipid dose.

Figure 35:
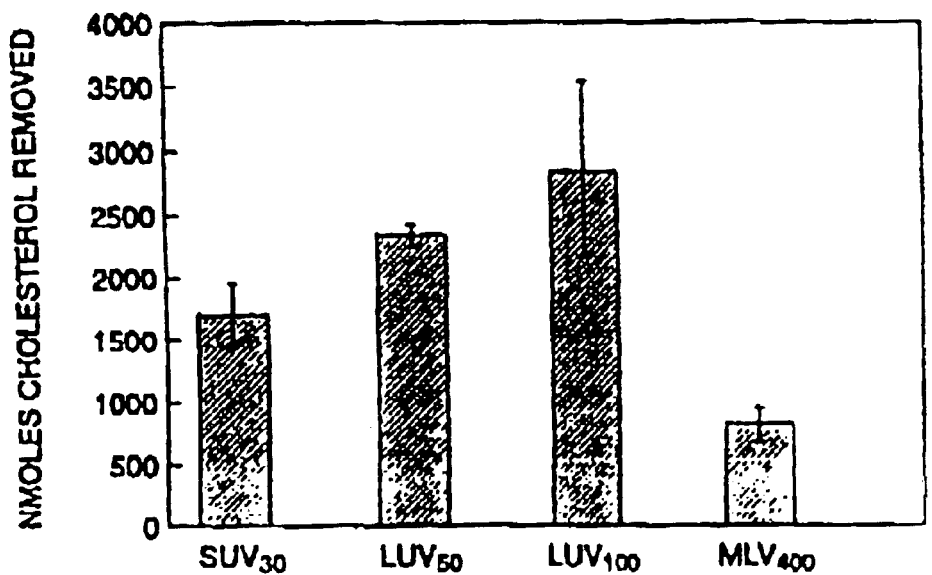

This analysis was used to compare the various liposomal preparations tested. For each preparation the plasma cholesterol and phospholipid clearance profiles were determined and analyzed as described above. The results in FIG. 35 show that LUV mobilize cholesterol most efficiently.

The transfer of sterol from donor vesicles to unilamellar and multilamellar vesicles was studied. Using freeze-fracture electron microscopy and NMR analysis, it has been shown that MLV sized through 400-nm pores retain a number of internal lamellae and therefore cannot be classified as LUV. The transbilayer movement (flip-flop) of cholesterol is rapid, on the order of seconds to minutes in a liquid crystalline bilayer under conditions that promote net sterol flux. Consequently, it was expected that multilamellar systems would act as a good sink for cholesterol as sterol should rapidly disperse through the internal lamellae.

Figure 36:
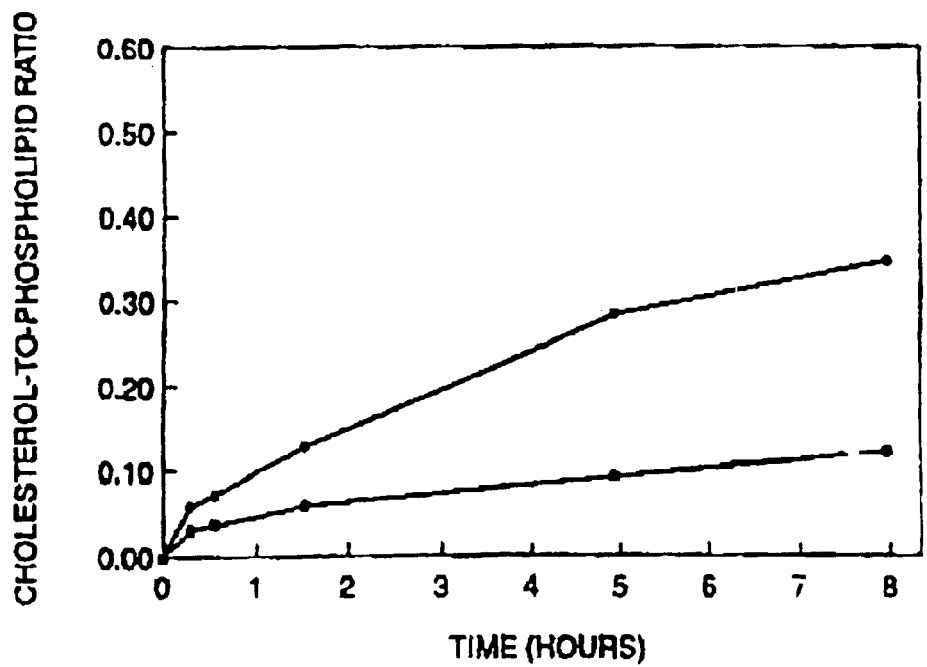
FIG. 36 illustrates a comparison of the rate of cholesterol accumulation by unilamellar and oligolamellar liposomes.

Using an in vitro model in which LUV100 or ML V400 were incubated with a 10-fold excess of donor liposomes containing tritiated cholesterol as described above, the net transfer of sterol from donor to acceptor was monitored. The rate of cholesterol accumulation in the unilamellar preparation was greater than that observed for the oligolamellar vesicles. It is interesting to note that in the presence of a 10-fold excess of donor vesicles the equilibrium C/P ratio of the acceptor should be approx. 0.9:1. The data in FIG. 36 show that the 100-nm acceptors only achieve a ratio of 0.35:1 after 8 h at 37 degrees C. This is approximately half the rate of accumulation observed for the same vesicles in vivo (FIG. 33).

The cholesterol mobilizing properties of two types of LU100 were compared. The two types of LUV100 were composed of EPC/EPG (95:5 mol ratio) which is liquid-crystalline at 37 degrees C. and DSPC/DSPG (95:5) a gel-state lipid matrix at the body temperature of the mouse. Phosphatidylglycerol (PG) was incorporated to impart a surface negative charge, necessary to prevent the gel-state vesicles from aggregating in the absence of cholesterol as described in Nayer et al., Biochem. Biophys. Acta, 986:200–206 (1989), incorporated herein by reference.

Reliable comparison of the two systems was facilitated by adding a negative charge to the EPC vesicles. The results, presented in FIG. 37, reveal that the gel-state vesicles produced a delayed increase in plasma cholesterol which did not peak until after 24 h, whereas EPC/EPG vesicles gave rise to a cholesterol profile similar to that observed for EPC alone.

Figure 37:
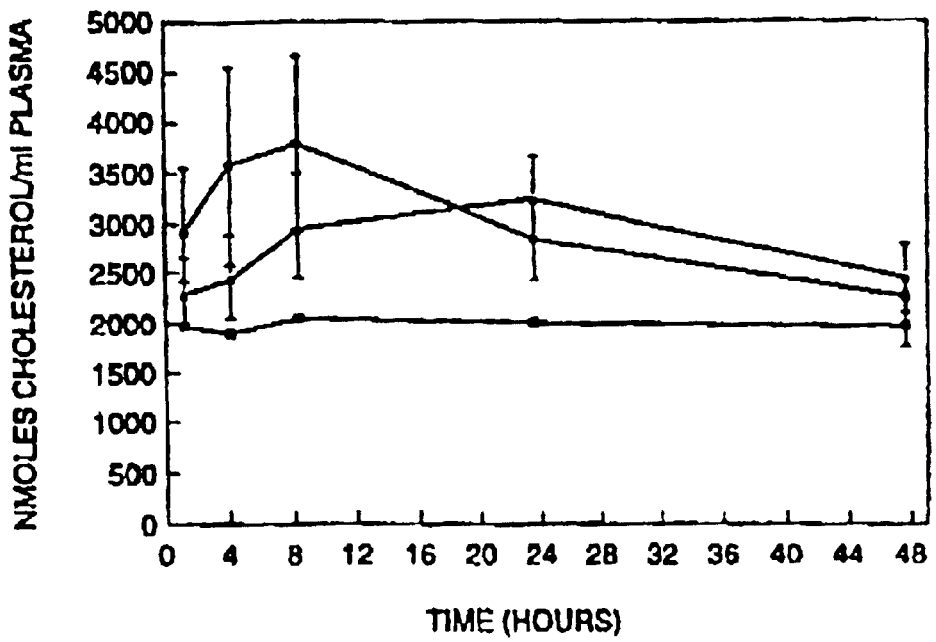
FIGS. 37–38 demonstrates the cholesterol mobilizing ability of liposomes having different compositions.
Figure 38:
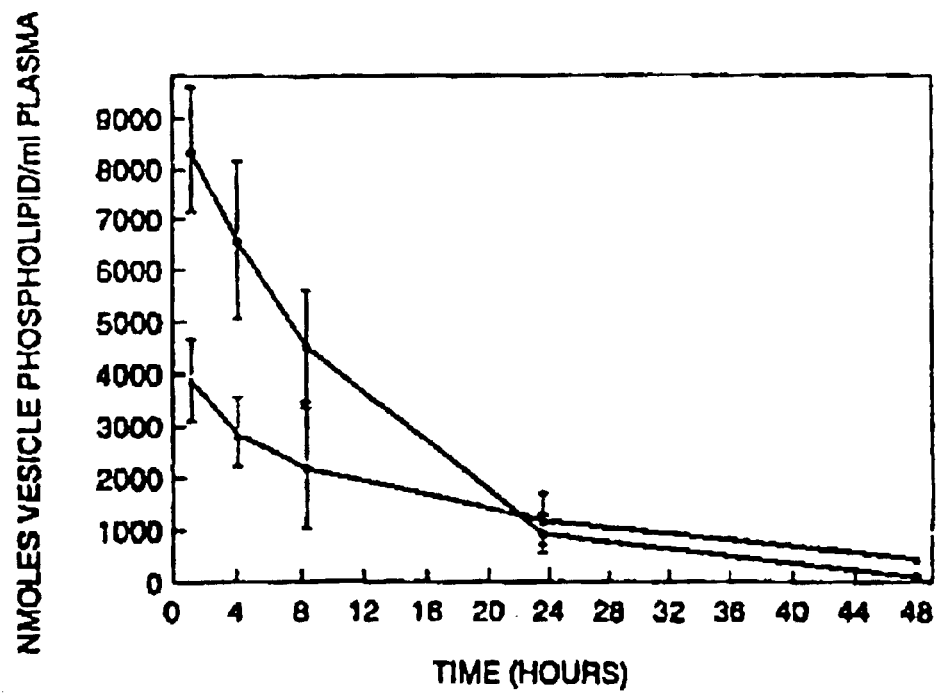

The data in FIG. 37 demonstrate that the rate of cholesterol accumulation for these two types of vesicle was the same. The different plasma cholesterol profiles occurred because approximately 70% of the DSPC/DSPG vesicles were cleared within 4 h compared to less than 30% of the EPC/EPG LUV100 (FIG. 38). The bulk of cholesterol mobilization occurred in the first 24 h, consequently liquid crystalline EPC/EPG removed more than 3000 nmol to the RES, whereas DSPC/DSPG vesicles removed 1700 nmol. The source of the accumulated liposomal cholesterol and its fate was determined.

Ultimately, cholesterol efflux must occur from atherosclerotic plaque to achieve regression. However, it is known that the cholesterol within cells and atherosclerotic lesions equilibrates more slowly than sterol present in plasma membranes directly exposed to acceptor particles.

Movement of this cholesterol will be a secondary event initiated by the primary efflux of outer membrane cholesterol. In a 20-g mouse approximately 35% of the circulating sterol is associated with lipoproteins and about 65% with the plasma membranes of erythrocytes. However, all of the sterol associated with erythrocytes is free cholesterol, whereas a large proportion of lipoprotein sterol is esterified.

Figure 39:
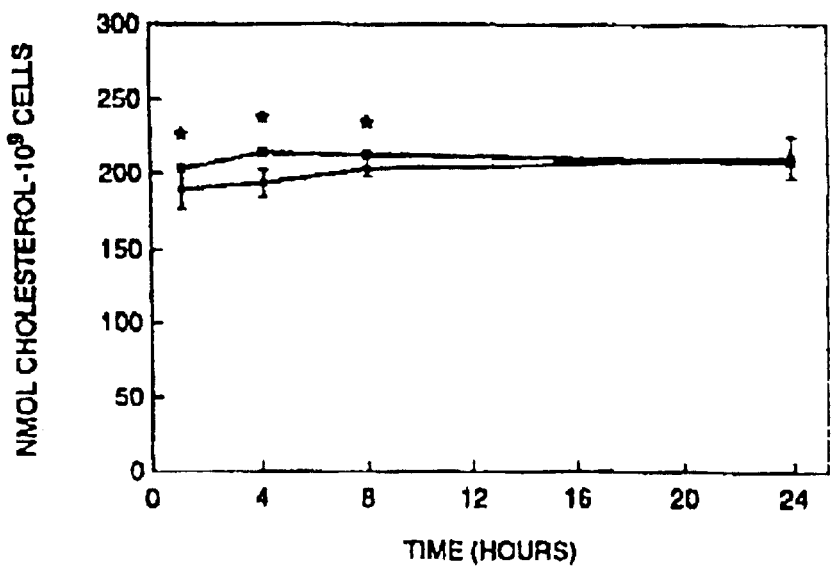
FIGS. 39–41 illustrates the cholesterol content of erythrocytes in mice treated with liposomes and untreated mice.

Consequently, the largest pool of free cholesterol in the circulation is in the red blood cell plasma membrane. It was found that this source of cholesterol does not change significantly in the presence of liposomes, despite a two fold increase in plasma sterol concentration. This result is shown in FIG. 39. Erythrocyte membrane cholesterol can be depleted by liposomes in vitro. Consequently it was determined whether erythrocytes act as the primary sterol donor and then rapidly replenished by lipoproteins which are in turn able to extracate and scavenge more sterol from peripheral tissues.

Figure 40:
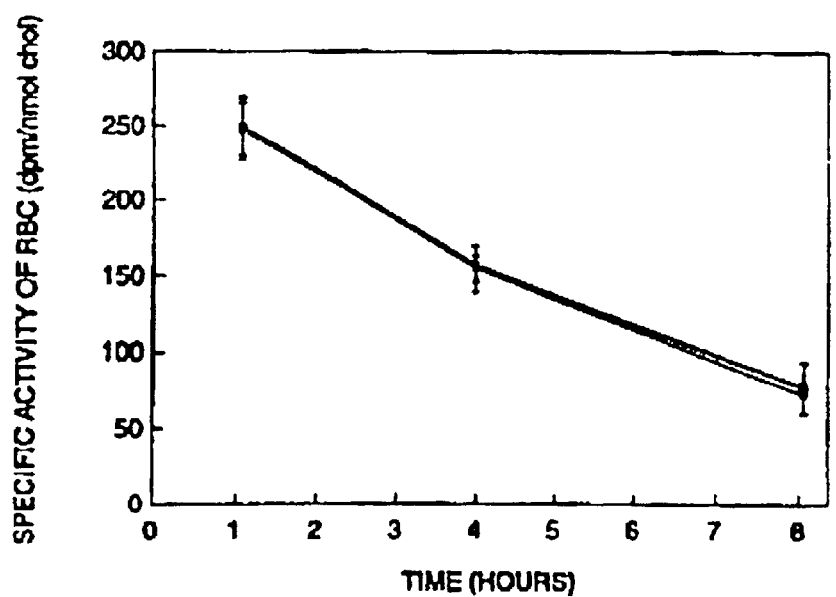
Figure 41:
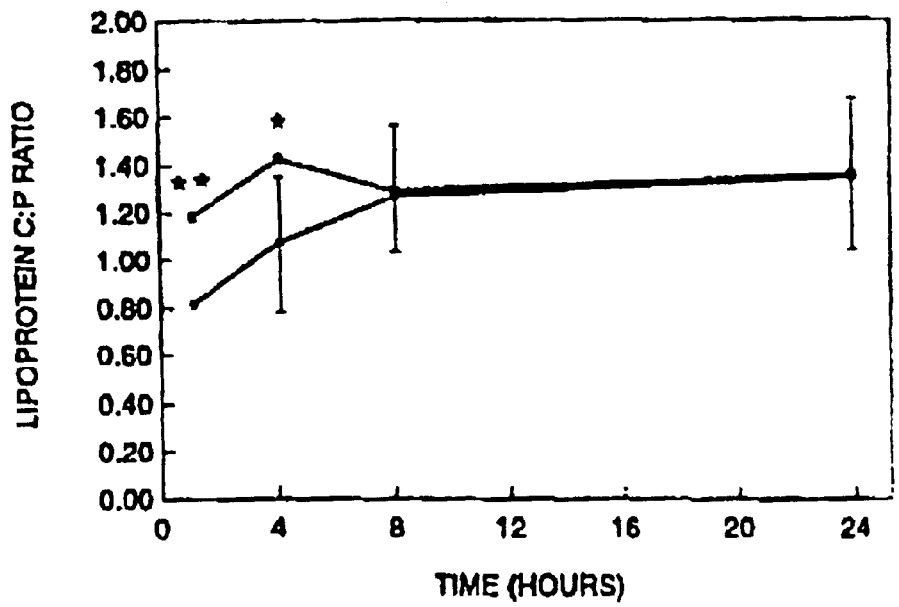

Erythrocytes were isolated from mice and labelled with [$^3$H]cholesterol in vitro. The labelled cells were injected into a group of mice, half of which were subsequently treated with saline and half with 300 mg/kg of EPC LUV100. The specific activity of red blood cell cholesterol was determined over an 8-h time-course and the two groups compared. As demonstrated in FIG. 40, the decrease in cholesterol specific activity is the same for both the control and experimental group. Interpretation of these data is limited by the fact that cells labelled in vitro are also removed from the circulation over a similar time-course (determined by chromium labelling). However, it can be estimated that at least 50% efflux of cell sterol would be necessary to account for the rise in plasma cholesterol observed after 8 h. This would result in a considerable dilution of erythrocyte cholesterol if this sterol pool were continuously replenished. As this has not been observed, the data suggest that red blood cell cholesterol is not the primary source of the liposomal sterol accumulated in vivo. C/P ratios of lipoproteins showed a significant decrease over control values in the first 8 h (FIG. 7C). The ratio returned to normal values after 8 h mirroring the time course of cholesterol accumulation by vesicles. This suggests that it is primarily lipoprotein cholesterol in equilibrium with circulating liposomes, and that lipoproteins mediate the transfer of cholesterol from peripheral tissues to liposomes.

The results are also consistent with observations in vitro that indicate cholesterol can undergo desorption from lipoproteins more readily than from erythrocytes. Finally, the rate of cholesterol accumulation by LUV100 in vivo (FIG. 33) is considerably faster than that observed in vitro (FIG. 36), indicating that the rate of cholesterol desorption from sources in vivo is greater than from the 100 nm vesicle donors used to obtain the data in FIG. 36.

Example 2

Rearession of Atheromas in Rabbits Treated with Liposomes

This example demonstrates mobilization of cholesterol and regression of atheromas in rabbits treated with liposome compositions of the present invention. Plasma cholesterol concentration increased 2.5 times in liposome treated rabbits. Aortic lipid content decreased 25% in liposome treated animals. Egg phosphatidyl choline (EPC) was supplied by Princeton Lipids (Princeton, N.J.). A 0.5% cholesterol supplemented diet was obtained from Teklad Premier. Blood collection tubes and butterfly needles (23 gauge) were from Becton-Dickinson (Missisauga, Ontario). Ketamine, xylazine, heparin, Innovar and Euthanyl were supplied by MTC Pharmaceuticals, Janssen Pharmaceutics and Organon Technika (Ontario). Bio-Gel A-15m was purchased from Bio-Rad. Prepacked Solid Phase silica gel columns were acquired from Burdick & Jackson. All chemical and solvents were of analytical grade from BDH Chemicals (Vancouver, B.C.) Forty eight New Zealand White (NZW) rabbits were housed in wire cages at the Animal Unit of the Research Centre conforming to guidelines set by the Canadian Council on Animal Care and the University of British Columbia. The animals were maintained in a controlled temperature environment with a 12 hour dark/light cycle. Approximately 150 g of food were given per animal per diem. Water was freely given.

Lesions induced in rabbits as a result of maintaining the animals on cholesterol enriched diets for more than two months, do not regress for lengths of up to two years even when they are returned to standard rabbit chow. St. Clair, Prog. gardiovasc, Dis., 26:109–132 (1983). Even after cessation of cholesterol enriched diets, lesions have been noted to progress and increase in complexity. Prior et al., Arch. Path., VOL???:82–94 (1960).

Moreover, in cases where intermittent feeding schedules were administered or a low cholesterol-enriched diet was given over a period of years, lesions similar to the calcified ulcerated lesions observed in humans have been produced. Constantinides et al., Arch.Pathol., 70:81–92 (1961). The correlation between hypercholesterolemia and the onset and progression of atherosclerosis in the rabbit is well established. St. Clair, supra. To ensure that an equal distribution of animals were divided into the respective treatment groups, careful pairing of the animals was done. Initially, the 48 NZW weanlings were screened for responders to the 0.5% cholesterol enriched diet (Teklad diet 0533). The animals were fed the cholesterol diet for one week and plasma cholesterol concentrations monitored until returning to normal. Animals were matched by the extent of the rise in plasma cholesterol levels as well as the rate at which the levels returned to normal. This enabled an equal distribution of animals to be placed into two groups of 24 that were fed either standard rabbit chow or 0.5% cholesterol enriched rabbit chow for 20 weeks to induce atherosclerotic plaque formation. During this time, plasma lipid levels were monitored on a monthly basis. Two animals were euthanized due to complications probably associated with handling and were excluded from the final analyses. After the diet induction period, five animals from each group were sacrificed to verify the formation of lesions and serve as the standards against which the effectiveness of liposomal treatment was assessed. Thereafter, all remaining animals were fed regular rabbit chow until the conclusion of the study.

Rabbits were fed a 0.5% cholesterol-enriched diet for 20 weeks in order to induce intermediate lesions more significant than fatty streaks associated with shorter duration cholesterol-enriched diets. Chemical and histological analyses of aortas obtained from rabbits following the diet induction period, but prior to treatment, revealed plaques formed that were rich in lipid and surrounded by fibrous tissue. These plaques consisted of almost equivalent amounts of cholesterol and cholesterol ester. The aortic phospholipid in these animals was 15 plus or minus 4 gmol/g wet tissue and aortic total cholesterol was 114 plus or minus 28 gmol/g wet tissue (61 plus or minus 13 $\mu$mol/g cholesterol and 53 plus or minus 15 $\mu$gmol/g cholesterol ester). Animals maintained on a standard diet had aortic phospholipid levels of 4 plus or minus 0.3 $\mu$mol/g wet tissue and aortic total cholesterol levels of 10 plus or minus 1 $\mu$mol/g which was predominantly cholesterol. The degree of surface plaque involvement in cholesterol fed animals was 78 plus or minus 14%.

Based on the pairing of plasma cholesterol concentrations, 18 rabbits remaining from each diet group were separated into groups of 9 and were treated with EPC 1=100 at a dose of 300 mg/kg or the equivalent volume of saline. Treatment was initiated 4 weeks after return to standard rabbit chow and was given over a 100 day period. The treatment consisted of ten bolus injections of phospholipid or saline administered into the marginal ear vein. One injection was given every 10 days.

The rabbits ranged from 4–6 kg in weight. Each treatment of the vesicle-receiving rabbits required the preparation of approximately 150 mls of LUV100 at a concentration of 200 mg/ml. Typically, 6 gram aliquots of EPC were hydrated with 30 ml of filtered 150 AM NaCl, 20 AM HEPES (HBS), pH 7.4, in sterile 50 ml conical tubes, vortexed and kept overnight As described in Example 1 above, the resulting multilamellar vesicles (MLVs) were used to generate LUV100 by extrusion through two stacked polycarbonate filters of 100 nm pore size using a 10 ml water-jacketed thermobarrel Extruder (Lipex Biomembranes, Vancouver, B.C.), according to the method of Hope et al., Biochim Biophys, Acta, 812:55–65 (1985), incorporated herein by reference. Vesicle sizes were determined by quasi-electric light scattering (QELS) analyses utilizing a Nicomp Model 370 submicron laser particle sizer (Pacific Scientific, MD).

The vesicles used for the 10 treatments had an average diameter of 114 plus or minus 7 nm. A small dose of Innovar was given to promote calmness and vessel dilation in animals to ease routine bleedings necessary for plasma lipid analyses. To facilitate the final blood collections, ketamine (40 mg/kg) and xylazine (8 mg/kg) were given intramuscularly to sedate the animals.

Fifty units of heparin (Hepalean) followed by a lethal dose of phenobarbital (Euthanyl) were then perfused into the marginal ear vein before laparotomy. Organs were removed, rinsed in saline and immediately frozen in liquid nitrogen. The heart and full length aorta were collected in one section and kept in iced saline. The animals were sacrificed in roups of 8–10 on alternate days. The organs were randomized prior to processing and analyses.

Each aorta was separated from the heart at the aortic valve and was carefully cleaned to remove any adherent adventitial fat. The aortas were cut along the ventral surface, opened, and photographed on a black background. The photographs were used in conjunction with the negatives to aid in the collection of digitization data as well as to facilitate the division of the aortas into three regions: the arch, thoracic, and abdominal aortic segments as described by Rosenfeld et al., Atherosglerosis, 8:338–347 (1988), incorporated herein by reference.

Nine animals were in each of the 4 treatment groups: (1) vesicle-treated cholesterolfed animals (VC), (2) saline-treated cholesterol-fed animals (SC), (3) vesicle-treated normal diet animals (VN) and (4) saline-treated normal diet (SN). Six aortas from each group were allocated for lipid analyses and stored at −200 C. until analysis. The remaining three samples in each group were fixed in 10% neutral buffered formalin for at least 48 hours and used for gross staining with Sudan IV and histology. Holman et al., Lab. Invest., 7:42–47 (1958), incorporated herein by reference. At the time of lipid analysis, the aortas were patted dry and divided into the three segments.

Wet weight and length were measured and the aortic segments were homogenized (Polytron) in HBS. Two additional washes of the Polytron probe with HBS were collected for each segment to ensure complete homogenate recovery. Whole aortic segments were analyzed by digitization. In this analysis, photographic negatives obtained from all unstained aortas were illuminated generating an image using a Microcomputer Imaging Device (Imaging Systems). The percentage of plaque involvement was calculated by dividing the area occupied by surface plaque by the area of the entire aorta segment. Distinct differences were observed in the degree of shading of plaques and uninvolved aortic tissue.

Assessments of the percentage of atherosclerotic plaque involvement were performed by two observers and the results were averaged. Interobserver variation was within plus or minus 5%. Cholesterol and phospholipid content of the aortas and livers of the sacrificed animals were quantified following Bligh and Dyer extractions of the homogenates. Bligh and Dyer, Can. J. Biochem. Physiol.4 37:911–917 (1959), incorporated herein by reference. Total cholesterol, cholesterol, and cholesterol ester contents were determined according to the method of Rudel and Morris, J. Lipid Res.4 14:364–366 (1973), incorporated herein by reference.

Cholesterol and cholesterol esters were separated by silica gel chromatography on Burdick and Jackson prepacked 200 mg Solid Phase Silica Gel columns. Cholesterol esters were eluted with 1 ml methylene chloride. Cholesterol was collected following methylene chloride/methanol (95:5) elution after transferring the columns to a new carrier. Phospholipid content was measured according to Fiske and Subbarow, J. Biol. Chem., 66:375–400 (1924), incorporated herein by reference.

Lipoprotein lipid profiles were quantified by enzymatic procedures after phosphotungstic acid precipitation. Aliquots of aorta or liver homogenates were incubated overnight at 37 degrees C. with 1 ml of 1N NaOH. Thereafter, sodium dodecylsulphate (SDS) was added to the mixture to make a 1% solution needed to solubilize any remaining particulate matter. Protein content of the samples was quantified by the bicinchoninic acid (BCA) protein assay method (Pierce Chemical Company, Rockford, Ill.) after incubation for 1 hour at 600 C. and read at $A_{562}$ against an albumin standard.

Typically, 2–3 mm segments from the arch, thoracic, and abdominal aorta of three different animals within each treatment group were divided into left and right halves and embedded in paraffin. At least 8 segments from each region were prepared as blocks, depending on the length of the aorta. Alternate sections of 5 µm were adhered to gelatin coated slides from paraffin blocks and visualized with hematoxylin and eosin (H&E) or Weigart's-van Gieson's stains. Intima/media ratios of the different regions were calculated by initially measuring an average ratio from 3 photographs generated from each section and using this value to determine a final mean plus or minus standard deviation from all the sections made from the animals of each group.

The nature of plaques from animals sacrificed after the diet induction period, but prior to any treatment was examined after sections were made from segments held into place with tissue mount (OCT) on wooden stages and quick frozen in isopentane followed by liquid nitrogen.

Subsequently, alternate sections of 5 µm were adhered to polylysine coated slides and visualized with Sudan IV differentiated with Harris' hematoxylin, H&E—van Gieson's stains to highlight lipids and collagen.

Unless otherwise indicated, mean plus or minus standard deviation values are presented. The significance of the difference of the means was assessed by an analysis of variance using the two-sample t test. Only values of $P<0.05$ were considered significant.

Figure 42:
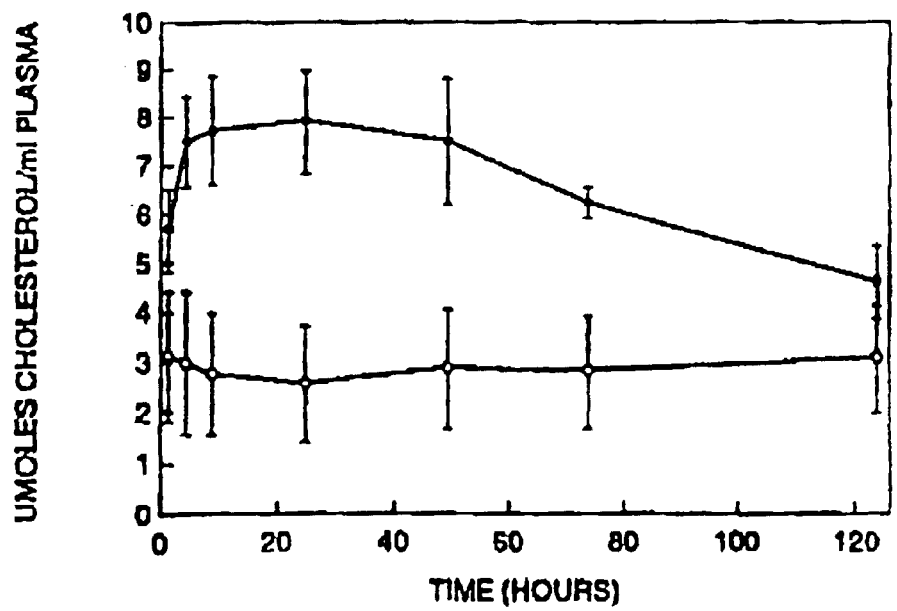
FIGS. 42–43 illustrates plasma cholesterol concentration changes in rabbits treated with liposomes and untreated rabbits.
Figure 43:
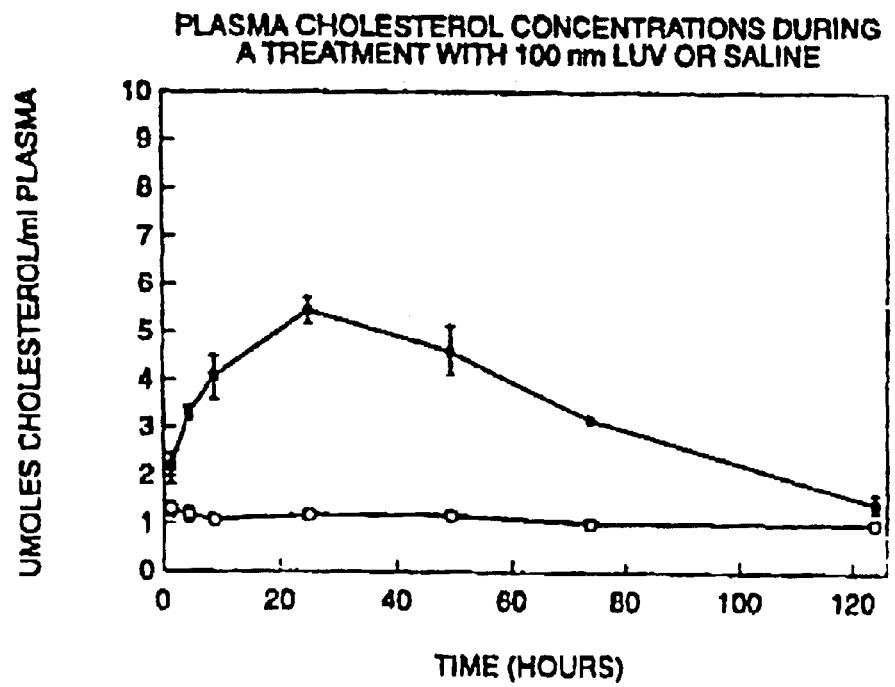
Figure 44:
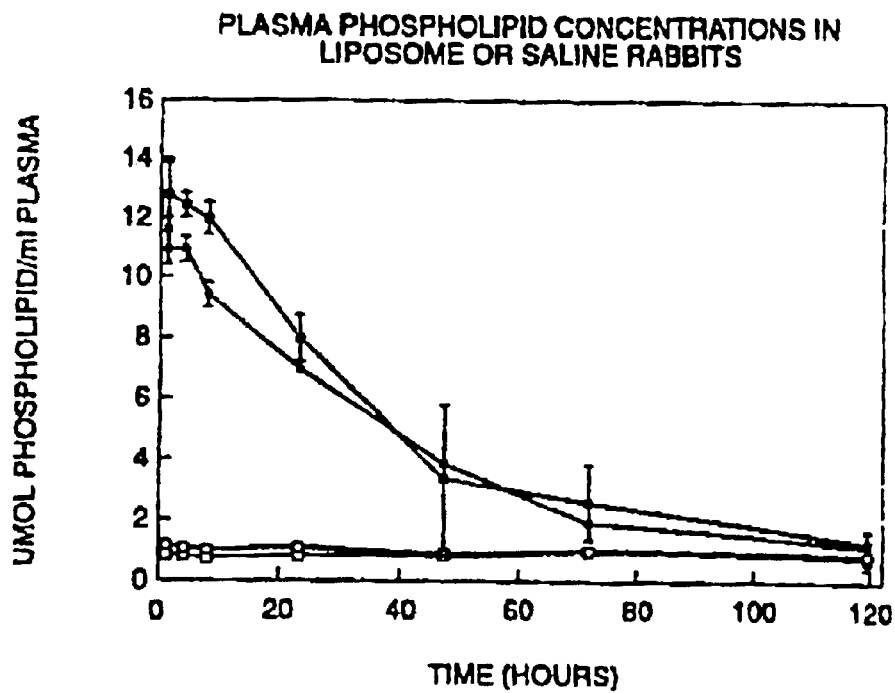
FIG. 44 illustrates plasma phospholipid concentration changes in rabbits treated with liposomes and untreated rabbits.

During the course of this study, animals maintained on the atherosclerotic diet exhibited plasma total cholesterol concentrations ranging from 5–10 times that of the control animals fed the standard diet while fed the cholesterol enriched diet. The cholesterol concentrations remained elevated (2–5 times higher) until the conclusion of the study even though standard rabbit chow was given during the treatment period. This is illustrated in a typical time course of cholesterol mobilization resulting from the infusion of 300 mg/kg EPC LUV100 or an equivalent volume of saline demonstrated in FIGS. 42–43. A comparison of control animals injected with saline demonstrates that animals previously fed the high cholesterol diet (panel A) maintained plasma cholesterol concentrations 3 times higher than animals maintained on the standard diet throughout the study (panel B) even though the cholesterol diet was terminated 10 weeks earlier. Despite the atherosclerotic animals having excess plasma cholesterol, an injection of LUV100 resulted in a dramatic 2.5 times increase in plasma cholesterol concentrations in both hyper- and normocholesterolemic animals when compared to saline treated counterparts. Plasma cholesterol levels peaked at 24 hours post-infusion before returning to baseline levels after 5 days. This time course correlates with the removal of vesicles from the circulation measured as total plasma phospholipid concentration illustrated in the clearance profiles shown in FIG. 44.

Although atherosclerotic animals had slightly higher total phospholipid concentrations, similar clearance kinetics of the injected vesicles were seen between normal and hypercholesterolemic rabbits. As demonstrated in Example 1 above, the amount of cholesterol accumulated and removed by liposomes with each infusion is a function of the rate of liposomal cholesterol uptake and the rate of vesicle clearance. Also, it was determined that all cholesterol above saline treated levels was associated with circulating liposomes by generating a cholesterol and phospholipid profile after separating vesicles from plasma by gel filtration. This showed that excess plasma cholesterol was associated with the vesicles and that >90% of the cholesterol was free cholesterol. Hence, an estimate of the mass of cholesterol removed from the circulation (mostly by the RES) was made by calculating the C:P ratios of vesicles at intervals following each injection from plasma phospholipid concentrations (vesicle-treated concentration minus saline-treated concentrations) and cholesterol (excess plasma concentration above the control concentration) at different time points during the experiments.

Figure 45:
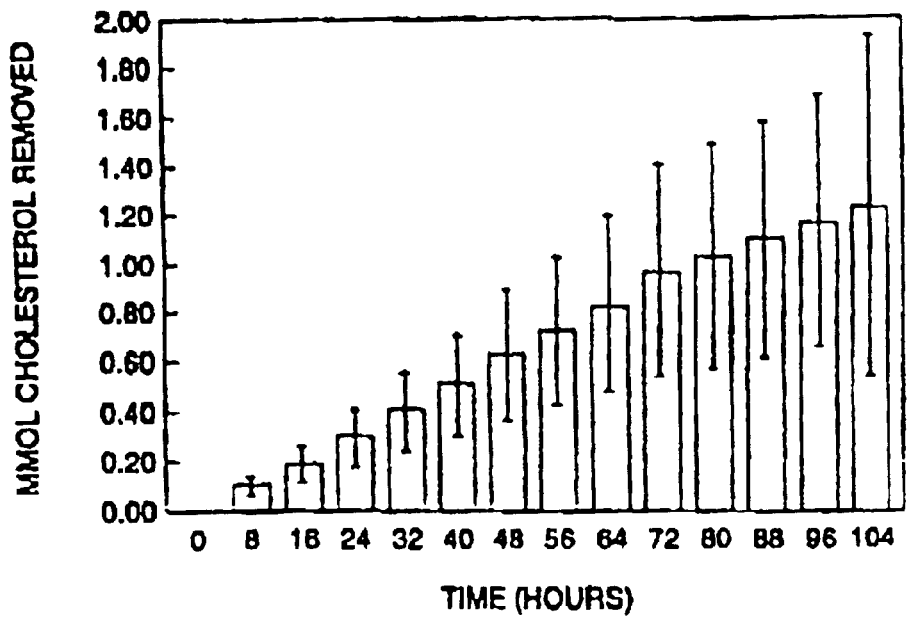
FIG. 45 demonstrates the quantity of cholesterol mobilized by liposomes during treatment of rabbits.

The plasma volume of the rabbits was approximately 150 ml. An estimate of the cholesterol removed was calculated employing the average C:P ratio measured for vesicles at each assay interval. This data is shown in FIG. 45. The data represents an average plus or minus a standard deviation expressed as mmol of cholesterol removed with each treatment in hypercholesterolemic animals and was calculated from data obtained from treatments 1, 4 and 10. The analysis was not continued beyond the point where less than 10% of the initial phospholipid dose remained in the circulation. Below this level, the measurement error was too large to determine accurate C:P ratios. After 104 hours it was estimated that approximately 1 mmol of cholesterol was removed from the circulation by the RES, which represents approximately 50 mole % of the injected phospholipid dose. Furthermore, based on plasma cholesterol concentrations measured in animals 24 h post-injection, each of the 10infusions of liposomes caused dramatic cholesterol mobilization.

Figure 46:
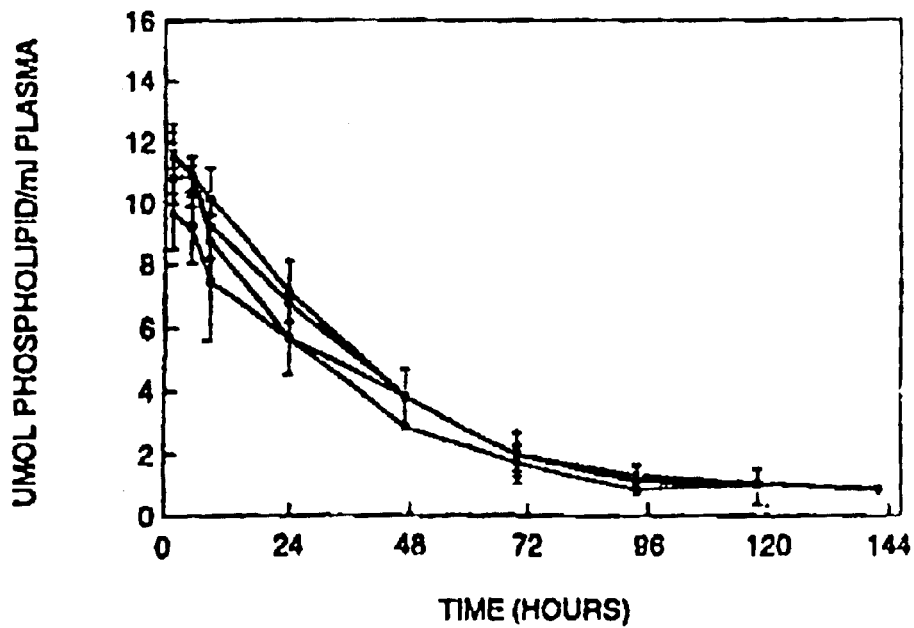
FIGS. 46–47 illustrates clearance profiles of liposomes injected into rabbits.
Figure 47:
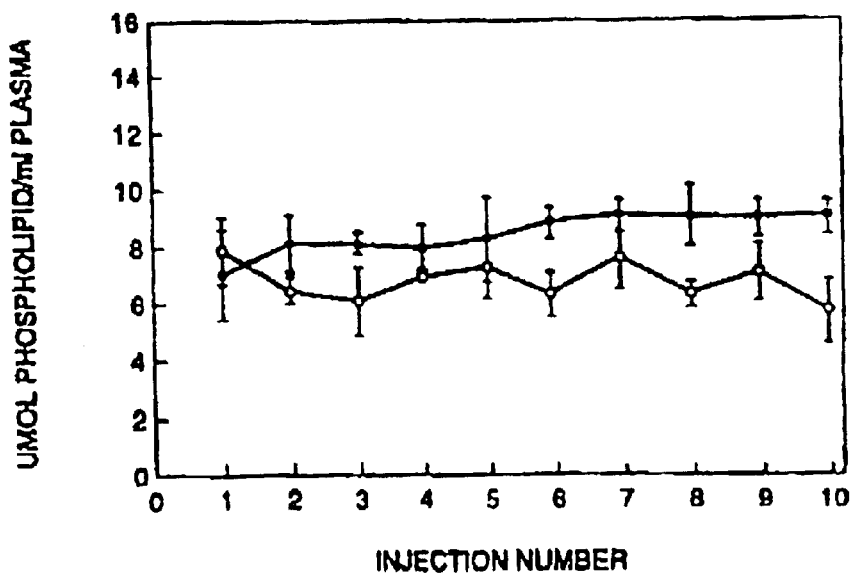

The ability of the animals to tolerate and remove repeated injections of phospholipid and the consequences of administering excess phospholipid on plasma lipid levels were examined. Chronic short term (one week) administration of Intralipid, an emulsion of triglycerides and phospholipids, causes increased LDL levels. Although the phospholipid content of Intralipid is comparable to the dose of 300 mg/kg LUV100 per injection of the present treatment regimen, Intralipid is generally given intravenously on a daily basis as a nutritional supplement. Each injection of 300 ml/kg EPC LUV100 apparently induces a transient 100-fold increase in plasma phospholipid concentrations and at the end of liposomal therapy (10 injections) each animal received an average total dose of 12–20 mmol (10–15 g) of phospholipid. The clearance profiles of several injections of EPC LUV100 in cholesterol fed rabbits is shown in FIG. 46. As illustrated, significant differences in the rates of vesicle clearance between injections were not detected. FIG. 47 shows that similar concentrations of vesicle phospholipid remain in the circulation 24 h post injection in both normo- and hypercholesterolemic animals following serial injections. If the ability of the fixed macrophages of the RES were compromised, increasing phospholipid levels would likely be detected during the later treatments. Furthermore, 5 days post-injection; the injected dose of liposome phospholipid was completely removed from the circulation and plasma phospholipid and cholesterol concentrations returned to baseline levels.

At the conclusion of the study, saline-treated cholesterol-fed animals maintained elevated plasma cholesterol levels whereas vesicle-treated animals had levels comparable to animals maintained on the standard diet. The reduction in plasma cholesterol concentrations of vesicle-treated atherosclerotic animals resulted from a reduction in both plasma LDL and HDL cholesterol concentrations although the relative proportions of HDL/LDL cholesterol were not affected.

No changes in the plasma lipid profiles (cholesterol, phospholipid or triglycerides) were detected in animals maintained on standard rabbit chow throughout the study. Plasma phospholipid levels in vesicle-treated animals were similar to their saline-treated counterparts despite the injection of approximately 15 grams of phosphatidylcholine per animal during liposomal therapy. These results, unlike those observed with Intralipid infusions, suggest that repeated administration of LUN100 given at 10 day intervals does not compromise RES function or normal plasma lipid homeostasis.

Figure 48:
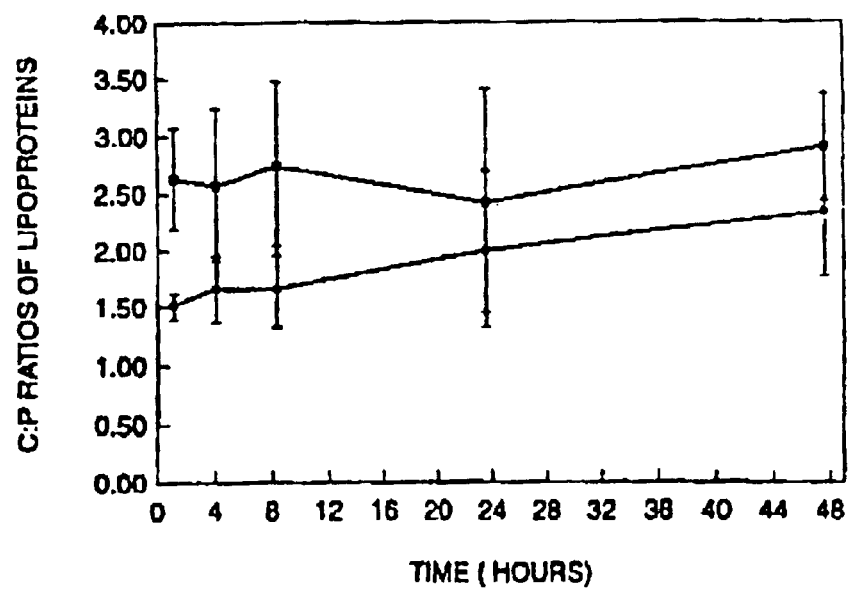
FIG. 48 demonstrates the cholesterol:phospholipid ratio of lipoproteins following liposome injection; and, FIGS. 49–51 illustrates aortic cholesterol content in liposome and saline treated rabbits.

Erythrocyte cholesterol remained constant throughout the infusions. However, a decrease in the C:P ratios of lipoproteins was detected over the first 24 hours. This C:P reduction gradually returned to normal levels after 48 hours (see FIG. 48). This time course mirrors cholesterol accumulation by the vesicles. These results suggest that the lipoprotein pool of cholesterol rapidly equilibrates with the vesicles and supports the hypothesis that liposomes generate cholesterol-poor lipoprotein particles that can access peripheral tissues and promote cellular cholesterol efflux.

The extent of lesion progression or regression was assessed by three complementary methods: (1) chemical lipid and protein assays to determine lesion bulk, (2) digitization of gross surface morphology to quantitate the degree of plaque involvement, and (3) histochemistry to examine the nature and depth of the lesions. Despite elevated plasma cholesterol concentrations persisting in animals returned to standard rabbit chow, saline-treated animals were found to have arterial wall cholesterol content expressed per gram wet weight of 94 plus of minus 12 $\mu$mol/g total cholesterol, 58 plus or minus 6 $\mu$mol/g free cholesterol and 37 plus or minus 9 $\mu$mol/g cholesterol esters with an average surface plaque involvement of 77 plus or minus 17%. Although there appears to be slight reduction in the cholesterol ester content, the values of the lipid content of saline-treated animals were not significantly different from values found in atherosclerotic animals prior to treatment indicating that there was no progression or regression of lesions after 4 months. On the other hand liposome-treated animals were found to have significantly less cholesterol content of the entire aorta with levels of 85 plus or minus 8 $\mu$mol/g total cholesterol, 48plus or minus $\mu$mol/g free cholesterol and 37 plusor minus 6 $\mu$mol/g cholesterol esters. Because there were no significant differences between the lipid content of animals before or after saline treatment, the reductions in plaque cholesterol content between liposome- and saline-treated animals indicates regression, not simply decreased progression, of plaques.

Aortic lipid content was expressed per gram of protein weight as wet weights are likely to be more variable. No significant differences were found between the protein levels in both saline- and vesicle-treated animals. The protein content of the aortas to be 0.41 g protein/g wet weight and 0.43 g protein/g wet weight, respectively.

Figure 49:
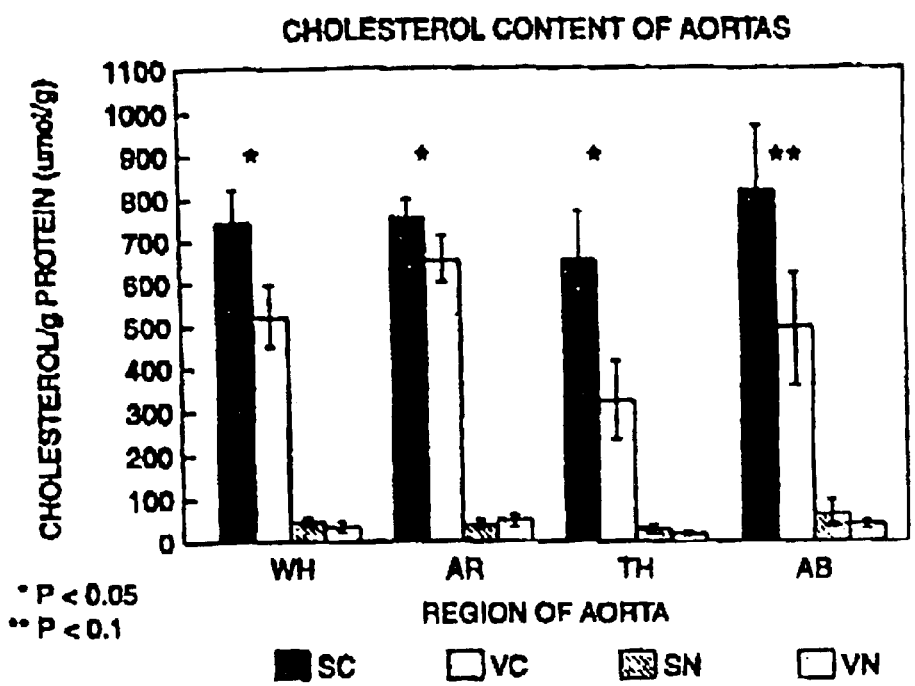
Figure 50:
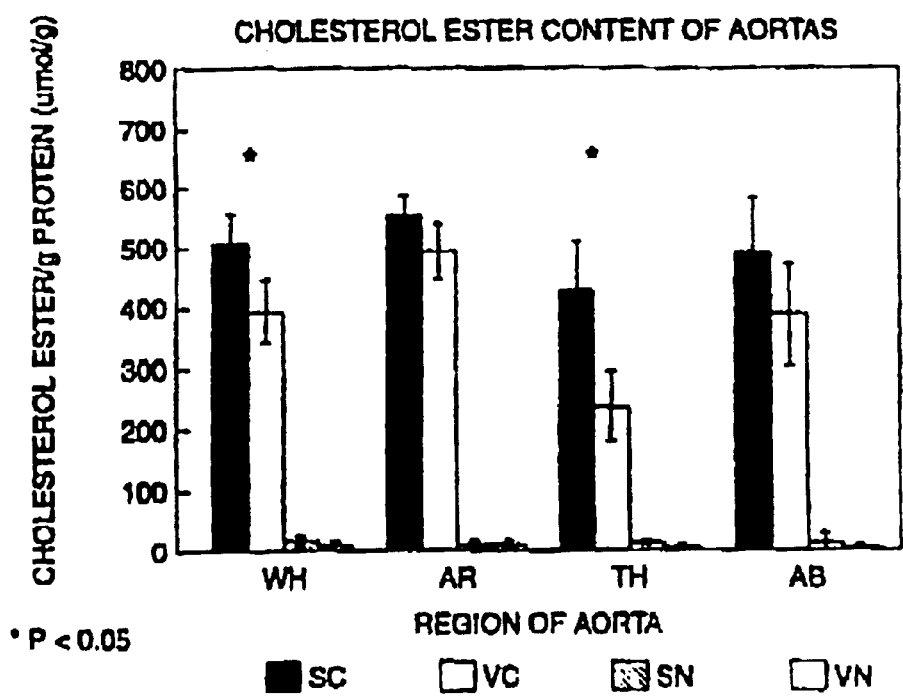

Expressing the data per g protein, liposomal therapy resulted in a 25% reduction in total cholesterol content of the entire aorta of vesicle-treated animals compared to saline-treated controls. By segment, there was a 48% reduction seen in thoracic aorta cholesterol levels and small reductions in the arch and abdominal aortas (see FIG. 49). Significant reductions in the cholesterol ester levels in vesicle-treated animals were also noted and again the thoracic aorta demonstrated the greatest decrease (see FIG. 49). In addition to decreased cholesterol content, aortic phospholipid levels in vesicle-treated atherosclerotic animals decreased, although not to the level of statistical significance.

Figure 51:
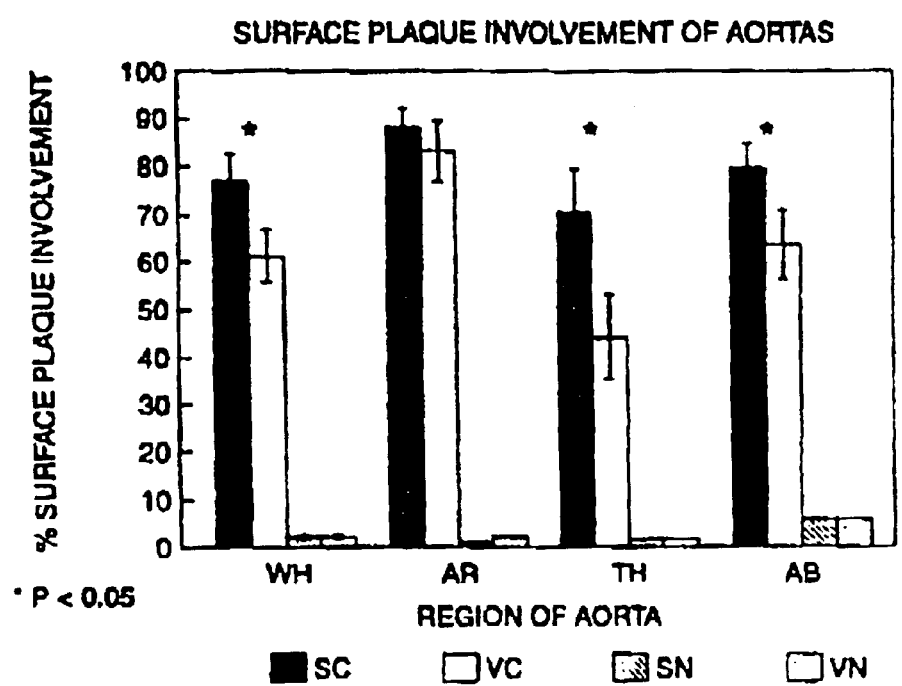

In order to maximize the number of animals within each group, all negatives generated from photographed unstained aortas were digitized. Gross Sudan IV staining of 3 aortas from each treatment group confirmed the same degree of surface plaque involvement as unstained aortas. The area of plaque involvement was determined by digitization. The data is shown in FIG. 51. Liposome-treated, cholesterol fed rabbits demonstrated 61 plus or minus 13% involvement of the entire aorta compared to 77 plus or minus 17% involvement of saline-treated animals, representing an overall 16% reduction of surface plaque. In agreement with the reductions in cholesterol content detected by lipid analyses, the thoracic aorta exhibited the most benefit from liposome infusion with digitization analysis and displayed a 26% reduction in plaque involvement, whereas the abdominal aorta revealed a 16% reduction. There was a slight reduction in the degree of surface plaque involvement of the arch that failed to reach statistical significance. No significant differences between treated and untreated control animals maintained on the standard diet were seen and both groups showed essentially no plaque involvement.

Histochemical analysis revealed extensive raised plaques (intimal thickening) in the cholesterol fed animals as expected from gross surface morphology inspection. Whereas digitization quantitated the extent of plaque involvement, histochemical analyses allows the depth and nature of the lesions to be assessed. Generally, the plaques exhibited extensive intimal thickening due to stratified lipid deposits that were surrounded by a collagenous network. The arch region was noted to display more advanced lesions of apparent crystalline cholesterol deposits and showed a few isolated necrotic foci as detected with H&E staining.

Representative sections of the thoracic aorta of vesicle-treated and saline treated animals are illustrated in FIG. 14. It can be seen that lesions of animals treated with vesicles (panel B) manifest less lipid deposits and show moderately reduced plaque thickening when compared to saline treated atherosclerotic animals (panel C). This is quantified in Table 2 summarizing the data obtained from the analysis of pictures taken from multiple sections used to assess the severity of lesions present in the arch, thoracic or abdominal aorta of atherosclerotic animals. As can be seen, a decrease in the intima/medial ratios in the arch and thoracic regions of liposome treated animals were detected, whereas no changeswere detected in the abdominal aorta. No apparent differences were detected between treated and untreated animals maintained on the standard diet throughout the study.

Cholesterol feeding of rabbits often leads to the accumulation of cholesterol in a number of tissues including the liver. However upon the return to regular rabbit chow, non-arterial tissue cholesterol levels often revert to normal within a month. Liver cholesterol content was measured in order to gain insight into whether (1) increased biliary excretion of cholesterol might be occurring in liposome treated animals due to massive deposition of the injected phospholipids in the liver resulting in reduced liver cholesterol levels or (2) there was a detrimental accumulation of cholesterol mobilized by the liposomes to the liver. In atherosclerotic animals, liposome-treated rabbits demonstrated a slight reduction in liver cholesterol content having average levels of 8 µmol/g that are comparable to control animals fed the standard diet. Saline-treated animals exhibited average levels of 11 µmol/g. This difference was not statistically significant.

All publications, patents and patent applications mentioned in this specification are herein incorporated by reference into the specification to the same extent as if each individual publication, patent or patent application was specifically and individually indicated to be incorporated herein by reference.

In various aspects, the invention provides:

a pharmaceutical composition consisting essentially of large liposomes comprised of phospholipids substantially free of sterol, whereby the composition forces the reverse transport of cholesterol from peripheral tissues to the liver in vivo.

a composition for controlling cholesterol related genes, enzymes and other compounds while forcing the reverse transport of lipids peripheral tissues to the liver consisting essentially of large liposomes sized and shaped to interact with molecules interacting with the genes, enzymes or other compounds, the large liposomes being substantially free of sterol.

a pharmaceutical composition for mobilizing peripheral cholesterol and sphingomyelin that enters the liver of a subject consisting essentially of liposomes of a size and shape larger than fenestrations of an endothelial layer lining hepatic sinusoids in the liver, whereby the liposomes are large enough not to penetrate most of the fenestrations and interact with hepatic parenchymal cells in the liver.

a pharmaceutical kit for mobilizing peripheral cholesterol and sphingomyelin comprising: a first container having a pharmaceutical composition for reducing the size of arterial lesions that enters the liver of a subject consisting essentially of liposomes of a size and shape larger than fenestrations of an endothelial layer lining hepatic sinusoids in the liver, whereby the liposomes are large enough not to penetrate most of the fenestrations and interact with hepatic parenchymal cells; and a second container having a compound, the compound selected from the group consisting of a small acceptor of cholesterol and a drug that increases endogenous small acceptors of cholesterol.

a kit in which the small acceptor is selected from the group consisting of a high-density lipoprotein, a phospholipid protein complex having a group selected from the group consisting of apoA-I, apoA-II, apoA-IV, apoE, apoA-I milano, synthetic fragments thereof, natural fragments thereof, an amphipathic protein, and an amphipathic peptide, the protein substantially free of phospholipid, small phospholipid liposomes, and a small cholesterol accepter; the drug including an agent that raises endogeneous HDL concentrations, the agent selected from the group consisting of nicotinic acid, ethanol, a fibric acid, a cholesterol synthesis inhibitor, a drug that increases HDL concentrations, an amphipathic compound, and derivatives thereof.

an improved pharmaceutical composition for reducing the size of arterial lesions that enters the liver of a subject, the composition consisting essentially of liposomes, in which the improvement comprises an anti-oxidant and derivatives thereof.

a composition further comprising means for providing for the control and regulation of atherogenic lipoprotein concentrations.

A composition further comprising, in combination, an agent for controlling plasma concentrations of atherogenic lipoproteins, the agent selected from the group consisting of large liposomes, anti-hyperlipidemic drugs, and concentration lowering compounds other than large liposomes and anti-hyperlipidemic drugs.

a composition in which the means regulates an atherogenic lipoprotein selected from the group consisting of LDL, VLDL, IDL, β-VLDL, Lp(a), a lipoprotein containing apolipoprotein-B, oxidized lipoproteins, and modified lipoproteins.

a pharmaceutical composition in which the anti-oxidant is selected from the group consisting of vitamin E, tocopherol, butyl hyroxy toluene (BHT), EDTA, chelators, ascorbate, probucol, carotenoids, derivates thereof, a material resistant to oxidation, a material inhibiting oxidation, and combinations and derivatives thereof.

a composition in which the tocopherol is added at about or above 0.1 mole %.

a composition in which the tocopherol is added at below about 0.1 mole %.

a composition in which the ascorbate is added at about or above 0.1 mole %.

a composition in which the ascorbate is added at below about 0.1 mole %.

an improved pharmaceutical composition for modifying membranes, cells, tissues, extracellular structures, including reducing the size, instability, and other properties of arterial lesions that enters the liver of a subject while simultaneously avoiding harmful disruptions of cholesterol homeostasis, the improvement comprising palmitoyl-oleyl-phosphatidylcholine.

the composition described above in which the composition comprises large liposomes.

an improved pharmaceutical composition for modifying membranes, cells, tissues, extracellular structures, including reducing the size, instability, and other properties of arterial lesions that enters the liver of a subject while simultaneously avoiding harmful disruptions of cholesterol homeostasis, the improvement comprising a double bond in a second fatty acyl chain of components of the composition, whereby the composition is more fluid and more readily accepts cholesterol and other material, and donates material to the membranes, cells, tissues, and extracellular structures.

an improved pharmaceutical composition for modifying membranes, cells, tissues, extracellular structures, including reducing the size, instability, and other properties of arterial lesions that enters the liver of a subject while simultaneously avoiding harmful disruptions of cholesterol homeostasis, the improvement comprising PEG-liposomes in an effective amount, whereby the composition is more fluid and more readily accepts cholesterol and other accepted material, and donates donated material to the membranes, cells, tissues, and extracellular structures.

a composition in which the accepted material is selected from the group consisting of sphingomyelin and oxidized lipids.

a composition in which the donated material is selected from the group consisting of phospholipid, phosphatidylcholine, and anti-oxidants.

an improved dialysis apparatus for the treatment of a patient in which the improvement comprises means for administering a therapeutically effective amount of a lipid acceptor during the treatment of a subject at or during a suitable period of time.

an apparatus in which the lipid acceptor is selected from the group consisting of a multiplicity of large liposomes comprised of phospholipids substantially free of sterol and small acceptors.

an apparatus in which the means for administering is selected from the group consisting of means for extracorporeal administration of the lipid acceptor and means for intracorporal administration of the lipid acceptor.

an apparatus in which the means for administering the lipid acceptor is a means other than the means selected from the group consisting of means for extracorporeal administration and means for intracorporal administration.

an improved mode of operating a dialysis apparatus in which the improvement comprises a lipid acceptor administration mode for administering or emitting a therapeutically effective amount of a lipid acceptor by way of a lipid acceptor administration means.

an improved mode of operating a dialysis apparatus in which the lipid acceptor is selected from the group consisting of a multiplicity of large liposomes comprised of phospholipids substantially free of sterol and small acceptors.

An improved mode of operating a dialysis apparatus in which the administration means is selected from the group consisting of means for extracorporeal administration and means for intracorporal administration.

an apparatus in which the administration means is a means other than the means selected from the group consisting of means for extracorporeal administration and means for intracorporal administration.

an improved method of angioplasty or cardiac catheterization in which the improvement comprises the step of administering a therapeutically effective amount of a lipid acceptor during angioplasty or cardiac catheterization of a subject.

an improved method of angioplasty in which the lipid acceptor is selected from the group consisting of a large liposome comprised of phospholipids substantially free of sterol and small acceptors.

a method of angioplasty in which the administration of the lipid acceptor occurs at or over an effective period of time.

a method of angioplasty in which the administration of the lipid acceptor occurs simultaneously with the angioplasty.

a method of angioplasty in which the effective period of time is in the range of about 1 minute to about two years from the time of the angioplasty.

an improved angioplasty apparatus in which the improvement comprises: lipid acceptor administration means for administering a therapeutically effective amount of a lipid acceptor.

an improved angioplasty apparatus further comprising co-administration means for administering the lipid acceptor and a diagnostic agent.

an improved mode of operating an angioplasty or cardiac catheterization apparatus in which the improvement comprises a mode of operation for administering a therapeutically effective amount of a lipid acceptor from the apparatus or component thereof into a vessel.

an improved mode of operating an angioplasty or cardiac catheterization apparatus in which the lipid acceptor is selected from the group consisting of a large liposome comprised of phospholipids substantially free of sterol and small acceptors.

a mode of altering the normal mode of processing of atherogenic lipoproteins in a warm blooded mammal comprising the step of administering a liposome composition to the mammal, the liposome composition selected from the group consisting of unilamellar liposomes and multilamellar liposomes, the liposomes having an average diameter of about 50–150 nanometers, in which LDL levels in the subject do not increase.

a method of controlling cholesterol metabolism in hepatic parenchymal cells in a warm blooded mammal in vivo through cell—cell communication from Kupffer cells to the parenchymal cells, comprising the step of administering a liposome composition to the mammal, the liposome composition selected from the group consisting of large unilamellar liposomes and large multilamellar liposomes, the liposomes having an average diameter of about 50–150 nanometers, in which LDL levels in the mammal do not increase.

a mode of controlling cholesterol metabolism in which the liposome composition is given periodically.

a mode of controlling cholesterol metabolism in which the liposome composition is given more than once.

a mode in which the liposomes have diameters larger than about 50 nm.

a mode in which the liposomes have diameters larger than about 80 nm.

a mode in which the liposomes have diameters larger than about 100 nm.

a mode in which administration is selected from the group of parenteral administration, intravenous administration, intra-arterial administration, intramuscular administration, subcutaneous administration, transdermal administration, intraperitoneal administration, intrathecal administration, via lymphatics, intravascular administration, including administration into capillaries and arteriovenous shunts, rectal administration, administration via a chronically indwelling catheter, and administration via an acutely placed catheter.

a mode in which about 10 to about 1600 mg/kg/dose of the liposome composition is administered.

a mode in which the liposome composition is given in repeated doses.

a mode in which the liposomes are phospholipids substantially free of sterol and in the range of about 50–150 nm in approximate diameter.

a mode in which the liposomes are phospholipids substantially free of sterol.

a mode in which the liposomes are phospholipids selected from the group consisting of phosphatidyl choline, phosphatidyl glycerol, palmitoyl-oleoyl phosphatidyl choline, combinations thereof, and derivatives thereof.

a method of regulating hepatic parenchymal cell cholesterol content, the cell having at least one gene selected from the group consisting of a gene for an LDL receptor, a gene for HMG-CoA reductase, a gene for cholesterol 7-alpha-hydroxylase, and a gene regulating a function involved in cholesterol homeostasis; and, homeostasis thereof, comprising the step of administering an effective amount of a multiplicity of large liposomes comprised of phospholipids substantially free of sterol during a period of time.

a method described above further comprising the steps of periodically assaying a property with an assay, the property selected from the group consisting of concentration, composition, and characteristic of atherogenic lipoproteins in plasma with an assay during the treatment period to assess the plasma atherogenic lipoprotein and to obtain a atherogenic lipoprotein profile, and adjusting the administration in response to the profile.

a method described above in which the assay is selected from the group consisting of an assay of plasma esterified cholesterol, an assay of plasma apolipoprotein-B, a gel filtration assay of plasma, an ultracentrifugal assay of plasma, a precipitation assay of plasma, an electrophoretic assay, an electron microscopic assay, an immuno-turbidometric assay, and an assay of lipoprotein composition, size or function.

a method described above further comprising the step of enhancing tissue penetration of a cholesterol acceptor and enhancing extraction of tissue cholesterol and other exchangeable material with co-administration of an effective amount of a compound, the compound selected from the group consisting of a small acceptor of cholesterol, an amphipathic compound, and a drug that increases endogenous small acceptors of cholesterol.

a method described above in which the small acceptor is selected from the group consisting of a high-density lipoprotein, a phospholipid protein complex having a group selected from the group consisting of apoA-I, apoA-II, apoA-IV, apoE, synthetic fragments thereof, natural fragments thereof, an amphipathic protein, and an amphipathic peptide, the protein substantially free of phospholipid, small phospholipid liposomes, and a small cholesterol acceptor; the drug including an agent that raises endogenous HDL concentrations, the agent selected from the group consisting of nicotinic acid, ethanol, a fibric acid, a cholesterol synthesis inhibitor, a drug that increases HDL concentrations, and derivatives thereof.

a method described above in which the co-administration of the compound is simultaneous with the administration of the large liposomes.

a method described above in which the co-administration of the compound is separated in time from the parenteral administration of the therapeutically effective amount of a multiplicity of the large liposomes by an effective time period.

a method described above in which the effective time period is in the range of about 1 minute to about two weeks.

a method described above in which the effective amount is in the range of about 10 to about 1600 mg/kg/dose.

a method described above in which the liposomes are given in repeated doses.

a method described above further comprising the step of controlling the expression of the genes by the parenteral administration of a multiplicity of the large liposomes.

a method described above in which the parenchymal cell functions in a system having hepatic sinusoids, an endothelial layer lining the hepatic sinusoids, and fenestrations; and, in which the large liposomes are of a size and shape larger than the fenestrations of the endothelial layer lining the hepatic sinusoids or in which the large liposomes optionally having other properties that prevent the large liposomes from penetrating the fenestrations, whereby the large liposomes have properties to prevent the ready penetration of the fenestrations.

a method described above in which the large liposomes are selected from the group consisting of uni-lamellar liposomes and multi-lamellar liposomes.

a method described above in which the liposomes have diameters larger than about 50 nm.

a method described above in which the liposomes have diameters larger than about 80 nm.

a method described above in which the liposomes have diameters larger than about 100 nm.

a method described above in which administration is selected from the group of intravenous administration, intra-arterial administration, intramuscular administration, subcutaneous administration, transdermal administration, intrathecal administration, via lymphatics, intravascular administration, rectal administration, via a chronically indwelling catheter or other device, via an acutely placed catheter or other device, and intraperitoneal administration.

a method of suppressing hepatic expression of a cholesterol ester transfer protein gene in a warm blooded mammal in vivo comprising the step of parenterally administering an effective amount of a multiplicity of large liposomes comprised of phospholipids, the phospholipids selected from the group of phospholipids substantially free of sterol and phospholipids containing sterol, for an effective period of time, whereby plasma LDL and HDL are controlled as a result of the administration.

a method described above further comprising the step of periodically assaying plasma LDL concentrations with an assay during the treatment period to assess the plasma LDL.

a method described above in which the assay is selected from the group consisting of an assay of plasma esterified cholesterol, an assay of plasma apolipoprotein-B, a gel filtration assay of plasma, an ultracentrifugal assay of plasma, a precipitation assay of plasma, an electrophoretic assay, an electron microscopic assay, an immuno-turbidometric assay of plasma, and an assay of lipoprotein composition, size or function.

a method described above in which the liposomes are given periodically.

a method described above n which the effective amount is in the range of about 10 mg/kg/dose to about 1600 mg/kg/dose.

a method described above further comprising the step of enhancing tissue penetration of a cholesterol acceptor and enhancing extraction of tissue cholesterol and other exchangeable material with co-administration of an effective amount of a compound, the compound selected from the group consisting of a small acceptor of cholesterol, an amphipathic compound, and a drug that increases endogenous small acceptors of cholesterol.

a method described above in which the small acceptor is selected from the group consisting of a high-density lipoprotein, a phospholipid protein complex having a group selected from the group consisting of apoA-I, apoA-II, apoA-IV, apoE, synthetic fragments thereof, natural fragments thereof, an amphipathic protein, and an amphipathic peptide, the protein substantially free of phospholipid, small phospholipid liposomes, and a small cholesterol acceptor; the drug including an agent that raises physiologic HDL concentrations, the agent selected from the group consisting of nicotinic acid, ethanol, a fibric acid, a cholesterol synthesis inhibitor, a drug that increases HDL concentrations, and derivatives thereof.

a method described above further comprising the step of periodically assaying plasma LDL concentrations with an assay to assess the plasma LDL.

a method described above in which the assay is selected form the group consisting of an assay of plasma esterified cholesterol, an assay of plasma apolipoprotein-B, a gel filtration assay of plasma, an ultracentrifugal assay of plasma, a precipitation assay of plasma, an electrophoretic assay, an electron microscopic assay, and a immuno-turbidometric assay of plasma.

a method described above in which the co-administration of the compound with the administration of the large liposomes is simultaneous.

a method described above in which the co-administration of the compound is separated in time from the parenteral administration of the therapeutically effective amount of a multiplicity of the large liposomes by an effective time period.

a method described above in which the separation in time is in the range of about 1 minute to about two weeks.

a method described above in which the large liposomes are of a size and shape larger than fenestrations of an endothelial layer lining hepatic sinusoids or in which the large liposomes optionally having other properties that prevent the large liposomes from penetrating the fenerstrations, whereby the large liposomes have properties to prevent the ready penetration of the fenestrations.

a method described above in which the large liposomes are selected from the group consisting of uni-lamellar liposomes and multi-lamellar liposomes.

a method described above in which the liposomes have diameters larger than about 50 nm.

a method described above in which the liposomes have diameters larger than about 80 nm.

a method described above in which the liposomes have diameters larger than about 100 nm.

a method of controlling hepatic expression of a gene while forcing the reverse transport of cholesterol from peripheral tissues to the liver, comprising the step of parenterally administering a therapeutically effective amount of a multiplicity of large liposomes comprised of phospholipids substantially free of sterol for a treatment period, the effective amount administered in a dosage, the dosage selected from a single dose and repeated doses.

a method of controlling plasma LDL levels, hepatic cholesterol homeostasis, arterial enzymes, platelet function, and hepatic gene expression, comprising the step of parenterally administering a therapeutically effective amount of a multiplicity of large liposomes comprised of phospholipids substantially free of sterol for a treatment period, the effective amount administered in a dosage, the dosage selected from a single dose and repeated doses.

a method described above further comprising the step of diagnosing the efficacy of the administration by taking a measurement of enzyme activity, the measurement selected from the group consisting of a measurement of an arterial lipase activity, a measurement of arterial triglyceride lipase activity, a cholesterol esterase activity, a measurement of lysophospholipase activity, a measurement of an arterial lipid esterase activity, a measurement of arterial ACAT activity, a measurement of endothelial-derived relaxing factor, a measurement of intracellular calcium concentration in arterial cells, a measurement of arterial cell proliferation, an assay of arterial enzymes, an assay in the presence of calcium channel blockers, a measurement of nitric oxide synthesis, an assay of arterial uptake of liposomes, an assay of arterial uptake, accumulation and retention of lipoproteins, an assay of arterial retention of liposomes, an assessment of platelet function, an assessment of arterial function, an assessment of gene function, and a measurement of an effect of a biologically active substrate of the enzyme.

a method described above in which the substrate is lysophosphatidylcholine.

a method described above in which the atherogenic lipoprotein is selected from the group consisting of LDL, VLDL, IDL, Lp(a), β-VLDL and a lipoprotein that comprises apolipoprotein B.

a method described above in which the parenchymal cell functions in a system having hepatic sinusoids, an endothelial layer lining the hepatic sinusoids, and fenestrations; and, in which the large liposomes have properties that provide for the slow and steady delivery of cholesterol to the liver, and reduce protein uptake.

a method described above further comprising the steps of periodically assaying a CETP property, the property selected from the group consisting of plasma CETP concentration and CETP activity and adjusting the effective amount in response thereto.

a method described above in which an atherogenic lipoprotein selected from the group consisting of LDL, VLDL, IDL, Lp(a), β-VLDL and a lipoprotein that comprises apolipoprotein B, is controlled.

a method described above further comprising the steps of periodically assaying a property, the property selected from the group consisting of concentration, composition, and characteristic of atherogenic lipoproteins in plasma with an assay during the treatment period to assess the plasma atherogenic lipoprotein and to obtain a atherogenic lipoprotein profile, and adjusting the parenteral administration in response to the profile.

a method described above further comprising the steps of periodically assaying a CETP property, the property selected from the group consisting of plasma CETP concentration and CETP activity and adjusting the effective amount in response thereto.

a method described above in which an atherogenic lipoprotein selected from the group consisting of LDL, VLDL, IDL, Lp(a), β-VLDL and a lipoprotein that comprises apolipoprotein B, is controlled.

a method described above further comprising the steps of periodically assaying a property, the property selected from the group consisting of concentration, composition, and characteristic of atherogenic lipoproteins in plasma with an assay during the treatment period to assess the plasma atherogenic lipoprotein and to obtain a atherogenic lipoprotein profile, and adjusting the parenteral administration in response to the profile.

a method described above in which the gene is selected from the group consisting of genes controlling the hepatic expression of 7-alpha hydroxylase, hepatic expression of an LDL receptor, hepatic expression of HMG Co A reductase, and derivatives thereof.

a method of forcing the reverse transport of cholesterol from peripheral tissues to the liver in vivo while controlling plasma LDL concentrations comprising the step of parenterally administering a therapeutically effective amount of a multiplicity of large liposomes comprised of phospholipids substantially free of sterol for a treatment period, whereby the liposomes pick-up the cholesterol during the treatment period.

a method described above further comprising the step of periodically assaying plasma LDL concentrations with an assay during the treatment period to assess the plasma LDL concentrations and obtain an LDL profile, and adjusting the parenteral administration in response to the LDL profile.

a method described above in which the assay is selected from the group consisting of an assay of plasma esterified cholesterol, an assay of plasma apolipoprotein-B, a gel filtration assay of plasma, an ultracentrifugal assay of plasma, a precipitation assay of plasma, an immuno-turbidometric assay of plasma, an electrophoretic assay, an electron microscopic assay, a function assay, a compositional assay, and a structural assay.

a method described above in which the large liposomes are of a size and shape larger than fenestrations of an endothelial layer lining hepatic sinusoids in the liver, whereby the liposomes are too large to readily penetrate the fenestrations.

a method described above in which the therapeutically effective amount is in the range of about 10 mg to about 1600 mg phospholipid per kg body weight per dose.

a method described above in which the liposomes are given periodically during the treatment period.

a method described above in which the large liposomes are selected from the group consisting of uni-lamellar liposomes and multi-lamellar liposomes.

a method described above in which the liposomes have diameters larger than about 50 nm.

a method described above in which the liposomes have diameters larger than about 80 nm.

a method described above in which the liposomes have diameters larger than about 100 nm.

a method described above in which parenteral administration is selected from the group of intravenous administration, intra-arterial administration, intramuscular administration, subcutaneous administration, transdermal administration, intraperitoneal administration, intrathecal administration, via lymphatics, intravascular administration, including administration into capillaries and arteriovenous shunts, rectal administration, administration via a chronically indwelling catheter, and administration via an acutely placed catheter.

a method described above further comprising the step of enhancing tissue penetration of a cholesterol acceptor and increasing extraction of tissue cholesterol and other exchangeable material by co-administration of an effective amount of a compound, the compound selected from the group consisting of a small acceptor of cholesterol and a drug that increases endogenous small acceptors of cholesterol.

a method described above in which the small acceptor is selected from the group consisting of a high-density lipoprotein, a phospholipid protein complex having a group selected from a group consisting of apoA-I, apoA-II, apoA-IV, apoE, synthetic fragments thereof, natural fragments thereof, an amphipathic compound, including amphipathic compounds that are not a protein, an amphipathic protein, and an amphipathic peptide, the protein substantially free of phospholipid, small phospholipid liposomes, and a small cholesterol acceptor; the drug including an agent that raises physiologic HDL concentrations, the agent selected from the group consisting of nicotinic acid, ethanol, a fibric acid, a cholesterol synthesis inhibitor, a drug that increases HDL concentrations, and derivatives thereof.

a method of beneficially altering arterial function, blood platelet function, and controlling plasma LDL concentrations and hepatic cholesterol homeostasis in a warm blooded mammal comprising the step of parenterally administering a therapeutically effective amount of a multiplicity of large liposomes comprised of phospholipids substantially free of sterol for a treatment period with or without administration of other agents, the other agents optionally including small acceptors and LDL lowering agents.

a method described above further comprising the step of taking a measurement of arterial function, the measurement selected from the group consisting of a measurement of endothelial-derived relaxing factor, a measurement of intracellular calcium concentration in arterial cells, a measurement of arterial cell proliferation, an assay of arterial enzymes, an assay in the presence of calcium channel blockers, an assay of arterial uptake, accumulation and retention of lipoproteins, an assay of arterial accumulation of liposomes, an assay of arterial retention of liposomes, an assay of gene products, and an assay of arterial cell functions.

a method of beneficially altering blood platelet function while controlling plasma LDL concentrations, arterial function, hepatic cholesterol homeostasis and the platelet function in a mammal comprising the step of parenterally administering an effective amount of a multiplicity of large liposomes comprised of phospholipids substantially free of sterol for a treatment period, the liposomes administered with or without other agents.

a method described above further comprising the step of taking a measurement of platelet function, the measurement selected from the group consisting of a measurement of a ratio of cholesterol to phospholipid in the platelets, a measurement of platelet reactivity, a measurement of platelet metabolic markers, a measurement of platelet calcium fluxes, a measurement of intracellular calcium, a measurement of platelet aggregability, a measurement of platelet granule release, and a measurement of platelet hormone synthesis and release.

a method of forcing the reverse transport of cholesterol from peripheral tissues to the liver in a warm blooded mammal and delivering the cholesterol to the liver while controlling plasma LDL concentrations, comprising the step of delivering the cholesterol to the liver at a sufficiently slow rate so that hepatic cholesterol homeostasis is free of substantial disruption by administration of an agent, the agent selected from the group consisting of large liposomes and small acceptors to a subject.

a method described above in which the large liposomes are chemical compositions of liposomes of a size, function or composition so that the liposomes are cleared slowly by the liver.

a method described above in which the step of delivering comprises slowly infusing the liposomes.

a method described above in which the step of delivering comprises administering small doses of the liposomes, separated in time, to avoid increasing the LDL concentration.

a method described above further comprising the step of periodically assaying the plasma LDL concentrations with an assay to obtain an assayed LDL concentration, the assay selected from the group consisting of an assay of plasma esterified cholesterol, an assay of plasma apolipoprotein-B, a gel filtration assay of plasma, an ultracentrifugal assay of plasma, and a precipitation assay having a component, the component selected from the group consisting of polyanions, divalent cations, and antibodies, an ultracentrifugal assay of plasma, a precipitation assay, a immunoturbidometric assay, and an electrophoretic assay to determine the level of a therapeutically effective amount of each of the liposomes.

a method of forcing the reverse transport of cholesterol from peripheral tissues to the liver in vivo and delivering the cholesterol primarily to hepatic Kupffer cells rather than hepatic parenchymal cells so that hepatic cholesterol homeostasis is not harmfully disrupted and controlling the homeostasis and effecting a plasma component, comprising the step of administering an effective amount of liposomes, the liposomes selected from the group of liposomes being substantially incapable of penetrating endothelial fenestrae of the liver and incapable of substantially interacting with hepatic parenchymal cells and the liposomes being of a size, composition or shape so that the liposomes are directed away from the hepatic parenchymal cells.

a method described above further comprising the step of periodically monitoring the plasma component with an assay, the assay selected from the group consisting of an assay for plasma unesterified cholesterol and phospholipid, an assay of bile acids and cholesterol in stool, an assay of bile acids and cholesterol in bile, an assay of hepatic gene expression in a liver biopsy, an assay of hepatic gene expression in peripheral blood leukocytes, the gene comprising a gene involved in cholesterol metabolism, an assay of plasma LDL concentration, and a vascular imaging technique.

a method of forcing the reverse transport of cholesterol from a body part, the body part selected from the group of organs, peripheral tissues, cells, and platelets in vivo, and modifying the lipid composition of membranes, the cells, tissues, organs, and other extracellular structures, comprising the step of administering for a treatment period a therapeutically effective amount of a multiplicity of non-liposomal particles for cholesterol depletion of peripheral tissues while avoiding harmful disruptions of hepatic cholesterol homeostasis, the particles being selected from the group of a particle substantially free of cholesterol and particles free of cholesterol.

a method described above in which the non-liposomal particles are selected from the group consisting of triglyceride-phospholipidemulsions, the emulsions selected from the group of emulsions that are not taken up rapidly by hepatic parenchymal cells, emulsions that are not taken up to a large extent by parenchymal cells, triglyceride-phospholipid-protein emulsions, and emulsions taken up slowly by the liver.

a method of controlling plasma LDL levels in vivo and lowering blood viscosity, comprising the step of parenterally administering a therapeutically effective amount of a multiplicity of large liposomes comprised of phospholipids a substantially free of sterol for a treatment period, the effective amount administered in a dosage, the dosage selected from a single dose and repeated doses.

a method described above further comprising the steps of taking a measurement, the measurement selected from the group consisting of a measurement of blood flow in a carotid artery, measurement of blood flow in a coronary artery, a measurement of blood flow in a lower limb, an ultrasound measurement of blood flow in other vessels, an MRI measurement of blood flow, a radioisotope tracer measurement of blood flow, and a measurement of blood viscosity.

a method of controlling plasma LDL levels in vivo and reducing the sphingomyelin to phosphatidylcholine ratio in a cell membrane and cell aging, comprising the step of parenterally administering a therapeutically effective amount of a multiplicity of large liposomes comprised of phospholipids substantially free of sterol for a treatment period, the effective amount administered in a dosage, the dosage selected from a single dose and repeated doses.

a method described above further comprising the step of periodically assaying the cells with an assay, the assay selected from the group consisting of an assay of sphingomyelin, an assay of phosphatidylcholine, an assay of membrane function, and an assay of cellular function.

a method of controlling hepatic secretion of apolipoprotein-B while forcing the reverse transport of cholesterol from peripheral tissues to the liver, comprising the step of parenterally administering a therapeutically effective amount of a multiplicity of large liposomes comprised of phospholipids substantially free of sterol for a treatment period, the effective amount administered in a dosage, the dosage selected from a single dose and repeated doses.

a method of controlling plasma LDL levels and hepatic cholesterol homeostasis and gene expression and blocking uptake of atherogenic lipoproteins by cells of the arterial wall of a subject, comprising the step of parenterally administering a therapeutically effective amount of a multiplicity of liposomes, the liposomes selected from the group consisting of large liposomes comprised of phospholipids substantially free of sterol and small acceptors for a treatment period, the therapeutic amount given in a dosage, the dosage selected from a single dose and repeated doses.

a method described above further comprising the step of diagnosing the efficacy of the administration by performing an assay, the assay selected from the group consisting of an assay of arterial uptake and retention of lipoproteins, an assay of uptake of lipoproteins of the subject by cells in culture, the lipoproteins disposed in whole plasma, whole blood, and plasma fractions from the subject, an assay of arterial function, an assay of oxidized lipid in an artery or plasma, an assay of oxidized lipids, and an assay of lesion size.

a method of controlling plasma LDL levels, hepatic cholesterol homeostasis, and hepatic gene expression in vivo while altering plasma HDL, comprising the step of parenterally administering a therapeutically effective amount of a multiplicity of liposomes, the liposomes selected from the group consisting essentially of large liposomes comprised of phospholipids substantially free of sterol and acceptors for a treatment period, the effective amount administered in a dosage, the dosage selected from a single dose and repeated doses.

a method described above in which the small acceptors are selected from the group consisting of a small acceptor of cholesterol, an acceptor of sphingomyelin, an acceptor of lysophosphatidylcholine, an acceptor of a protein, and an acceptor of a lipid.

a method described above further comprising the step of diagnosing the efficacy of the administration by performing an assay, the assay selected from the group consisting of an assay of HDL, an assay of HDL unesterfied cholesterol, an assay of HDL cholesteryl ester, an assay of HDL phospholipid, an assay of HDL protein, an assay of protein species, an assay of HDL size, a functional assay of the ability of HDL to extract cholesterol from cells, and a functional assay of the ability of HDL to alter cell membrane composition, and a functional assay of whole plasma to determine the ability of the whole plasma to extract cholesterol from cells in vitro a method of suppressing the rise in plasma concentrations of atherogenic lipoproteins after administration of an agent having small acceptors of cholesterol, other lipids or compounds in a warm blooded mammal comprising the step of co-administering an effective amount of a multiplicity of an agent having large liposomes comprised of phospholipids substantially free of sterol with the administration of the agent having the small acceptors.

a method described above in which the atherogenic lipoproteins are selected from the group consisting of LDL, VLDL, IDL, β-VLDL, Lp(a), a lipoprotein containing apolipoprotein-B, oxidized lipoproteins, and modified lipoproteins.

a method described above in which the agent having small acceptors consists essentially of small acceptors and in which the agent having large liposomes consists essentially of large liposomes.

a method described above in which the co-administration of the agent having large liposomes is simultaneous with the administration of the agent having small acceptors.

a method described above n which the co-administration of the agent having large liposomes is separated in time from the administration of the agent having small acceptors by an effective time period.

a method described above in which the effective time period is in the range of about 1 minute to about two weeks.

a method described above in which atherogenic lipoprotein concentrations are controlled.

a method described above in which the atherogenic lipoprotein concentrations are optionally controlled through adjusting a dosage, size or composition of liposomes.

an improved method of dialysis in which the improvement comprises the step of administering a therapeutically effective amount of an agent, the agent selected from the group consisting of a multiplicity of large liposomes comprised of phospholipids substantially free of sterol, small acceptors, an acceptor of cholesterol, and an acceptor of lipid, during operation of a dialysis device.

a method in which the dialysis is selected from the group consisting of hemodialysis, peritoneal dialysis, and rectal dialysis.

a method described above in which the agent is added directly to blood or blood plasma.

a method described above in which the administration of the agent is selected from the group consisting of extracorporeal administration and intracorporal administration.

a method described above in which the agent is added directly to dialysate of the patient, the dialysate optionally including extracorporeal dialysate, intraperitoneal dialysate, and intrarectal dialysate.

a method described above in which plasma component concentrations and properties are periodically assayed using an assay, the components selected from the group consisting of LDL, HDL, unesterified cholesterol, phospholipid, IDL, VLDL, Lp(a), βVLDL, liposome acceptors, apolipoprotein-B, and cholesteryl ester.

a method described above further comprising the step of administering LDL lowering agents or optionally adjusting a liposome dosage or liposome size where LDL or other atherogenic lipoproteins are found to be at inappropriate levels.

a method described above further comprising the step of administering HDL raising agents where HDL or other anti-atherogenic lipoproteins are found not to be at appropriate levels in response to results of the assay.

a method described above in which the patient has cells, and further comprising the steps of treating the patient's cells, together or after separation of the cells into erthrocytes, leukocytes, and platelets, extracorporeally with liposomes, and periodically assaying a component, the component selected from the group consisting of cellular cholesterol, phospholipid, fluidity, fragility, gene expression, hormone secretion, an ion flux, and cell function.

a method described above in which the amount is adjusted where the cellular fragility increases, or in accordance with an altered cell function or property.

a method described above in which the dialysate is assayed for cholesterol or assayed for other exchangeable material to determine the effectiveness of the treatment.

a method described above the amount is regulated as a function of the rate of removal of cholesterol or other exchangeable material.

a method described above in which the acceptor is an acceptor of sphingomyelin.

a method described above in which the acceptor of lipid is selected from the group consisting of an acceptor of an oxidized lipid, an emulsion, and protein-phospholipid complex.

a method described above further comprising the step of minimizing a rise in plasma LDL levels.

an improved method of dialysis treatment of a patient in which the improvement comprises the step of admixing a dialysate with a therapeutically effective amount of an agent, the agent selected from the group consisting of a multiplicity of small liposomes so that the small liposomes do not substantially enter the circulation of a subject in large amounts.

a method described above in which the small liposomes are admixed so as to minimize a rise in plasma LDL or other atherogenic proteins.

a method described above in which plasma component concentrations and properties are periodically assayed using an assay, the assay being selected from the group consisting of an assay of plasma esterified cholesterol, an assay of plasma apolipoprotein-B, a gel filtration assay of plasma, an ultracentrifugal assay of plasma, a precipitation assay of plasma, and a immuno-turbidometric assay of plasma.

a method described above in which the large liposomes are of a size and shape larger than fenestrations of an endothelial layer lining hepatic sinusoids in a liver, whereby the liposomes are too large to readily penetrate the fenestrations.

a method described above in which the therapeutically effective amount is in the range of about 10 mg to about 1600 mg phospholipid per kg body weight per dose.

a method described above in which the large liposomes are given periodically during the treatment period.

a method described above in which the large liposomes are selected from the group consisting of uni-lamellar liposomes and multi-lamellar liposomes.

a method described above in which the liposomes have diameters larger than about 50 nm.

a method described above in which the liposomes have diameters larger than about 80 nm.

a method described above in which the liposomes have diameters larger than about 100 nm.

a method of regulating hepatic parenchymal cell cholesterol content, the cell having at least one gene selected from the group consisting of a gene for an LDL receptor, a gene for HMG-CoA reductase, a gene for cholesterol 7-alpha-hydroxylase, and a gene regulating a function involved in cholesterol homeostasis; and, homeostasis thereof, comprising the step of administering a therapeutically effective amount of a multiplicity of large liposomes comprised of phospholipids substantially free of sterol during a treatment period.

a method described above further comprising the steps of periodically assaying a property, the property selected from the group consisting of concentration, composition, and characteristic of atherogenic lipoproteins in plasma with an assay during the treatment period to assess the plasma atherogenic lipoprotein and to obtain a atherogenic lipoprotein profile, and adjusting the parenteral administration in response to the profile.

a method described above in which the assay is selected from the group consisting of an assay of plasma esterified cholesterol, an assay of plasma apolipoprotein-B, a gel filtration assay of plasma, an ultracentrifugal assay of plasma, a precipitation assay of plasma, an electrophoretic assay, an electron microscopic assay, an immuno-turbidometric assay, and an assay of lipoprotein composition, size or function.

a method described above further comprising the step of enhancing tissue penetration of a cholesterol acceptor and enhancing extraction of tissue cholesterol and other exchangeable material with co-administration of an effective amount of a compound, the compound selected from the group consisting of a small acceptor of cholesterol, an amphipathic compound, and a drug that increases endogenous small acceptors of cholesterol.

a method described above in which the small acceptor is selected from the group consisting of a high-density lipoprotein, a phospholipid protein complex having a group selected from the group consisting of apoA-I, apoA-II, apoA-IV, apoE, synthetic fragments thereof, natural fragments thereof, an amphipathic protein, and an amphipathic peptide, the protein substantially free of phospholipid, small phospholipid liposomes, and a small cholesterol acceptor; the drug including an agent that raises endogenous HDL concentrations, the agent selected from the group consisting of nicotinic acid, ethanol, a fibric acid, a cholesterol synthesis inhibitor, a drug that increases HDL concentrations, and derivatives thereof.

a method described above in which the co-administration of the compound is simultaneous with the administration of the large liposomes.

a method described above in which the co-administration of the compound is separated in time from the parenteral administration of the therapeutically effective amount of a multiplicity of the large liposomes by an effective time period.

a method described above in which the effective time period is in the range of about 1 minute to about two weeks.

a method described above in which the therapeutically effective amount is in the range of about 10 to about 1600 mg/kg/dose.

a method described above in which the liposomes are given in repeated doses.

a method described above further comprising the step of controlling the expression of the genes by the parenteral administration of a multiplicity of the large liposomes.

a method described above 1 in which the parenchymal cell functions in a system having hepatic sinusoids, an endothelial layer lining the hepatic sinusoids, and fenestrations; and, in which the large liposomes are of a size and shape larger than the fenestrations of the endothelial layer lining the hepatic sinusoids or in which the large liposomes optionally having other properties that prevent the large liposomes from penetrating the fenerstrations, whereby the large liposomes have properties to prevent the ready penetration of the fenestrations.

a method described above in which the large liposomes are selected from the group consisting of uni-lamellar liposomes and multi-lamellar liposomes.

a method described above in which the liposomes have diameters larger than about 50 nm.

a method described above in which the liposomes have diameters larger than about 80 nm.

a method described above in which the liposomes have diameters larger than about 100 nm.

a method described above in which administration is selected from the group of intravenous administration, intra-arterial administration, intramuscular administration, subcutaneous administration, transdermal administration, intrathecal administration, via lymphatics, intravascular administration, rectal administration, via a chronically indwelling catheter or other device, via an acutely placed catheter or other device, and intraperitoneal administration.

a method of suppressing hepatic expression of a cholesterol ester transfer protein gene in a warm blooded mammal comprising the step of administering a therapeutically effective amount of a multiplicity of large liposomes comprised of phospholipids, the phospholipids selected from the group of phospholipids substantially free of sterol and phospholipids containing sterol, for an effective period of time, whereby plasma LDL and HDL are controlled as a result of the administration.

a method described above further comprising the step of periodically assaying plasma LDL concentrations with an assay during the treatment period to assess the plasma LDL.

a method described above in which the assay is selected from the group consisting of an assay of plasma esterified cholesterol, an assay of plasma apolipoprotein-B, a gel filtration assay of plasma, an ultracentrifugal assay of plasma, a precipitation assay of plasma, an electrophoretic assay, an electron microscopic assay, an immuno-turbidometric assay of plasma, and an assay of lipoprotein composition, size or function.

a method described above in which the liposomes are given periodically.

a method described above in which the therapeutically effective amount is in the range of about 10 mg/kg/dose to about 1600 mg/kg/dose.

a method described above further comprising the step of enhancing tissue penetration of a cholesterol acceptor and enhancing extraction of tissue cholesterol and other exchangeable material with co-administration of an effective amount of a compound, the compound selected from the group consisting of a small acceptor of cholesterol, an amphipathic compound, and a drug that increases endogenous small acceptors of cholesterol.

a method described above in which the small acceptor is selected from the group consisting of a high-density lipoprotein, a phospholipid protein complex having a group selected from the group consisting of apoA-I, apoA-II, apoA-IV, apoE, synthetic fragments thereof, natural fragments thereof, an amphipathic protein, and an amphipathic peptide, the protein substantially free of phospholipid, small phospholipid liposomes, and a small cholesterol acceptor; the drug including an agent that raises physiologic HDL concentrations, the agent selected from the group consisting of nicotinic acid, ethanol, a fibric acid, a cholesterol synthesis inhibitor, a drug that increases HDL concentrations, and derivatives thereof.

a method described above further comprising the step of periodically assaying plasma LDL concentrations with an assay during the treatment period to assess the plasma LDL.

a method described above in which the assay is selected form the group consisting of an assay of plasma esterified cholesterol, an assay of plasma apolipoprotein-B, a gel filtration assay of plasma, an ultracentrifugal assay of plasma, a precipitation assay of plasma, an electrophoretic assay, an electron microscopic assay, and a immuno-turbidometric assay of plasma.

a method described above in which the co-administration of the compound with the administration of the large liposomes is simultaneous.

a method described above in which the co-administration of the compound is separated in time from the parenteral administration of the therapeutically effective amount of a multiplicity of the large liposomes by an effective time period.

a method described above in which the separation in time is in the range of about 1 minute to about two weeks.

a method described above in which the large liposomes are of a size and shape larger than fenestrations of an endothelial layer lining hepatic sinusoids or in which the large liposomes optionally having other properties that prevent the large liposomes from penetrating the fenerstrations, whereby the large liposomes have properties to prevent the ready penetration of the fenestrations.

a method described above in which the large liposomes are selected from the group consisting of uni-lamellar liposomes and multi-lamellar liposomes.

a method described above in which the liposomes have diameters larger than about 50 nm.

a method described above in which the liposomes have diameters larger than about 80 nm.

a method described above in which the liposomes have diameters larger than about 100 nm.

a method of controlling hepatic expression of a gene while forcing the reverse transport of cholesterol from peripheral tissues to the liver in a warm blooded mammal, comprising the step of parenterally administering a therapeutically effective amount of a multiplicity of large liposomes comprised of phospholipids substantially free of sterol for a treatment period, the effective amount administered in a dosage, the dosage selected from a single dose and repeated doses.

a method of controlling plasma LDL levels, hepatic cholesterol homeostasis, arterial enzymes, platelet function, and hepatic gene expression in an animal, comprising the step of parenterally administering a therapeutically effective amount of a multiplicity of large liposomes comprised of phospholipids substantially free of sterol for a treatment period, the effective amount administered in a dosage, the dosage selected from a single dose and repeated doses.

a method described above further comprising the step of diagnosing the efficacy of the administration by taking a measurement of enzyme activity, the measurement selected from the group consisting of a measurement of an arterial lipase activity, a measurement of arterial triglyceride lipase activity, a cholesterol esterase activity, a measurement of lysophospholipase activity, a measurement of an arterial lipid esterase activity, a measurement of arterial ACAT activity, a measurement of endothelial-derived relaxing factor, a measurement of intracellular calcium concentration in arterial cells, a measurement of arterial cell proliferation, an assay of arterial enzymes, an assay in the presence of calcium channel blockers, a measurement of nitric oxide synthesis, an assay of arterial uptake of liposomes, an assay of arterial uptake, accumulation and retention of lipoproteins, an assay of arterial retention of liposomes, an assessment of platelet function, an assessment of arterial function, an assessment of gene function, and a measurement of an effect of a biologically active substrate of the enzyme.

a method described above in which the substrate is lysophosphatidylcholine.

a composition for controlling cholesterol related genes, enzymes and other compounds while forcing the reverse transport of lipids peripheral tissues to the liver consisting essentially of large liposomes sized and shaped to interact with molecules interacting with the genes, enzymes or other compounds, the large liposomes being substantially free of sterol.

a method described above in which the atherogenic lipoprotein is selected from the group consisting of LDL, VLDL, IDL, Lp(a), $\beta$-VLDL and a lipoprotein that comprises apolipoprotein B.

a method described above in which the parenchymal cell functions in a system having hepatic sinusoids, an endothelial layer lining the hepatic sinusoids, and fenestrations; and, in which the large liposomes have properties that provide for the slow and steady delivery of cholesterol to the liver, and reduce protein uptake.

a method described above further comprising the steps of periodically assaying a CETP property, the property selected from the group consisting of plasma CETP concentration and CETP activity and adjusting the effective amount in response thereto.

a method described above in which an atherogenic lipoprotein selected from the group consisting of LDL, VLDL, IDL, Lp(a), $\beta$-VLDL and a lipoprotein that comprises apolipoprotein B, is controlled.

a method described above further comprising the steps of periodically assaying a property, the property selected from the group consisting of concentration, composition, and characteristic of atherogenic lipoproteins in plasma with an assay during the treatment period to assess the plasma atherogenic lipoprotein and to obtain a atherogenic lipoprotein profile, and adjusting the parenteral administration in response to the profile.

a method described above further comprising the steps of periodically assaying a CETP property, the property selected from the group consisting of plasma CETP concentration and CETP activity and adjusting the effective amount in response thereto.

A method described above in which an atherogenic lipoprotein selected from the group consisting of LDL, VLDL, IDL, Lp(a), $\beta$-VLDL and a lipoprotein that comprises apolipoprotein B, is controlled.

a method described above further comprising the steps of periodically assaying a property, the property selected from the group consisting of concentration, composition, and characteristic of atherogenic lipoproteins in plasma with an assay during the treatment period to assess the plasma atherogenic lipoprotein and to obtain a atherogenic lipoprotein profile, and adjusting the parenteral administration in response to the profile.

a method described above in which the gene is selected from the group consisting of genes controlling the hepatic expression of 7-alpha hydroxylase, hepatic expression of an LDL receptor, hepatic expression of HMG Co A reductase, and derivatives thereof.

a method of diagnosing a side-effect of reverse transport of cholesterol from peripheral tissues to the liver in vivo accompanying parenteral administration of a multiplicity of large liposomes and small liposomes during a treatment period, comprising the step of periodically assaying plasma atherogenic lipoprotein concentrations with an assay to obtain an assayed atherogenic lipoprotein concentration, the assay selected from the group consisting of an assay of plasma esterified cholesterol, an assay of plasma apolipoprotein-B, a gel filtration assay of plasma, an ultracentrifugal assay of plasma, and a precipitation assay having a component, the component selected from the group consisting of polyanions, divalent cations, and antibodies, an assay of triglyceride in plasma, and an immunoturbidometric assay of plasma, to determine the level of a therapeutically effective amount of each of the liposomes, whereby a side effect of administration of the liposomes is diagnosed and effectively regulated.

a method described above in which the atherogenic lipoprotein is LDL.

a method described above further comprising the step of adding an emulsion and an agent to increase reverse transport of cholesterol from peripheral tissues to the liver.

a method described above in which the agent is selected from the group consisting of protein-phospholipid complexes and HDL.

a method of diagnosing and treating a side-effect of reverse transport of cholesterol from peripheral tissues to the liver in a warm blooded animal accompanying parenteral administration of a multiplicity of large liposomes and small liposomes during a treatment period, comprising the steps of periodically assaying plasma atherogenic protein concentrations with an assay to obtain an assayed atherogenic protein concentration, the assay selected from the group consisting of an assay of plasma esterified cholesterol, an assay of plasma apolipoprotein-B, a gel filtration assay of plasma, an ultracentrifugal assay of plasma, and a precipitation assay having a component, the component selected from the group consisting of polyanions, divalent cations, and antibodies, an assay of triglyceride in plasma, an immunoturbidometric assay of plasma, to determine the level of a therapeutically effective amount of each of the liposomes, and an electrophoretic assay, and an electron microscopy assay; and, adjusting the therapeutically effective amount of each of the small and large liposomes in response to the assayed LDL concentration during the treatment period.

a method described above in which the atherogenic lipoprotein is LDL.

a method described above further comprising the steps of co-administering a pharmaceutical agent to lower the atherogenic protein concentration with the liposome administration, and adjusting the administration of the agent responsive to the assayed LDL concentration.

a method described above in which the atherogenic lipoprotein is LDL.

a method described above further comprising the step of adding an emulsion and an agent to increase reverse transport of cholesterol from peripheral tissues to the liver.

a method described above in which the agent is selected from the group consisting of protein-phospholipid complexes and HDL.

a pharmaceutical composition consisting essentially of unilamellar liposomes having an average diameter of about 100–150 nanometers, which liposomes are not bound to a drug; and a pharmaceutically acceptable carrier.

a pharmaceutical composition described above wherein the liposomes are bound to apoproteins.

a pharmaceutical composition described above wherein the liposomes have an average diameter of about 125 nanometers.

a pharmaceutical composition described above wherein the liposomes comprise at least one phospholipid.

a pharmaceutical composition described above wherein the phospholipid is egg phosphatidylcholine, egg phosphatidylglycerol, distearoylphosphatidylcholine, or distearoylphosphatidylglycerol.

a pharmaceutical composition described above wherein the liposome comprises phosphatidylcholine and egg phosphatidylglycerol.

a pharmaceutical composition wherein the liposome is liquid-crystalline at 37 degrees C.

a method for treating atherosclerosis in an animal comprising administering a liposome composition to the animal, which liposome composition consists essentially of unilamellar liposomes having an average diameter of about 100 150 nanometers.

a method described above wherein the unilamellar liposomes have an average diameter of 125 nanometers.

a method described above wherein the liposomes comprise at least one phospholipid.

a method described above wherein the phospholipid is egg phosphatidylcholine, egg phosphatidylglycerol, distearoylphosphatidylcholine, or distearoylphosphatidylglycerol.

a method described above wherein the liposome comprises egg phosphatidylcholine and egg phosphatidylglycerol.

a method described above wherein the liposome is liquid-crystalline at 37 degrees C.

a method described above wherein the liposome composition is administered parenterally.

a method described above wherein the liposome composition is administered intravenously.

a method described above further comprising repeating the administration of the liposome composition.

a method described above wherein the liposome composition is administered every 7–14 days.

a method for treating atherosclerosis in an animal comprising administering a liposome composition to the animal, which liposome composition consists essentially of unilamellar liposomes having an average diameter of about 125 nanometers.

a method described above wherein the liposome composition is administered intravenously.

a method described above wherein the liposome composition is administered at least twice.

a method described above wherein the liposomes comprise egg phosphatidyl choline.

a method described above wherein the liposomes comprise egg phosphatidyl choline and egg phosphatidylglycerol.

While only a few, preferred embodiments of the invention have been described hereinabove, those of ordinary skill in the art will recognize that the embodiment may be modified and altered without departing from the central spirit and scope of the invention. Thus, the preferred embodiment described hereinabove is to be considered in all respects as illustrative and not restrictive, the scope of the invention being indicated by the appended claims, rather than by the foregoing description, and all changes which come within the meaning and range of equivalency of the claims are intended to be embraced herein.

We claim:

1. A method for treating a vascular disease or condition selected from the group consisting of atherosclerosis, hypercholesterolemia and hypoalphalipoproteinemia in a human, comprising administering to a human in need thereof a pharmaceutically acceptable and a therapeutically effective amount of unilamellar phospholipid liposomes having empty aqueous cores and having a Gaussian distribution wherein at least about 68% of the liposomes have a mean diameter of 125±30 nm.

2. A method for treating a vascular disease or condition selected from the group consisting of atherosclerosis, hypercholesterolemia and hypoalphalipoproteinemia in a human, comprising administering to a human in need thereof a pharmaceutically acceptable and a therapeutically effective amount of unilamellar phospholipid liposomes having empty aqueous cores and having a Gaussian distribution wherein at least about 68% of the liposomes have a mean diameter between 100–150 nm.

3. The method of claim 1 or 2 in which the therapeutically effective amount is about 10 mg to about 1600 mg per kg body weight.

4. The method of claim 1 or 2 in which the therapeutically effective amount is about 300 mg per kg body weight.

5. The method of claim 1 or 2 in which the therapeutically effective amount is about 0.1 to 1.5 gm/kg.

6. The method of claim 1 or 2 in which the therapeutically effective amount is about 0.28 to 0.42 gm/kg.

7. The method of claim 1 or 2 in which the liposomes are administered once.

8. The method of claim 1 or 2 in which the liposomes are administered more than once.

9. The method of claim 1 or 2 in which the liposomes are administered in repeated doses.

10. The method of claim 1 or 2 in which said liposomes are administered weekly.

11. The method of claim 1 or 2 in which said liposomes are administered once per week for 4 to 16 weeks.

12. The method of claim 1 or 2 in which said liposomes are administered once per week for 10 weeks.

* * * * *